United States Patent
Liu et al.

(10) Patent No.: US 9,512,407 B2
(45) Date of Patent: Dec. 6, 2016

(54) CELLS AND METHODS FOR OBTAINING THEM

(75) Inventors: Pentao Liu, London (GB); Wei Wang, London (GB); Jian Yang, London (GB)

(73) Assignee: GENOME RESEARCH LIMITED, London (GB)

(*) Notice: Subject to any disclaimer, the term of this patent is extended or adjusted under 35 U.S.C. 154(b) by 470 days.

(21) Appl. No.: 13/394,481

(22) PCT Filed: Sep. 7, 2010

(86) PCT No.: PCT/GB2010/051493
§ 371 (c)(1),
(2), (4) Date: Aug. 29, 2012

(87) PCT Pub. No.: WO2011/027180
PCT Pub. Date: Mar. 10, 2011

(65) Prior Publication Data
US 2012/0315703 A1   Dec. 13, 2012

Related U.S. Application Data

(60) Provisional application No. 61/240,282, filed on Sep. 7, 2009, provisional application No. 61/276,203, filed on Sep. 8, 2009.

(30) Foreign Application Priority Data

Sep. 7, 2009  (GB) .................................. 0915523.5

(51) Int. Cl.
C12N 15/00   (2006.01)
C12N 15/02   (2006.01)
A01N 63/00   (2006.01)
C12N 5/074   (2010.01)

(52) U.S. Cl.
CPC ....... *C12N 5/0696* (2013.01); *C12N 2501/235* (2013.01); *C12N 2501/385* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2510/00* (2013.01)

(58) Field of Classification Search
USPC ....................................... 435/455, 320.1, 325
See application file for complete search history.

(56) References Cited

U.S. PATENT DOCUMENTS

2005/0148590 A1   7/2005  Tsang et al.
2007/0224615 A1*  9/2007  Lee ..................... C12Q 1/6897
                                              435/6.16
2009/0246875 A1   10/2009 Yamanaka et al.

FOREIGN PATENT DOCUMENTS

| EP | 0545554 A2 | 6/1993 |
|---|---|---|
| EP | 0683227 A1 | 11/1995 |
| EP | 1970446 A1 * | 12/2006 |
| WO | WO 01/83434 A2 | 11/2001 |
| WO | WO 2005/080973 A1 | 9/2005 |
| WO | WO 2005/082344 A1 | 9/2005 |
| WO | WO 2007/016566 A2 | 2/2007 |
| WO | WO 2008/064136 A2 | 5/2008 |
| WO | WO 2009/067182 A2 | 5/2009 |
| WO | WO 2009/075119 A1 | 6/2009 |
| WO | WO 2011/040887 A1 | 4/2011 |

OTHER PUBLICATIONS

Yu (Science, May 8, 2009, vol. 324, No. 5928, p. 797-801).*
Takahashi (Cell, 2006, vol. 126:663-676).*
Yu (Science, 2007, vol. 318, p. 1917-1920).*
Park (Nature, Jan. 2008, vol. 451, p. 141-146).*
Aoi (Science, Aug. 1, 2008, vol. 321, No. 5889, p. 699-702, available online Feb. 14, 2008).*
Nakagawa (Nat Biotechnol, Jan. 2008, vol. 26: 101-106).*
Feng (Cell Stem Cell, Apr. 3, 2009, vol. 4, p. 301-312).*
Gonzalez (PNAS, Jun. 2, 2009, vol. 106, No. 22, p. 8918-8922).*
Papapetrou (PNAS, Aug. 4, 2009, vol. 106, No. 31, p. 12759-12764).*
Wang (PNAS, Nov. 8, 2011, vol. 108, No. 45, p. 18283-18288).*
Barnea (J. Biol. Chem, 2000, vol. 275, No. 9, p. 6608-6619).*
Takahashi et al., "Induction of Pluripotent Stem Cells from Adult Human Fibroblasts by Defined Factors," Cell, vol. 131:861-872, 2007.
Wang et al., "Rapid and efficient reprogramming of somatic cells to induced pluripotent stem cells by retinoic acid receptor gamma and liver receptor homolog 1," Proc. Natl. Acad. Sci. USA, vol. 108(45):18283-18288, 2011.
Barnea and Bergman, "Synergy of SF1 and RAR in Activation of Oct-3/4 Promoter," J. Biol. Chem. 275(9):6608-6619 (2000).
Feng et al., "Molecules that Promote or Enhance Reprogramming of Somatic Cells to Induced Pluripotent Stem Cells," Cell Stem Cell 4(4):301-312 (2009).

(Continued)

*Primary Examiner* — Michael Wilson

(74) *Attorney, Agent, or Firm* — Cooley LLP

(57) ABSTRACT

Reprogrammed somatic cells, methods for reprogramming, reprogramming factors for somatic cells and uses of such factors and cells are described. Nuclear reprogramming factors [NRF] described comprise one or more of a gene product or a polynucleic acid encoding a gene product from a retinoic acid receptor (RAR/RXR) family member, or an agonist or antagonist thereof; a gene product from an Lrh1 family member; or an agonist thereof; retinoic acid or a gene product involved in synthesizing or metabolizing retinoic acid; or an agonist or antagonist thereof; or a gene product that is involved in transporting a retinoic acid family member.

11 Claims, 36 Drawing Sheets

(56) References Cited

OTHER PUBLICATIONS

Figure 1:
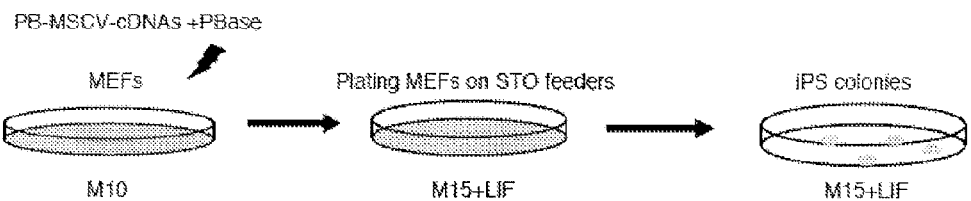
Figure 1:
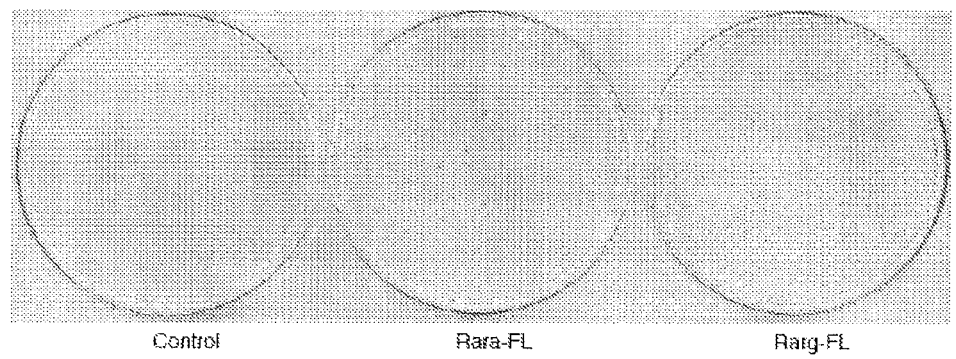
Figure 1:
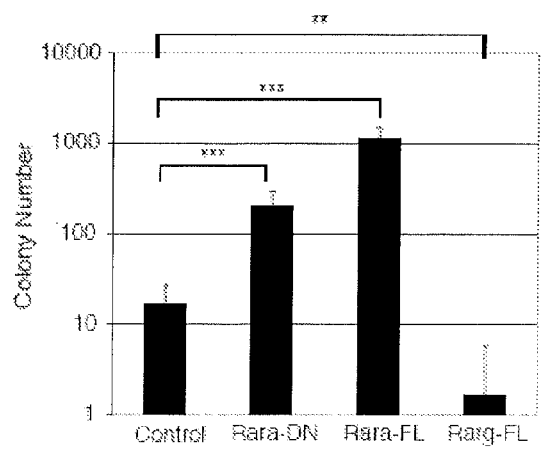
Figure 1:
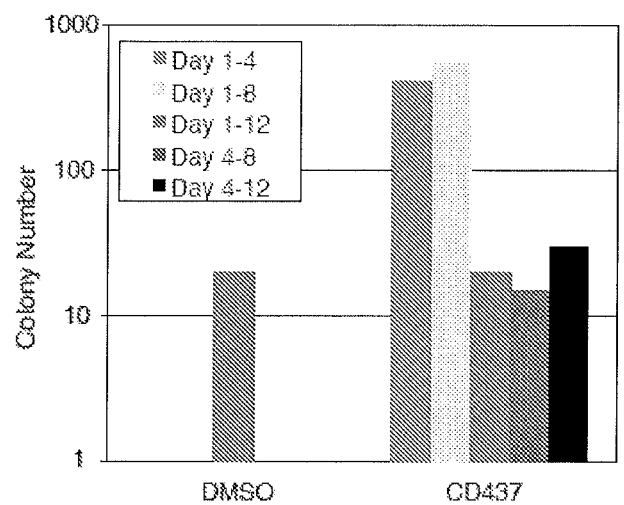
Figure 1:
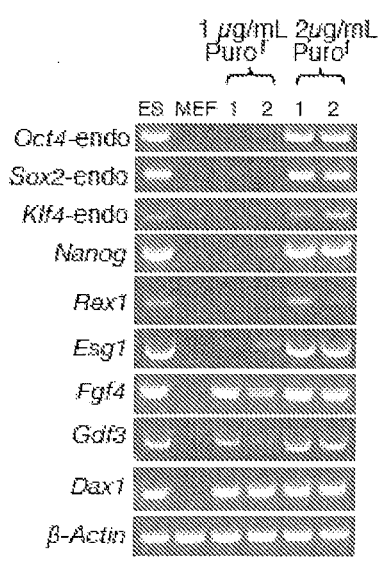
Figure 1:
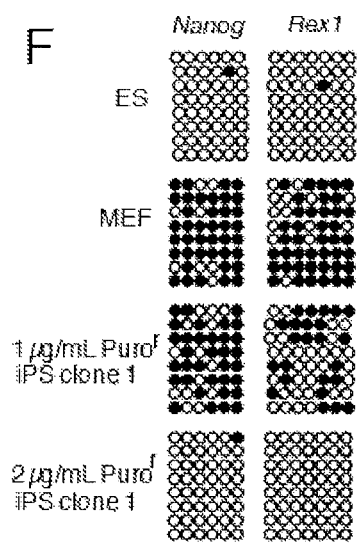
Figure 1:
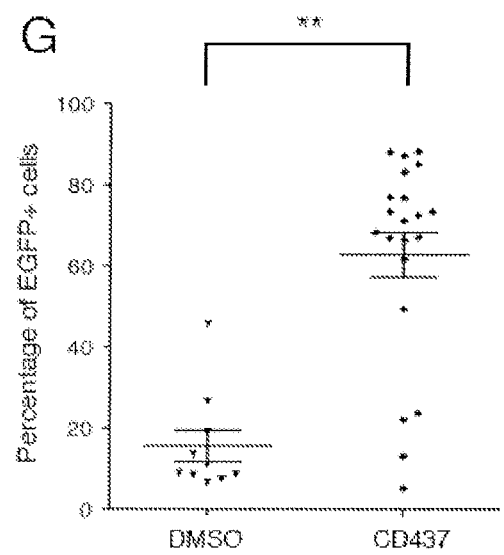

Feng et al., "Reprogramming of fibroblasts into induced pluripotent stem cells with orphan nuclear receptor Esrrb," Nat. Cell Biol. 11(2):197-203 (2009).
Gu et al., "Orphan Nuclear Receptor LRH-1 Is Required to Maintain Oct4 Expression at the Epiblast Stage of Embryonic Development," Mol. Cell. Biol. 25(9):3492-3505 (2005).
Kaye, "Patent Act 1977: Search Report under Section 17(5)," 4 pages, Great Britain Appl. No. GB 0915523.5, British Intellectual Property Office (mailed Jan. 8, 2010).
Kaye, "Patent Act 1977: Search Report under Section 17(6)," 3 pages, Great Britain Appl. No. GB 0915523.5, British Intellectual Property Office (mailed Feb. 18, 2010).
Mullen et al., "Nuclear Receptors in Regulation of Mouse ES Cell Pluripotency and Differentiation," PPAR Res. 2007, Article ID 61563, 10 pages. (2007).
NCBI Accession NM_000966, *Homo sapiens* retinoic acid receptor, gamma (RARG), transcript variant 1, mRNA 8 pages, Mar. 1999.
NCBI Accession NM_003822, *Homo sapiens* nuclear receptor subfamily 5, group A, member 2 (NR5A2), transcript variant 2, mRNA, 8 pages, Mar. 1999.
Novak-Giese, "International Search Report," 4 pages, International Patent Appl. No. PCT/GB2010/051493, European Patent Office (mailed Nov. 30, 2010).
Novak-Giese, "Written Opinion of the International Searching Authority," 8 pages, International Patent Appl. No. PCT/GB2010/051493, European Patent Office (mailed Nov. 30, 2010).
Takahashi and Yamanaka, "Induction of Pluripotent Stem Cells from Mouse Embryonic and Adult Fibroblast Cultures by Defined Factors," Cell 126(4):663-676 (2006).
Williams et al., "Large-scale reprogramming of cranial neural crest gene expression by retinoic acid exposure," Physiol. Genomics 19:184-197 (2004).

\* cited by examiner

A

B

C

D

E

A

B

C

D

E

A

B

C

D

E

A

B

C

D

A

C

D

E

F

G

A

B

C

D

E

A

B

C

D

A

A

| Number of AP+ colonies after culturing in serum free medium for 17 days | | |
|---|---|---|
| Medium | PB-TRE-OCKS | PB-TRE-OCKS+PB-TRE-BL |
| LIF/Dox(4d) to 2i/LIF | 0;0;0 | 0;0;0 |
| LIF/Dox(8d) to 2i/LIF | 0;0;0 | 5;2;1 |
| LIF/Dox(12d) to 2i/LIF | 1;0;0 | 4;5;8 |
| 2i/LIF/Dox(17d) | 0;0;0 | 4;0;2 |

B

A

B

C

D

E

F

A

B

C

D

A

B

C

D

E

F

A

B

C

D

E

F

G

A

B

C

D

E

A

B

A

B

C

SEQUENCE LISTING

```
<160> NUMBER OF SEQ ID NOS: 111

<210> SEQ ID NO 1
<211> LENGTH: 1377
<212> TYPE: DNA
<213> ORGANISM: Homo sapiens

<400> SEQUENCE: 1
atggccacca ataaggagag actctttgcg cccggtgccc tggggcctgg atctggttac      60
ccaggagcag gcttcccatt cgccttccca ggtgcactca gagggtcgcc accatttgag     120
atgctgagcc ctagcttccg gggcctgggc cagcctgacc tccccaagga gatggcttct     180
ctctcggtgg agacacagag caccagctcg gaggagatgg tacccagctc tccctcaccc     240
ccaccacctc ctcgggtcta taagccatgc tttgtatgca atgacaagtc ttctggctac     300
cactatgggg tcagctcctg tgaaggctgc aagggcttct tcagacgcag cattcagaaa     360
aacatggtgt atacatgtca ccgtgacaaa aactgtatca tcaacaaggt caccagaaat     420
cgatgccagt actgcaggct acaaaagtgt ttcgaagtgg gcatgtccaa ggaagctgta     480
aggaacgatc gaaacaagaa gaaaaaggag gtaaaagagg agggctcgcc cgacagctat     540
gaactgagtc cacagttaga ggaactcatc accaaggtca gcaaagccca ccaggagact     600
tttccctcac tctgccagct gggcaagtac accacgaact ccagtgcaga tcaccgggtg     660
cagctggacc tggggctgtg ggacaagttc agcgagctgg ccaccaaatg catcatcaag     720
attgtggagt ttgcgaagcg gctgcctggt tttacagggc tcagcattgc cgaccagatc     780
```

| | |
|---|---|
| acgctgctca aggctgcttg tctggacatc ctaatgctgc ggatctgtac aaggtatacc | 840 |
| ccagagcagg acactatgac attctcggat gggctgaccc tgaaccgaac ccagatgcac | 900 |
| aatgctggct ttgggcccct tacagacctc gtctttgcct ttgccgggca gctgctgccc | 960 |
| ctggagatgg atgacaccga gactgggcta cttagtgcta tctgcctcat ctgtggagac | 1020 |
| cgaatggacc tggaagagcc cgagaaggtg gacaagctgc aggagcccct gctggaagcc | 1080 |
| ctgaggctct atgccggcg acggagaccc agccaaccct acatgttccc aaggatgctg | 1140 |
| atgaaaatca ccgacctccg gggcatcagc actaagggag cagaaagggc tataaccctg | 1200 |
| aagatggaga ttccaggccc gatgccaccc ctgatccgag agatgctgga gaacccggag | 1260 |
| atgtttgagg acgactcctc gaagcctggc ccccacccca aggcttccag tgaggacgaa | 1320 |
| gctccagggg gccagggcaa aaggggccaa agtccccaac ctgaccaggg gccctga | 1377 |

<210> SEQ ID NO 2
<211> LENGTH: 1188
<212> TYPE: DNA
<213> ORGANISM: Homo sapiens

<400> SEQUENCE: 2

| | |
|---|---|
| atggccacca ataaggagag actctttgcg cccggtgccc tggggcctgg atctggttac | 60 |
| ccaggagcag gcttcccatt cgccttccca ggtgcactca gagggtcgcc accatttgag | 120 |
| atgctgagcc ctagcttccg gggcctgggc cagcctgacc tccccaagga gatggcttct | 180 |
| ctctcggtgg agacacagag caccagctcg gaggagatgg tacccagctc tccctcaccc | 240 |
| ccaccacctc ctcgggtcta taagccatgc tttgtatgca atgacaagtc ttctggctac | 300 |
| cactatgggg tcagctcctg tgaaggctgc aagggcttct tcagacgcag cattcagaaa | 360 |
| aacatggtgt atacatgtca ccgtgacaaa aactgtatca tcaacaaggt caccagaaat | 420 |
| cgatgccagt actgcaggct acaaaagtgt ttcgaagtgg gcatgtccaa ggaagctgta | 480 |
| aggaacgatc gaaacaagaa gaaaaaggag gtaaaagagg agggctcgcc cgacagctat | 540 |
| gaactgagtc cacagttaga ggaactcatc accaaggtca gcaaagccca ccaggagact | 600 |
| tttcccctcac tctgccagct gggcaagtac accacgaact ccagtgcaga tcaccgggtg | 660 |
| cagctggacc tggggctgtg ggacaagttc agcgagctgg ccaccaaatg catcatcaag | 720 |
| attgtggagt ttgcgaagcg gctgcctggt tttacagggc tcagcattgc cgaccagatc | 780 |
| acgctgctca aggctgcttg tctggacatc ctaatgctgc ggatctgtac aaggtatacc | 840 |
| ccagagcagg acactatgac attctcggat gggctgaccc tgaaccgaac ccagatgcac | 900 |
| aatgctggct ttgggcccct tacagacctc gtctttgcct ttgccgggca gctgctgccc | 960 |
| ctggagatgg atgacaccga gactgggcta cttagtgcta tctgcctcat ctgtggagac | 1020 |
| cgaatggacc tggaagagcc cgagaaggtg gacaagctgc aggagcccct gctggaagcc | 1080 |
| ctgaggctct atgccggcg acggagaccc agccaaccct acatgttccc aaggatgctg | 1140 |
| atgaaaatca ccgacctccg gggcatcagc actaagggat gatgatga | 1188 |

<210> SEQ ID NO 3
<211> LENGTH: 200
<212> TYPE: DNA
<213> ORGANISM: Mus musculus

<400> SEQUENCE: 3

| | |
|---|---|
| tcccaccccc acagtctgc tcctccaccc acccaggggg cggggccaga ggtcaaggct | 60 |
| agagggtggg attggggagg gagaggtgaa accgtcccta ggtgagccgt ctttccacca | 120 |

```
ggccccggc tcggggtgcc caccttcccc atggctggac acctggcttc agacttcgcc    180
ttctcacccc caccaggtgg                                                200

<210> SEQ ID NO 4
<211> LENGTH: 191
<212> TYPE: DNA
<213> ORGANISM: Rattus norvegicus

<400> SEQUENCE: 4
tacccccact gctctactcc tccacccacc caggggggcgg ggccagaggt caaggctaga    60
gggtgggatt ggggagggag agaggtgcat aggtgagtcg tccttccacc aggccccgg    120 ctcggggagc ccaccttccc catggctgga cacctggctt cagacttcgc cttctcaccc    180
ccacctggtg g                                                        191

<210> SEQ ID NO 5
<211> LENGTH: 200
<212> TYPE: DNA
<213> ORGANISM: Sus barbatus

<400> SEQUENCE: 5
accccacccg acccctcccc cacccatcca gggggcgggg ccagaggtca aggctagtgg    60
gtgggattgg ggagggagag aggtgtcgag cagtcccctt ggagagccct ggttttactg   120 ggccccggc ttgggcgcc ttccttcccc atggcgggac acctggcttc cgacttcgcc    180
ttctcgcccc cgccgggcgg                                                200

<210> SEQ ID NO 6
<211> LENGTH: 200
<212> TYPE: DNA
<213> ORGANISM: Bos taurus

<400> SEQUENCE: 6
acccccacgg tcccttcccc ccacccatcc aggggggcggg gccagaggtc aaggctagtg    60
ggtgggattg gggagggaga gaggtgttga gcagtctcta ggagatccct cgttttccta   120 ggccccggc tcggggtgcc ttccttcccc atggcgggac acctcgcttc tgacttcgcc    180
ttctcgcccc cgccgggcgg                                                200

<210> SEQ ID NO 7
<211> LENGTH: 200
<212> TYPE: DNA
<213> ORGANISM: Gorilla gorilla

<400> SEQUENCE: 7 tcccccacc tccctctcct ccacccatcc aggggggcggg gccagaggtc aaggctagtg    60
ggtgggactg gggagggaga gagggttga gtagtccctt cgcaagccct catttcacca   120 ggccccggc ttgggcgcc ttccttcccc atggcgggac acctggcttc ggatttcgcc    180
ttctcgcccc ctccaggtgg                                                200

<210> SEQ ID NO 8
<211> LENGTH: 98
<212> TYPE: DNA
<213> ORGANISM: Pan troglodytes

<400> SEQUENCE: 8 tcccccacc tccctctcct ccacccatcc aggggggcggg gccagaggtc aaggctagtg    60
```

```
ggtgggactg gggagggaga gaggggttga gtagtccc                              98
```

<210> SEQ ID NO 9
<211> LENGTH: 200
<212> TYPE: DNA
<213> ORGANISM: Homo sapiens

<400> SEQUENCE: 9

```
tcccccacc  tccctctcct  ccacccatcc  aggggggcggg gccagaggtc aaggctagtg   60
ggtgggactg gggagggaga gaggggttga gtagtccctt cgcaagccct catttcacca    120
ggccccggc  ttggggcgcc ttccttcccc atggcgggac acctggcttc agatttcgcc   180
ttctcgcccc ctccaggtgg                                                 200
```

<210> SEQ ID NO 10
<211> LENGTH: 61
<212> TYPE: DNA
<213> ORGANISM: Artificial Sequence
<220> FEATURE:
<223> OTHER INFORMATION: Splinkerette adaptor HMSpAa

<400> SEQUENCE: 10

```
cgaagagtaa ccgttgctag gagagaccgt ggctgaatga gactggtgtc gacactagtg    60
g                                                                     61
```

<210> SEQ ID NO 11
<211> LENGTH: 48
<212> TYPE: DNA
<213> ORGANISM: Artificial Sequence
<220> FEATURE:
<223> OTHER INFORMATION: Splinkerette adaptor HMSpBb-Sau3A1

<400> SEQUENCE: 11

```
gatcccacta gtgtcgacac cagtctctaa tttttttttt caaaaaaa                  48
```

<210> SEQ ID NO 12
<211> LENGTH: 28
<212> TYPE: DNA
<213> ORGANISM: Artificial Sequence
<220> FEATURE:
<223> OTHER INFORMATION: 1st round PCR primer HMSp1

<400> SEQUENCE: 12

```
cgaagagtaa ccgttgctag gagagacc                                         28
```

<210> SEQ ID NO 13
<211> LENGTH: 25
<212> TYPE: DNA
<213> ORGANISM: Artificial Sequence
<220> FEATURE:
<223> OTHER INFORMATION: 2nd round PCR primer - HMSp2

<400> SEQUENCE: 13

```
gtggctgaat gagactggtg tcgac                                            25
```

<210> SEQ ID NO 14
<211> LENGTH: 25
<212> TYPE: DNA
<213> ORGANISM: Artificial Sequence
<220> FEATURE:
<223> OTHER INFORMATION: Sequencing primers HMSp3

<400> SEQUENCE: 14

```
gcgctttact cgacctaaac tttaa                                            25
```

<210> SEQ ID NO 15
<211> LENGTH: 30
<212> TYPE: DNA
<213> ORGANISM: Artificial Sequence
<220> FEATURE:
<223> OTHER INFORMATION: 1st round PCR primers, used together with
      HMSp1 - PB-L-Sp1

<400> SEQUENCE: 15
cctcgatata cagaccgata aaacacatgc                                      30

<210> SEQ ID NO 16
<211> LENGTH: 30
<212> TYPE: DNA
<213> ORGANISM: Artificial Sequence
<220> FEATURE:
<223> OTHER INFORMATION: 2nd round PCR primers, used together with
      HMSp2 - PB-L-Sp2

<400> SEQUENCE: 16
gagagagcaa tatttcaaga atgcatgcgt                                      30

<210> SEQ ID NO 17
<211> LENGTH: 25
<212> TYPE: DNA
<213> ORGANISM: Artificial Sequence
<220> FEATURE:
<223> OTHER INFORMATION: Sequencing Primer - PB-L-Sp3

<400> SEQUENCE: 17
gcgctttact cgacctaaac tttaa                                           25

<210> SEQ ID NO 18
<211> LENGTH: 30
<212> TYPE: DNA
<213> ORGANISM: Artificial Sequence
<220> FEATURE:
<223> OTHER INFORMATION: 1st round PCR primers, used together with
      HMSp1 - PB-R-Sp1

<400> SEQUENCE: 18
cctcgatata cagaccgata aaacacatgc                                      30

<210> SEQ ID NO 19
<211> LENGTH: 30
<212> TYPE: DNA
<213> ORGANISM: Artificial Sequence
<220> FEATURE:
<223> OTHER INFORMATION: 2nd round PCR primers, used together with
      HMSp2 - PB-R-Sp3

<400> SEQUENCE: 19
acgcatgatt atctttaacg tacgtcacaa                                      30

<210> SEQ ID NO 20
<211> LENGTH: 26
<212> TYPE: DNA
<213> ORGANISM: Artificial Sequence
<220> FEATURE:
<223> OTHER INFORMATION: Sequencing Primer

<400> SEQUENCE: 20
cgtcacaata tgattatctt tctagg                                          26

<210> SEQ ID NO 21

<211> LENGTH: 34
<212> TYPE: DNA
<213> ORGANISM: Artificial Sequence
<220> FEATURE:
<223> OTHER INFORMATION: mOct4-F-BglII Primer

<400> SEQUENCE: 21
gaagatctct ccaccttccc catggctgga cacc                    34

<210> SEQ ID NO 22
<211> LENGTH: 33
<212> TYPE: DNA
<213> ORGANISM: Artificial Sequence
<220> FEATURE:
<223> OTHER INFORMATION: mOct4-R-EcoRI Primer

<400> SEQUENCE: 22
cggaattctt gatcaacagc atcactgagc ttc                     33

<210> SEQ ID NO 23
<211> LENGTH: 31
<212> TYPE: DNA
<213> ORGANISM: Artificial Sequence
<220> FEATURE:
<223> OTHER INFORMATION: mSox2-F-BglII Primer

<400> SEQUENCE: 23
gaagatctct tgtataacat gatggagacg g                       31

<210> SEQ ID NO 24
<211> LENGTH: 32
<212> TYPE: DNA
<213> ORGANISM: Artificial Sequence
<220> FEATURE:
<223> OTHER INFORMATION: mSox2-R-EcoRI Primer

<400> SEQUENCE: 24
cggaattctt tcacatgtgc gacaggggca gt                      32

<210> SEQ ID NO 25
<211> LENGTH: 36
<212> TYPE: DNA
<213> ORGANISM: Artificial Sequence
<220> FEATURE:
<223> OTHER INFORMATION: mKlf4-F-BglII Primer

<400> SEQUENCE: 25
gaagatctca ccatggctgt cagcgacgct ctgctc                  36

<210> SEQ ID NO 26
<211> LENGTH: 32
<212> TYPE: DNA
<213> ORGANISM: Artificial Sequence
<220> FEATURE:
<223> OTHER INFORMATION: mKlf4-R-EcoRI Primer

<400> SEQUENCE: 26
cggaattcac atccactacg tgggatttaa aa                      32

<210> SEQ ID NO 27
<211> LENGTH: 36
<212> TYPE: DNA
<213> ORGANISM: Artificial Sequence
<220> FEATURE:
<223> OTHER INFORMATION: mcMyc-F-BglII Primer

<400> SEQUENCE: 27
gaagatctca ccatgcccct caacgtgaac ttcacc                           36

<210> SEQ ID NO 28
<211> LENGTH: 36
<212> TYPE: DNA
<213> ORGANISM: Artificial Sequence
<220> FEATURE:
<223> OTHER INFORMATION: mcMyc-R-EcoRI Primer

<400> SEQUENCE: 28
cggaattctt atgcaccaga gtttcgaagc tgttcg                           36

<210> SEQ ID NO 29
<211> LENGTH: 28
<212> TYPE: DNA
<213> ORGANISM: Artificial Sequence
<220> FEATURE:
<223> OTHER INFORMATION: mRarg-FL/DN-F-EcoRI

<400> SEQUENCE: 29
gggaattccc gcagctacca tggccacc                                    28

<210> SEQ ID NO 30
<211> LENGTH: 34
<212> TYPE: DNA
<213> ORGANISM: Artificial Sequence
<220> FEATURE:
<223> OTHER INFORMATION: mRarg-DN-R-XbaI

<400> SEQUENCE: 30
gctctagatc atcatcatcc cttagtgctg atgc                             34

<210> SEQ ID NO 31
<211> LENGTH: 27
<212> TYPE: DNA
<213> ORGANISM: Artificial Sequence
<220> FEATURE:
<223> OTHER INFORMATION: mRarg-FL-R-XbaI Primer

<400> SEQUENCE: 31
gctctagagc ccaaccccac aacgggg                                     27

<210> SEQ ID NO 32
<211> LENGTH: 28
<212> TYPE: DNA
<213> ORGANISM: Artificial Sequence
<220> FEATURE:
<223> OTHER INFORMATION: mRara-FL/DN-F-EcoRI Primer

<400> SEQUENCE: 32
gggaattcgc tgcttggcat ggccagca                                    28

<210> SEQ ID NO 33
<211> LENGTH: 35
<212> TYPE: DNA
<213> ORGANISM: Artificial Sequence
<220> FEATURE:
<223> OTHER INFORMATION: mRara-DN-R-XbaI Primer

<400> SEQUENCE: 33
gctctagatc atcatcatgg gatctccatc ttcaa                            35

<210> SEQ ID NO 34
<211> LENGTH: 30
<212> TYPE: DNA

```
<213> ORGANISM: Artificial Sequence
<220> FEATURE:
<223> OTHER INFORMATION: mRara-FL-R-XbaI Primer

<400> SEQUENCE: 34
gctctagagt gtcgaggtgg tcatggggat                                     30

<210> SEQ ID NO 35
<211> LENGTH: 32
<212> TYPE: DNA
<213> ORGANISM: Artificial Sequence
<220> FEATURE:
<223> OTHER INFORMATION: mSf1-F-EcoRI Primer

<400> SEQUENCE: 35
gggaattccc gcgggcatgg actattcgta cg                                  32

<210> SEQ ID NO 36
<211> LENGTH: 32
<212> TYPE: DNA
<213> ORGANISM: Artificial Sequence
<220> FEATURE:
<223> OTHER INFORMATION: mSf1-R-XbaI Primer

<400> SEQUENCE: 36
gctctagagg cacccaggct caagtctgct tg                                  32

<210> SEQ ID NO 37
<211> LENGTH: 35
<212> TYPE: DNA
<213> ORGANISM: Artificial Sequence
<220> FEATURE:
<223> OTHER INFORMATION: mLrh1-F-EcoRI Primer

<400> SEQUENCE: 37
gggaattctt tcgctaagaa tgtctgctag tttgg                               35

<210> SEQ ID NO 38
<211> LENGTH: 33
<212> TYPE: DNA
<213> ORGANISM: Artificial Sequence
<220> FEATURE:
<223> OTHER INFORMATION: mLrh1-R-XbaI Primer

<400> SEQUENCE: 38
gctctagagg ggacttaggc tcttttggca tgc                                 33

<210> SEQ ID NO 39
<211> LENGTH: 34
<212> TYPE: DNA
<213> ORGANISM: Artificial Sequence
<220> FEATURE:
<223> OTHER INFORMATION: hOCT4-F-EcoRI Primer

<400> SEQUENCE: 39
gggaattcca ccatggcggg acacctggct tcag                                34

<210> SEQ ID NO 40
<211> LENGTH: 34
<212> TYPE: DNA
<213> ORGANISM: Artificial Sequence
<220> FEATURE:
<223> OTHER INFORMATION: hOCT4-R-XbaI Primer

<400> SEQUENCE: 40
gctctagaac ctcagtttga atgcatggga gagc                                34
```

<210> SEQ ID NO 41
<211> LENGTH: 39
<212> TYPE: DNA
<213> ORGANISM: Artificial Sequence
<220> FEATURE:
<223> OTHER INFORMATION: hSOX2-F-EcoRI Primer

<400> SEQUENCE: 41
gggaattcca ccatgtacaa catgatggag acggagctg                      39

<210> SEQ ID NO 42
<211> LENGTH: 34
<212> TYPE: DNA
<213> ORGANISM: Artificial Sequence
<220> FEATURE:
<223> OTHER INFORMATION: hSOX2-R-XbaI Primer

<400> SEQUENCE: 42
gctctagatc acatgtgtga gaggggcagt gtgc                           34

<210> SEQ ID NO 43
<211> LENGTH: 38
<212> TYPE: DNA
<213> ORGANISM: Artificial Sequence
<220> FEATURE:
<223> OTHER INFORMATION: hKLF4-F-EcoRI Primer

<400> SEQUENCE: 43
gggaattcca ccatggctgt cagtgacgcg ctgctccc                       38

<210> SEQ ID NO 44
<211> LENGTH: 38
<212> TYPE: DNA
<213> ORGANISM: Artificial Sequence
<220> FEATURE:
<223> OTHER INFORMATION: hKLF4-R-XbaI Primer

<400> SEQUENCE: 44
gctctagatt aaaaatgtct cttcatgtgt aaggcgag                       38

<210> SEQ ID NO 45
<211> LENGTH: 38
<212> TYPE: DNA
<213> ORGANISM: Artificial Sequence
<220> FEATURE:
<223> OTHER INFORMATION: hCMYC-F-EcoRI Primer

<400> SEQUENCE: 45
gggaattcca ccatgcccct caacgttagc ttcaccaa                       38

<210> SEQ ID NO 46
<211> LENGTH: 38
<212> TYPE: DNA
<213> ORGANISM: Artificial Sequence
<220> FEATURE:
<223> OTHER INFORMATION: hCMYC-R-XbaI Primer

<400> SEQUENCE: 46
gctctagatc acgcacaaga gttccgtagc tgttcaag                       38

<210> SEQ ID NO 47
<211> LENGTH: 33
<212> TYPE: DNA
<213> ORGANISM: Artificial Sequence
<220> FEATURE:

```
<223> OTHER INFORMATION: hLRH1-F-EcoRI Primer

<400> SEQUENCE: 47
gggaattcat gtcttctaat tcagatactg ggg                              33

<210> SEQ ID NO 48
<211> LENGTH: 30
<212> TYPE: DNA
<213> ORGANISM: Artificial Sequence
<220> FEATURE:
<223> OTHER INFORMATION: hLRH1-R-XbaI Primer

<400> SEQUENCE: 48
gctctagatt atgctctttt ggcatgcaac                                  30

<210> SEQ ID NO 49
<211> LENGTH: 28
<212> TYPE: DNA
<213> ORGANISM: Artificial Sequence
<220> FEATURE:
<223> OTHER INFORMATION: hRARG-F-EcoRI Primer

<400> SEQUENCE: 49
gggaattcat ggccaccaat aaggagcg                                    28

<210> SEQ ID NO 50
<211> LENGTH: 29
<212> TYPE: DNA
<213> ORGANISM: Artificial Sequence
<220> FEATURE:
<223> OTHER INFORMATION: hRARG-R-XbaI Primer

<400> SEQUENCE: 50
gctctagatc aggctgggga cttcaggcc                                   29

<210> SEQ ID NO 51
<211> LENGTH: 23
<212> TYPE: DNA
<213> ORGANISM: Artificial Sequence
<220> FEATURE:
<223> OTHER INFORMATION: mOct4-RT-En-F Primer

<400> SEQUENCE: 51
tctttccacc aggcccccgg ctc                                         23

<210> SEQ ID NO 52
<211> LENGTH: 23
<212> TYPE: DNA
<213> ORGANISM: Artificial Sequence
<220> FEATURE:
<223> OTHER INFORMATION: mOct4-RT-En-R Primer

<400> SEQUENCE: 52
tgcgggcgga catggggaga tcc                                         23

<210> SEQ ID NO 53
<211> LENGTH: 23
<212> TYPE: DNA
<213> ORGANISM: Artificial Sequence
<220> FEATURE:
<223> OTHER INFORMATION: mSox2-RT-En-F Primer

<400> SEQUENCE: 53
ttgccttaaa caagaccacg aaa                                         23
```

```
<210> SEQ ID NO 54
<211> LENGTH: 23
<212> TYPE: DNA
<213> ORGANISM: Artificial Sequence
<220> FEATURE:
<223> OTHER INFORMATION: mSox2-RT-En-R Primer

<400> SEQUENCE: 54
tagagctaga ctccgggcga tga                                              23

<210> SEQ ID NO 55
<211> LENGTH: 24
<212> TYPE: DNA
<213> ORGANISM: Artificial Sequence
<220> FEATURE:
<223> OTHER INFORMATION: mKlf4-RT-En-F Primer

<400> SEQUENCE: 55
gcgaactcac acaggcgaga aacc                                             24

<210> SEQ ID NO 56
<211> LENGTH: 23
<212> TYPE: DNA
<213> ORGANISM: Artificial Sequence
<220> FEATURE:
<223> OTHER INFORMATION: mKlf4-RT-En-R Primer

<400> SEQUENCE: 56
tcgcttcctc ttcctccgac aca                                              23

<210> SEQ ID NO 57
<211> LENGTH: 20
<212> TYPE: DNA
<213> ORGANISM: Artificial Sequence
<220> FEATURE:
<223> OTHER INFORMATION: mNanog-RT-En-F Primer

<400> SEQUENCE: 57
caggtgtttg agggtagctc                                                  20

<210> SEQ ID NO 58
<211> LENGTH: 20
<212> TYPE: DNA
<213> ORGANISM: Artificial Sequence
<220> FEATURE:
<223> OTHER INFORMATION: mNanog-RT-En-R Primer

<400> SEQUENCE: 58
cggttcatca tggtacagtc                                                  20

<210> SEQ ID NO 59
<211> LENGTH: 24
<212> TYPE: DNA
<213> ORGANISM: Artificial Sequence
<220> FEATURE:
<223> OTHER INFORMATION: mRex1-RT-F Primer

<400> SEQUENCE: 59
acgagtggca gtttcttctt ggga                                             24

<210> SEQ ID NO 60
<211> LENGTH: 24
<212> TYPE: DNA
<213> ORGANISM: Artificial Sequence
<220> FEATURE:
<223> OTHER INFORMATION: mRex1-RT-R Primer
```

```
<400> SEQUENCE: 60
tatgactcac ttccaggggg cact                                          24

<210> SEQ ID NO 61
<211> LENGTH: 24
<212> TYPE: DNA
<213> ORGANISM: Artificial Sequence
<220> FEATURE:
<223> OTHER INFORMATION: mEsg1-RT-F Primer

<400> SEQUENCE: 61
gaagtctggt tccttggcag gatg                                          24

<210> SEQ ID NO 62
<211> LENGTH: 20
<212> TYPE: DNA
<213> ORGANISM: Artificial Sequence
<220> FEATURE:
<223> OTHER INFORMATION: mEsg1-RT-R Primer

<400> SEQUENCE: 62
actcgataca ctggcctagc                                               20

<210> SEQ ID NO 63
<211> LENGTH: 23
<212> TYPE: DNA
<213> ORGANISM: Artificial Sequence
<220> FEATURE:
<223> OTHER INFORMATION: mFgf4-RT-F Primer

<400> SEQUENCE: 63
cgtggtgagc atcttcggag tgg                                           23

<210> SEQ ID NO 64
<211> LENGTH: 23
<212> TYPE: DNA
<213> ORGANISM: Artificial Sequence
<220> FEATURE:
<223> OTHER INFORMATION: mFgf4-RT-R Primer

<400> SEQUENCE: 64
ccttcttggt ccgcccgttc tta                                           23

<210> SEQ ID NO 65
<211> LENGTH: 24
<212> TYPE: DNA
<213> ORGANISM: Artificial Sequence
<220> FEATURE:
<223> OTHER INFORMATION: mDax1-RT-F Primer

<400> SEQUENCE: 65
tgctgcggtc caggccatca agag                                          24

<210> SEQ ID NO 66
<211> LENGTH: 24
<212> TYPE: DNA
<213> ORGANISM: Artificial Sequence
<220> FEATURE:
<223> OTHER INFORMATION: mDax1-RT-R Primer

<400> SEQUENCE: 66
gggcactgtt cagttcagcg gatc                                          24

<210> SEQ ID NO 67
<211> LENGTH: 24
```

```
<212> TYPE: DNA
<213> ORGANISM: Artificial Sequence
<220> FEATURE:
<223> OTHER INFORMATION: mGdf3-RT-F primer

<400> SEQUENCE: 67
gttccaacct gtgcctcgcg tctt                                        24

<210> SEQ ID NO 68
<211> LENGTH: 26
<212> TYPE: DNA
<213> ORGANISM: Artificial Sequence
<220> FEATURE:
<223> OTHER INFORMATION: mGdf3-RT-R Primer

<400> SEQUENCE: 68
agcgaggcat ggagagagcg gagcag                                      26

<210> SEQ ID NO 69
<211> LENGTH: 23
<212> TYPE: DNA
<213> ORGANISM: Artificial Sequence
<220> FEATURE:
<223> OTHER INFORMATION: mUtf1-RT-F Primer

<400> SEQUENCE: 69
ggatgtcccg gtgactacgt ctg                                         23

<210> SEQ ID NO 70
<211> LENGTH: 23
<212> TYPE: DNA
<213> ORGANISM: Artificial Sequence
<220> FEATURE:
<223> OTHER INFORMATION: mUtf1-RT-R Primer

<400> SEQUENCE: 70
ggcggatctg gttatcgaag ggt                                         23

<210> SEQ ID NO 71
<211> LENGTH: 24
<212> TYPE: DNA
<213> ORGANISM: Artificial Sequence
<220> FEATURE:
<223> OTHER INFORMATION: mOct4-DMR-F2 Primer

<400> SEQUENCE: 71
tgggttgaaa tattgggttt attt                                        24

<210> SEQ ID NO 72
<211> LENGTH: 23
<212> TYPE: DNA
<213> ORGANISM: Artificial Sequence
<220> FEATURE:
<223> OTHER INFORMATION: mOct4-DMR-R2 Primer

<400> SEQUENCE: 72
ctaaaaccaa atatccaacc ata                                         23

<210> SEQ ID NO 73
<211> LENGTH: 30
<212> TYPE: DNA
<213> ORGANISM: Artificial Sequence
<220> FEATURE:
<223> OTHER INFORMATION: mNanog-DMR-F Primer

<400> SEQUENCE: 73
```
gattttgtag gtgggattaa ttgtgaattt         30

<210> SEQ ID NO 74
<211> LENGTH: 30
<212> TYPE: DNA
<213> ORGANISM: Artificial Sequence
<220> FEATURE:
<223> OTHER INFORMATION: mNanog-DMR-R Primer

<400> SEQUENCE: 74
accaaaaaaa cccacactca tatcaatata         30

<210> SEQ ID NO 75
<211> LENGTH: 30
<212> TYPE: DNA
<213> ORGANISM: Artificial Sequence
<220> FEATURE:
<223> OTHER INFORMATION: mNanog-DMR-R Primer

<400> SEQUENCE: 75
accaaaaaaa cccacactca tatcaatata         30

<210> SEQ ID NO 76
<211> LENGTH: 30
<212> TYPE: DNA
<213> ORGANISM: Artificial Sequence
<220> FEATURE:
<223> OTHER INFORMATION: mRex1-DMR-F2 Primer

<400> SEQUENCE: 76
tatattaatg ttggaaaaag tttaggtaat         30

<210> SEQ ID NO 77
<211> LENGTH: 30
<212> TYPE: DNA
<213> ORGANISM: Artificial Sequence
<220> FEATURE:
<223> OTHER INFORMATION: mRex1-DMR-R2 Primer

<400> SEQUENCE: 77
aactccttaa acccctccct ttttaaataa         30

<210> SEQ ID NO 78
<211> LENGTH: 24
<212> TYPE: DNA
<213> ORGANISM: Artificial Sequence
<220> FEATURE:
<223> OTHER INFORMATION: hOCT4-RT-endo-F Primer

<400> SEQUENCE: 78
gacaggggga ggggaggagc tagg         24

<210> SEQ ID NO 79
<211> LENGTH: 26
<212> TYPE: DNA
<213> ORGANISM: Artificial Sequence
<220> FEATURE:
<223> OTHER INFORMATION: hOCT4-RT-endo-R Primer

<400> SEQUENCE: 79
cttccctcca accagttgcc ccaaac         26

<210> SEQ ID NO 80
<211> LENGTH: 26
<212> TYPE: DNA
<213> ORGANISM: Artificial Sequence

```
<220> FEATURE:
<223> OTHER INFORMATION: hSOX2-RT-endo-F Primer

<400> SEQUENCE: 80
gggaaatggg aggggtgcaa aagagg                                          26

<210> SEQ ID NO 81
<211> LENGTH: 26
<212> TYPE: DNA
<213> ORGANISM: Artificial Sequence
<220> FEATURE:
<223> OTHER INFORMATION: hSOX2-RT-endo-R Primer

<400> SEQUENCE: 81
ttgcgtgagt gtggatggga ttggtg                                          26

<210> SEQ ID NO 82
<211> LENGTH: 25
<212> TYPE: DNA
<213> ORGANISM: Artificial Sequence
<220> FEATURE:
<223> OTHER INFORMATION: hKLF4-RT-endo-F Primer

<400> SEQUENCE: 82
acgatcgtgg ccccggaaaa ggacc                                           25

<210> SEQ ID NO 83
<211> LENGTH: 26
<212> TYPE: DNA
<213> ORGANISM: Artificial Sequence
<220> FEATURE:
<223> OTHER INFORMATION: hKLF4-RT-endo-R Primer

<400> SEQUENCE: 83
gcgtcctggg aagggagatc cggagc                                          26

<210> SEQ ID NO 84
<211> LENGTH: 26
<212> TYPE: DNA
<213> ORGANISM: Artificial Sequence
<220> FEATURE:
<223> OTHER INFORMATION: hCMYC-RT-endo-F Primer

<400> SEQUENCE: 84
gcgtcctggg aagggagatc cggagc                                          26

<210> SEQ ID NO 85
<211> LENGTH: 26
<212> TYPE: DNA
<213> ORGANISM: Artificial Sequence
<220> FEATURE:
<223> OTHER INFORMATION: hCMYC-RT-endo-R Primer

<400> SEQUENCE: 85
ttgaggggca tcgtcgcggg aggctg                                          26

<210> SEQ ID NO 86
<211> LENGTH: 25
<212> TYPE: DNA
<213> ORGANISM: Artificial Sequence
<220> FEATURE:
<223> OTHER INFORMATION: hNANOG-RT-F Primer

<400> SEQUENCE: 86
cagccccgat tcttccacca gtccc                                           25
```

```
<210> SEQ ID NO 87
<211> LENGTH: 25
<212> TYPE: DNA
<213> ORGANISM: Artificial Sequence
<220> FEATURE:
<223> OTHER INFORMATION: hNANOG-RT-R Primer

<400> SEQUENCE: 87
cggaagattc ccagtcgggt tcacc                                    25

<210> SEQ ID NO 88
<211> LENGTH: 24
<212> TYPE: DNA
<213> ORGANISM: Artificial Sequence
<220> FEATURE:
<223> OTHER INFORMATION: hREX1-RT-F Primer

<400> SEQUENCE: 88
cagatcctaa acagctcgca gaat                                     24

<210> SEQ ID NO 89
<211> LENGTH: 23
<212> TYPE: DNA
<213> ORGANISM: Artificial Sequence
<220> FEATURE:
<223> OTHER INFORMATION: hREX1-RT-R Primer

<400> SEQUENCE: 89
gcgtacgcaa attaaagtcc aga                                      23

<210> SEQ ID NO 90
<211> LENGTH: 26
<212> TYPE: DNA
<213> ORGANISM: Artificial Sequence
<220> FEATURE:
<223> OTHER INFORMATION: hTERT-RT-F Primer

<400> SEQUENCE: 90
cctgctcaag ctgactcgac accgtg                                   26

<210> SEQ ID NO 91
<211> LENGTH: 25
<212> TYPE: DNA
<213> ORGANISM: Artificial Sequence
<220> FEATURE:
<223> OTHER INFORMATION: hTERT-RT-R Primer

<400> SEQUENCE: 91
ggaaaagctg gccctggggt ggagc                                    25

<210> SEQ ID NO 92
<211> LENGTH: 25
<212> TYPE: DNA
<213> ORGANISM: Artificial Sequence
<220> FEATURE:
<223> OTHER INFORMATION: hDNMT3B-RT-F Primer

<400> SEQUENCE: 92
tgctgctcac agggcccgat acttc                                    25

<210> SEQ ID NO 93
<211> LENGTH: 28
<212> TYPE: DNA
<213> ORGANISM: Artificial Sequence
<220> FEATURE:
<223> OTHER INFORMATION: hDNMT3B-RT-R Primer
```

```
<400> SEQUENCE: 93
tcctttcgag ctcagtgcac cacaaaac                                    28

<210> SEQ ID NO 94
<211> LENGTH: 24
<212> TYPE: DNA
<213> ORGANISM: Artificial Sequence
<220> FEATURE:
<223> OTHER INFORMATION: hCMYC-taq-endo-F QPCR probe

<400> SEQUENCE: 94
cctgagcaat cacctatgaa cttg                                        24

<210> SEQ ID NO 95
<211> LENGTH: 22
<212> TYPE: DNA
<213> ORGANISM: Artificial Sequence
<220> FEATURE:
<223> OTHER INFORMATION: hCMYC-taq-endo-R QPCR Probe

<400> SEQUENCE: 95
ttatgcccaa agtccaattt ga                                          22

<210> SEQ ID NO 96
<211> LENGTH: 26
<212> TYPE: DNA
<213> ORGANISM: Artificial Sequence
<220> FEATURE:
<223> OTHER INFORMATION: hCMYC-taq-endo-probe

<400> SEQUENCE: 96
caaatgcaac ctcacaacct tggctg                                      26

<210> SEQ ID NO 97
<211> LENGTH: 22
<212> TYPE: DNA
<213> ORGANISM: Artificial Sequence
<220> FEATURE:
<223> OTHER INFORMATION: hKLF4-taq-endo-F probe

<400> SEQUENCE: 97
tttcacactg tcttcccgat ga                                          22

<210> SEQ ID NO 98
<211> LENGTH: 25
<212> TYPE: DNA
<213> ORGANISM: Artificial Sequence
<220> FEATURE:
<223> OTHER INFORMATION: hKLF4-taq-endo-R probe

<400> SEQUENCE: 98
tcctgattat ccactcacaa gatga                                       25

<210> SEQ ID NO 99
<211> LENGTH: 30
<212> TYPE: DNA
<213> ORGANISM: Artificial Sequence
<220> FEATURE:
<223> OTHER INFORMATION: hKLF4-taq-endo-probe

<400> SEQUENCE: 99
ccagccagaa agcactacaa tcatggtcaa                                  30

<210> SEQ ID NO 100
```

```
<211> LENGTH: 23
<212> TYPE: DNA
<213> ORGANISM: Artificial Sequence
<220> FEATURE:
<223> OTHER INFORMATION: hOCT4-taq-endo-F Probe

<400> SEQUENCE: 100
cactgtactc ctcggtccct ttc                                          23

<210> SEQ ID NO 101
<211> LENGTH: 20
<212> TYPE: DNA
<213> ORGANISM: Artificial Sequence
<220> FEATURE:
<223> OTHER INFORMATION: hOCT4-taq-endo-R Probe

<400> SEQUENCE: 101
caaccagttg ccccaaactc                                              20

<210> SEQ ID NO 102
<211> LENGTH: 26
<212> TYPE: DNA
<213> ORGANISM: Artificial Sequence
<220> FEATURE:
<223> OTHER INFORMATION: hOCT4-taq-endo-probe

<400> SEQUENCE: 102
ctttccccct gtctccgtca ccactc                                       26

<210> SEQ ID NO 103
<211> LENGTH: 21
<212> TYPE: DNA
<213> ORGANISM: Artificial Sequence
<220> FEATURE:
<223> OTHER INFORMATION: hSOX2-taq-endo-F Probe

<400> SEQUENCE: 103
acagcaaatg acagctgcaa a                                            21

<210> SEQ ID NO 104
<211> LENGTH: 28
<212> TYPE: DNA
<213> ORGANISM: Artificial Sequence
<220> FEATURE:
<223> OTHER INFORMATION: hSOX2-taq-endo-R Probe

<400> SEQUENCE: 104
aagtccagga tctctctcat aaaagttt                                     28

<210> SEQ ID NO 105
<211> LENGTH: 24
<212> TYPE: DNA
<213> ORGANISM: Artificial Sequence
<220> FEATURE:
<223> OTHER INFORMATION: hSOX2-taq-endo-probe

<400> SEQUENCE: 105
atccacactc acgcaaaaac cgcg                                         24

<210> SEQ ID NO 106
<211> LENGTH: 26
<212> TYPE: DNA
<213> ORGANISM: Artificial Sequence
<220> FEATURE:
<223> OTHER INFORMATION: hLRH1-taq-endo-F probe

<400> SEQUENCE: 106
```

```
aaagctgaac tgaaacaatt ctcaag                                              26

<210> SEQ ID NO 107
<211> LENGTH: 18
<212> TYPE: DNA
<213> ORGANISM: Artificial Sequence
<220> FEATURE:
<223> OTHER INFORMATION: hLRH1-taq-endo-R Probe

<400> SEQUENCE: 107
gctcgggcct tcaaagga                                                       18

<210> SEQ ID NO 108
<211> LENGTH: 30
<212> TYPE: DNA
<213> ORGANISM: Artificial Sequence
<220> FEATURE:
<223> OTHER INFORMATION: hLRH1-taq-endo-probe

<400> SEQUENCE: 108
tgcatcagct gtacctacaa tagcccctcc                                          30

<210> SEQ ID NO 109
<211> LENGTH: 22
<212> TYPE: DNA
<213> ORGANISM: Artificial Sequence
<220> FEATURE:
<223> OTHER INFORMATION: hRARG-taq-endo-F Probe

<400> SEQUENCE: 109
gagcctgggt ttggactcta aa                                                  22

<210> SEQ ID NO 110
<211> LENGTH: 20
<212> TYPE: DNA
<213> ORGANISM: Artificial Sequence
<220> FEATURE:
<223> OTHER INFORMATION: hRARG-taq-endo-R probe

<400> SEQUENCE: 110
cctcttgccc tgggaagtct                                                     20

<210> SEQ ID NO 111
<211> LENGTH: 22
<212> TYPE: DNA
<213> ORGANISM: Artificial Sequence
<220> FEATURE:
<223> OTHER INFORMATION: hRARG-taq-endo-probe

<400> SEQUENCE: 111
ctcagcactg ccccatgggt cc                                                  22
```

CELLS AND METHODS FOR OBTAINING THEM

CROSS-REFERENCE TO RELATED APPLICATIONS

This application is a national stage filing of PCT/GB2010/051493, filed Sep. 7, 2010, which claims priority to Great Britain application no. GB 0915523.5 filed Sep. 7, 2009, U.S. Provisional application 61/240,282, filed Sep. 7, 2009 and U.S. Provisional application 61/276,203, filed Sep. 8, 2009, each of which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: OLSW_014_02US_SeqList.txt, date recorded: Mar. 5, 2012, file size 26 kilobytes).

The present invention relates to reprogrammed somatic cells, methods for reprogramming, reprogramming factors for somatic cells, and uses of such factors and cells.

Mouse embryonic fibroblast cells (MEF) can be reprogrammed to a pluripotent state by expression of four transcription factors (Yamanaka factors), Oct4, Sox2, c-Myc and Klf4 (1-3). The same set of genes or its variants were later applied to reprogram somatic cells of a variety of lineages in the mouse (4-6), rat and human (7-9). Reprogramming of primary somatic cells to induced pluripotent stem cells (iPS) is a complex and gradual process accompanied with genetic and epigenetic changes (37, 51). Thus, mouse iPS clones produced by transgenic expression of four Yamanaka factors are often heterogeneous, with a mixture of fully and partially reprogrammed cells (52). Sustained expression of the exogenous factors is sometimes required in iPS cells for self-renewal and other important embryonic stem cell (ES)-like characteristics (51, 11). Therefore without a strong selection scheme to identify the fully reprogrammed cells, it has been proven difficult to establish germline-competent mouse iPS cell lines by simply continuous passaging and subcloning. Although human iPS cells are produced using various platforms based on Yamanaka factors, it is reasonable to predict that these cells might also be of a heterogeneous nature. Lacking of reliable reporters such as fluorescence or drug selection markers linked to endogenous pluripotent genes makes it difficult to isolate fully reprogrammed cells from a heterogeneous population of human iPS cells produced using the available reprogramming factors.

The current human ES cells derived from embryos are different from mouse ES cells in their morphology, gene expression patterns and clonogenicity (53, 44). The most obvious difference is that pluripotency of mouse ES cells depends on activation of Jak/Stat3 pathway by leukaemia inhibitory factor (LIF) (54) or inhibition of Mek/Erk pathway (40). In contrast, human ES cells are not responsive to LIF, and can only be maintained by FGF and activin (44). The recent derivation of mouse epiblast stem cells (EpiSC) using human ES cell culture condition (55, 56) indicates that human ES cells are likely analogous to mouse EpiSC in many aspects rather than to truly pluripotent mouse ES cells. The current lack of true human counterpart of mouse ES cells makes it difficult to prove whether a common paradigm governing ES cell pluripotency operates in other mammalian species. Moreover, from an application point of view, the availability of a human pluripotent stem cell line equivalent to mouse ES cells will make it a reality to apply the wealth of knowledge of mouse ES cell self-renewal, differentiation and genetic manipulation directly to human ES cells.

STATEMENTS OF INVENTION

In one aspect the invention provides a method for preparing an induced pluripotent stem cell by nuclear reprogramming of a somatic cell, which comprises a step of contacting the somatic cell with a nuclear reprogramming factor [NRF], the factor comprising one or more of:
  (i) a gene product from a retinoic acid receptor (RAR/RXR) family member, or an agonist or antagonist thereof;
  (ii) a gene product from an Lrh1 family member; or an agonist thereof;
  (iii) retinoic acid or a gene product involved in synthesizing or metabolizing retinoic acid; or an agonist or antagonist thereof;
  (iv) a gene product that is involved in transporting a retinoic acid family member
  (v) a polynucleic acid encoding a gene product of any of (i) to (iv) above.

In one aspect the method comprises using both (i) and (ii) above.

In one aspect, the invention relates to a method for reprogramming somatic cells into induced pluripotent cells comprising:
(a) contacting a somatic cell with a NRF which comprises, or is, is one or more of:
  (i) a gene product from a retinoic acid receptor (RAR/RXR) family member, or an agonist thereof;
  (ii) a gene product from an Lrh1 family member; or an agonist thereof
  (iii) retinoic acid or a gene product involved in synthesizing or metabolizing retinoic acid family member; or an agonist or antagonist thereof;
  (iv) a gene product that is involved in transporting a retinoic acid family member;
  (v) a polynucleic acid encoding a gene product of any of (i) to (iv) above;
  and then
(b) optionally checking to determine if the somatic cell has been reprogrammed, and
(c) contacting the product from step (a) with an antagonist of RA or RAR/RXR family member, or removing contact with the NRF, to maintain pluripotency.

In one aspect the invention provides an NRF comprising, one or more of:
  (i) a gene product from a retinoic acid receptor (RAR/RXR) family member, or or an agonist or antagonist thereof;
  (ii) a gene product from an Lrh1 family member; or an agonist thereof,
  (iii) a gene product from an Lrh1 family member;
  (iv) retinoic acid or a gene product involved in synthesizing or metabolizing retinoic acid; or an agonist or antagonist thereof;
  (v) a gene product that is involved in transporting a retinoic acid family member;
  (vi) a polynucleic acid encoding a gene product of any of (i) to (iv) above.

In one aspect the NRF is for reprogramming somatic cells into induced pluripotent cells.

In one aspect the invention provides an NRF comprising or encoding a gene product from an RAR family member and an Lrh1 family member.

In a further aspect the invention provides an NRF comprising or encoding a gene product from an RAR family member, an Lrh1 family member, an Oct family member and a Myc family member.

In a further aspect the invention provides a NRF comprising or encoding a gene product from an RAR family member, an Lrh1 family member, an Oct family member, a Klf family member, a Myc family member and a Sox family member.

In a further aspect of the invention the NRF comprises a vector or vectors comprising a nucleic acid/nucleic acids encoding a nuclear reprogramming factor or factors as described herein.

In a further aspect the invention provides an induced pluripotent stem cell, such as a human iPS, in one aspect obtained or obtainable by the methods disclosed herein.

In a further aspect the invention relates to an induced human pluripotent cell characterised by at least one of the following:
- expression of one or more pluripotency markers such as Oct4, Nanog, Rex1;
- growth independent of FGF;
- retain a normal karyotype as measured by using spectral karyotyping analysis after passaging;
- capable of forming teratomas when injected into mice;
- demethylation of promoter regions for one, or more of, Oct4, Nanog, Rex1;
- Cells can be dissociated to viable single cells capable of forming secondary colonies;
- proliferation in M15+hLIF media and/or 2i+LIF media In a yet further aspect the invention provides an induced pluripotent stem cell (iPS) wherein the iPS comprises an exogenous DNA sequence.

In a further aspect the invention provides a somatic cell derived by differentiation of an induced pluripotent stem cell of the invention.

In a further aspect the invention provides a cell the genome of which has been modified to allow for modulation of the expression of the nucleic acid encoding a retinoic acid receptor (RAR/RXR) family member, or a gene product from an Lrh1 family member.

In a further aspect the invention provides a tissue, or organ, or non-human animal derived from, or comprising, a somatic cell derived by differentiation of an induced pluripotent stem cell of the invention.

In a further aspect the invention provides a pharmaceutical composition comprising a nuclear reprogramming factor, vector or cell or tissue as described herein, in combination with a pharmaceutically acceptable excipient.

In a further aspect the invention provides use of a nuclear reprogramming factor, or iPS cell, or a somatic cell or tissue or organ derived from an iPS cell as described herein, in medicine, and use of a nuclear reprogramming factor, or iPS cell, or a somatic cell or tissue or organ derived from an iPS cell as described herein, in the preparation of a medicament for the treatment of a patient in need thereof.

In a further aspect the invention provides a method of preventing a disease or treating a disease in a patient in need thereof, the method comprising delivery to the patient a pharmaceutically acceptable amount of one of: a nuclear reprogramming factor, iPS cell, somatic cell, tissue or organ according to the present invention.

FIGURES

FIG. 1. shows RA signalling in reprogramming. A. Schematic of the reprogramming strategy by piggyBac (PB) transposition. B-C. Expressing Rara or Rarg, together with the four Yamanaka factors, drastically promoted reprogramming while inhibiting RA signalling by expressing Rara-DN blocked reprogramming. D. Temporal requirement of RA signalling in reprogramming. E-F. Expression of pluripotency genes (E) and DNA methylation at Nanog and Rex1 loci (F) in reprogrammed cells. G. Improvement of iPSC quality by Rarg agonist CD437.

Figure 2:
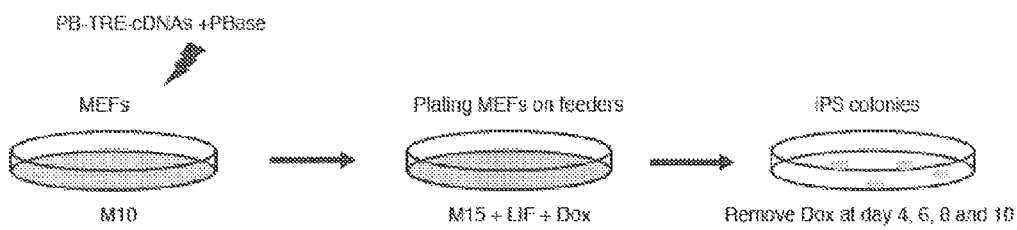
Figure 2:
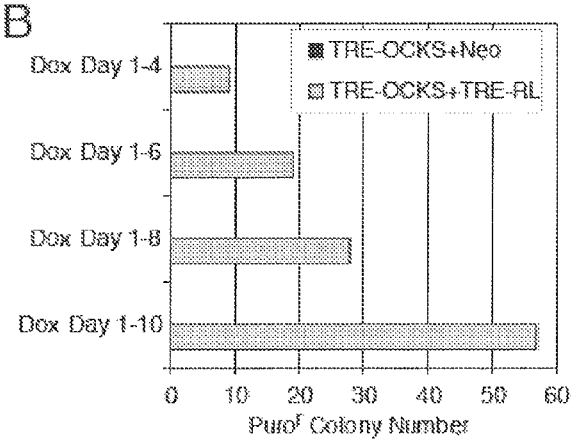
Figure 2:
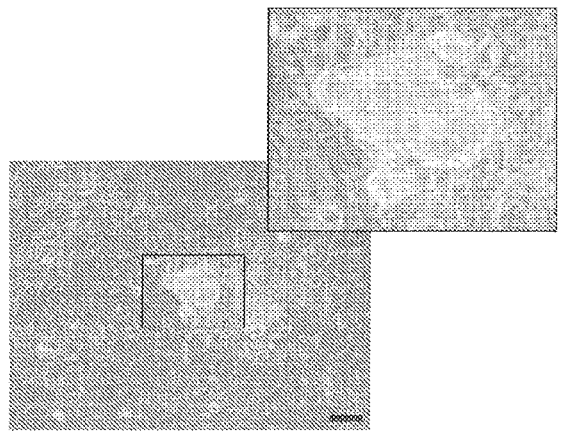
Figure 2:
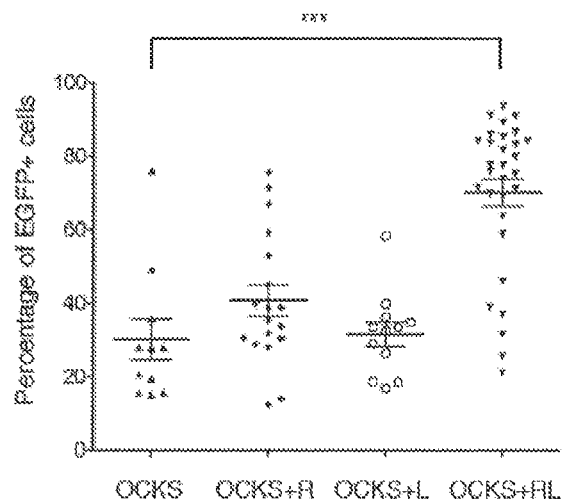
Figure 2:
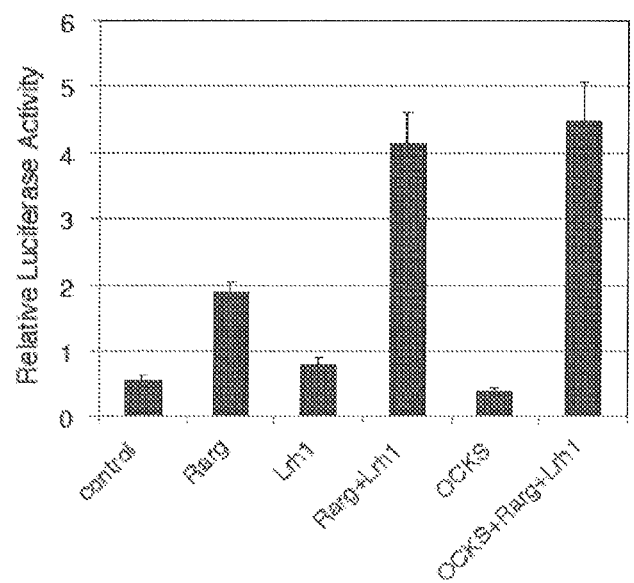

FIG. 2. Rarg (R) and Lrh-1 (L) synergistically promote reprogramming. A. Schematic of the Tet-On reprogramming strategy. B. Four-day expression of the six factors (TRE-OCKS and TRE-RL) was sufficient to fully activate endogenous Oct4 expression for obtaining Dox-independent iPSCs. C. Images of colonies 6 days post transfection. D. Co-expressing Rarg and Lrh-1 (RL), but not Rarg or Lrh-1 individually, improved iPSC quality.

Figure 3:
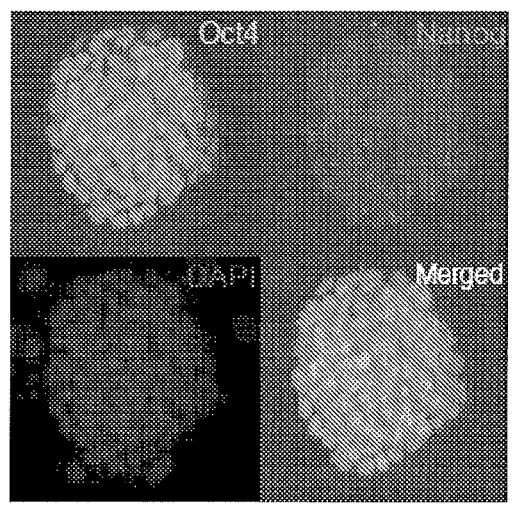
Figure 3:
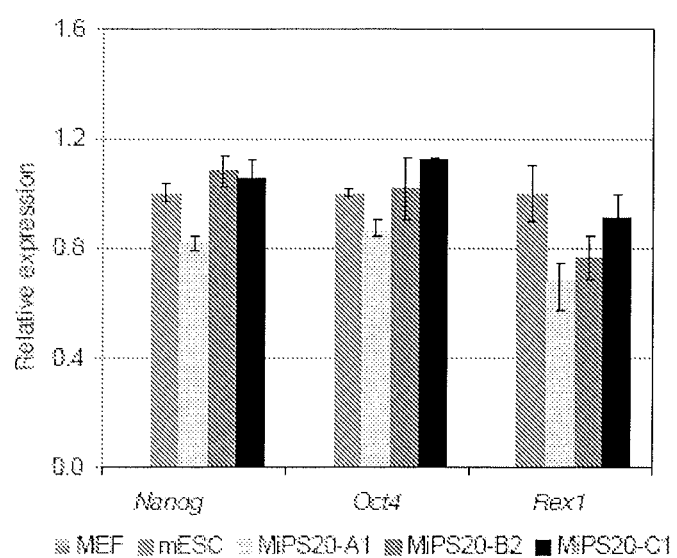
Figure 3:
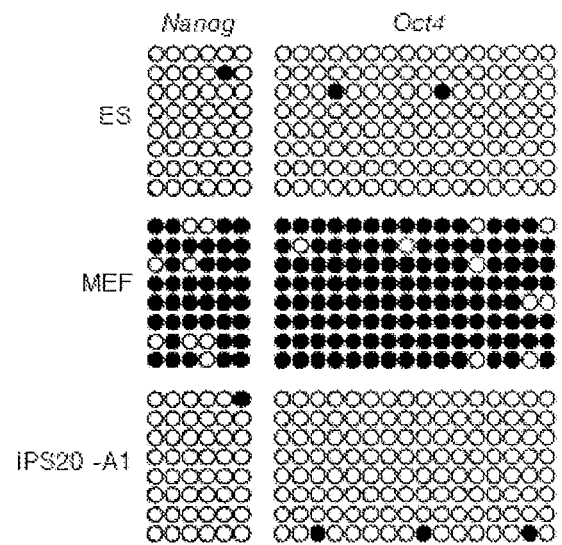
Figure 3:
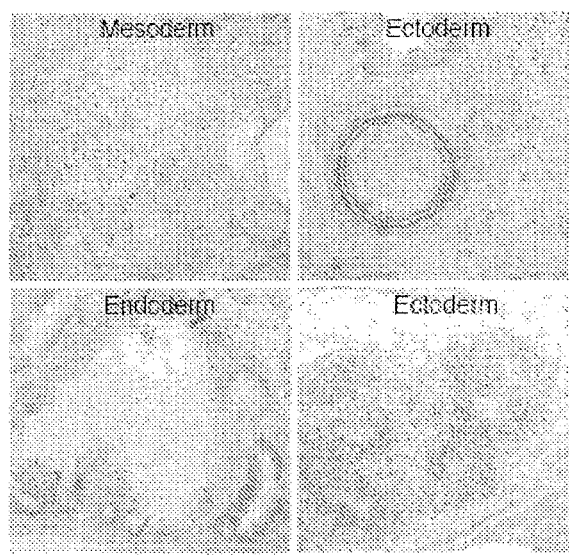
Figure 3:

FIG. 3. Characterization of Dox-independent mouse iPSCs. A. Immunostaining of iPS20-A1 cells to detect Oct4 and Nanog. B. qRT-PCR of Oct4, Nanog and Rex1 in mouse iPSCs, parental MEFs and wild type ES cells. C. Nearly complete de-methylation in the promoters of Oct4 and Nanog in the iPSCs (iPS20-A1). D. Teratomas derived from the iPSCs contained cells types of all three germ layers. E. Contribution of iPSCs to the germline in chimeras.

Figure 4:
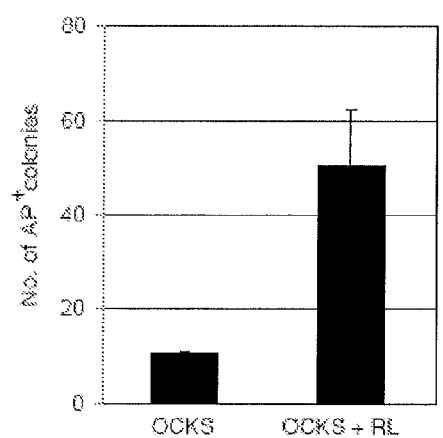
Figure 4:
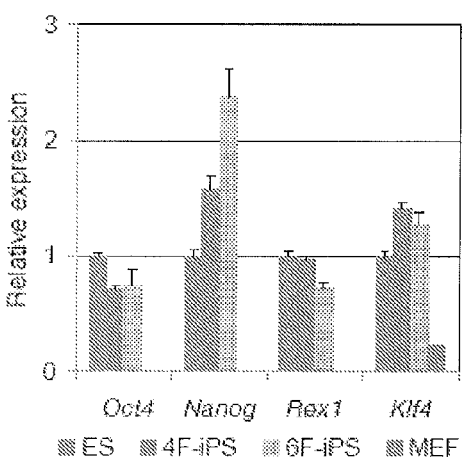
Figure 4:
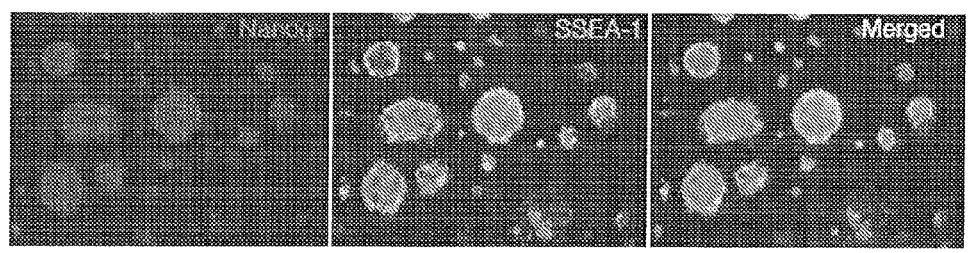
Figure 4:
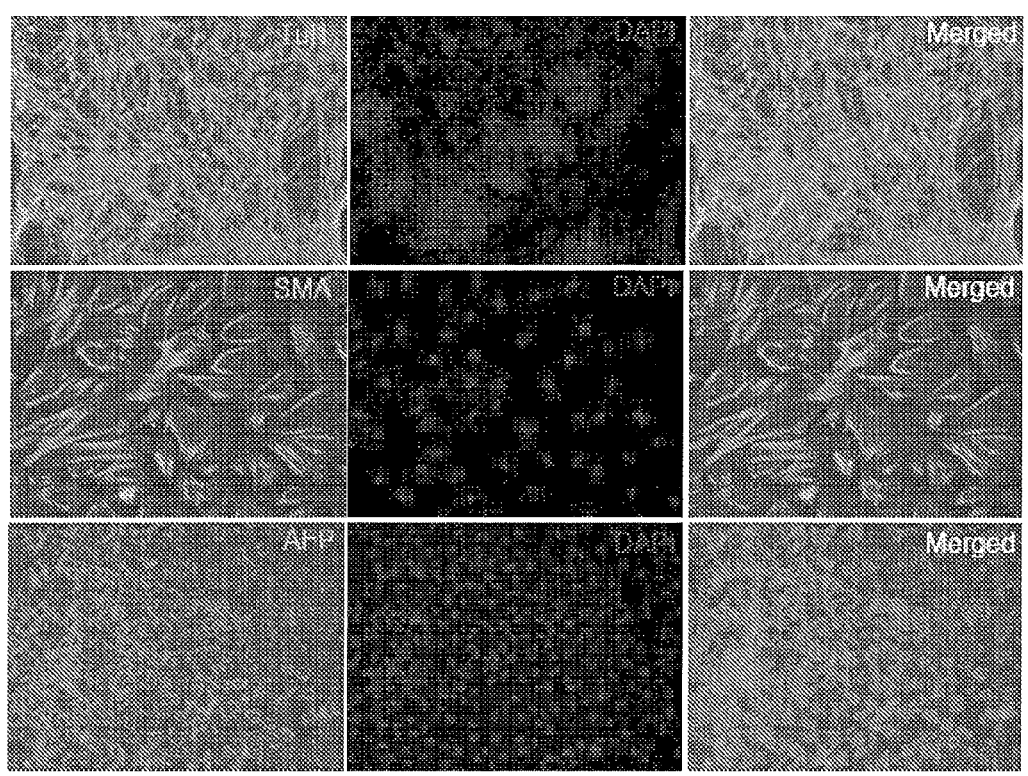

FIG. 4. Reprogramming MEFs to ground state iPSCs in serum-free, feeder-free conditions. A. Number of AP$^+$ colonies reprogrammed with either PB-TRE-OCKS (4F), or PB-TRE-OCKS plus PB-TRE-RL (6F). B. Gene expression analysis of iPSCs by qRT-PCR. C. Immunostaining of iPSCs (6F) for Nanog and SSEA-1 expression. D. In vitro differentiation of iPSCs (6F) to cell type representing the three germ layers detected by immunostaining.

Figure 5:
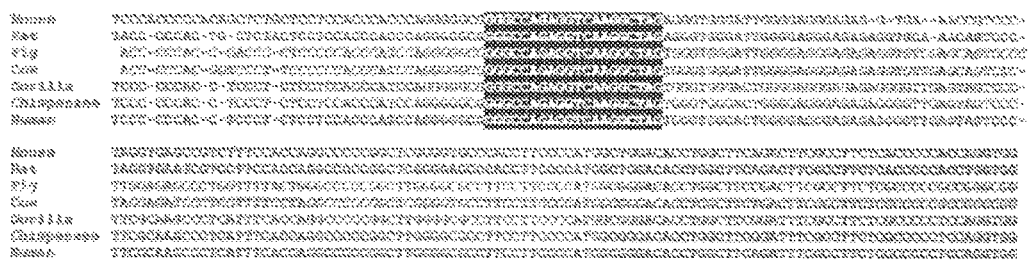
Figure 5:
Figure 5:
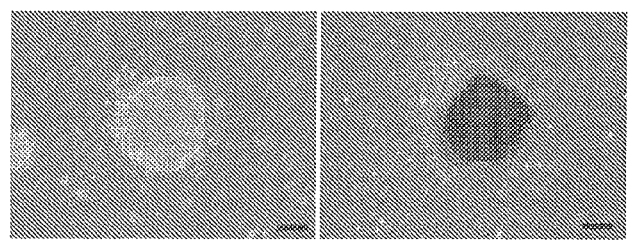
Figure 5:
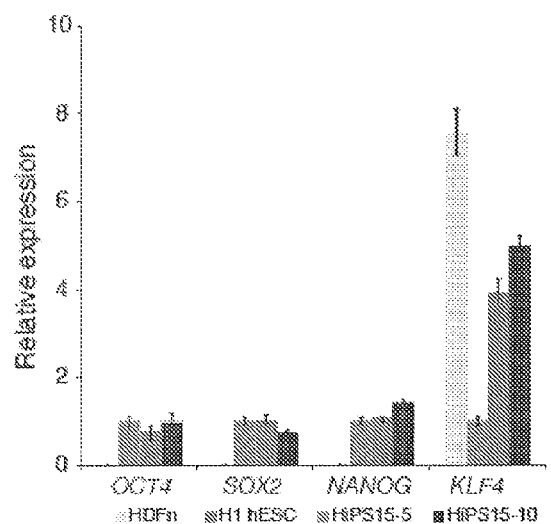
Figure 5:
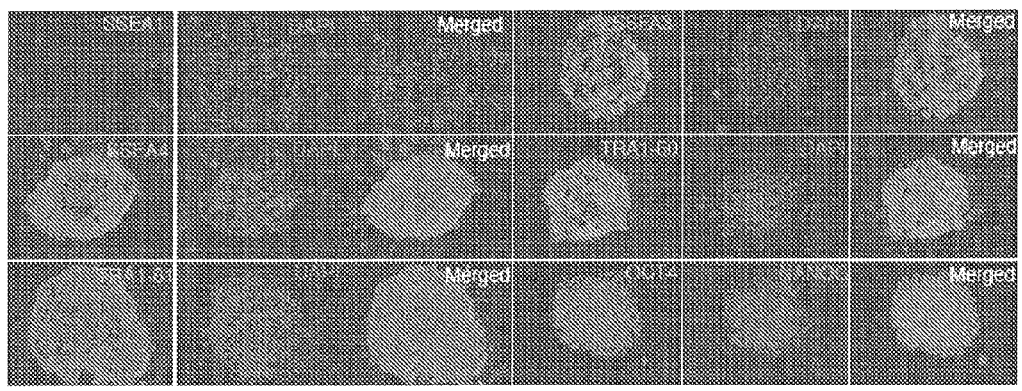
Figure 5:
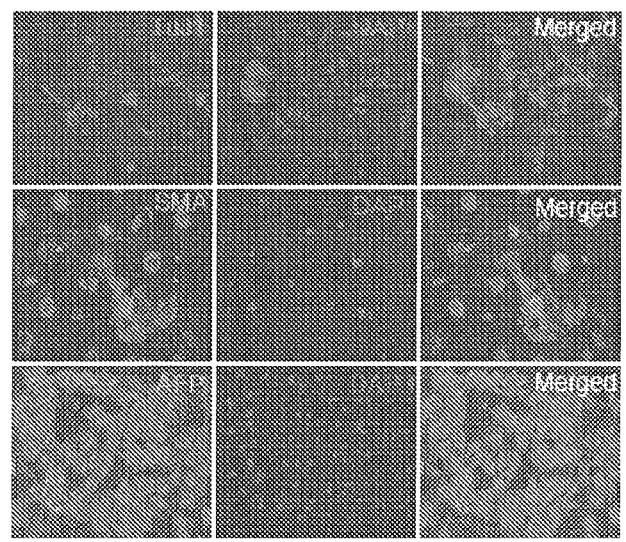
Figure 5:
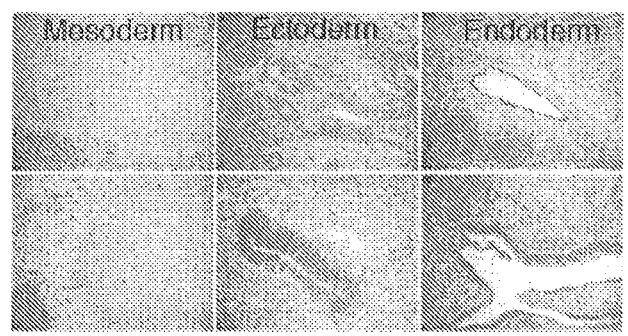
Figure 5:
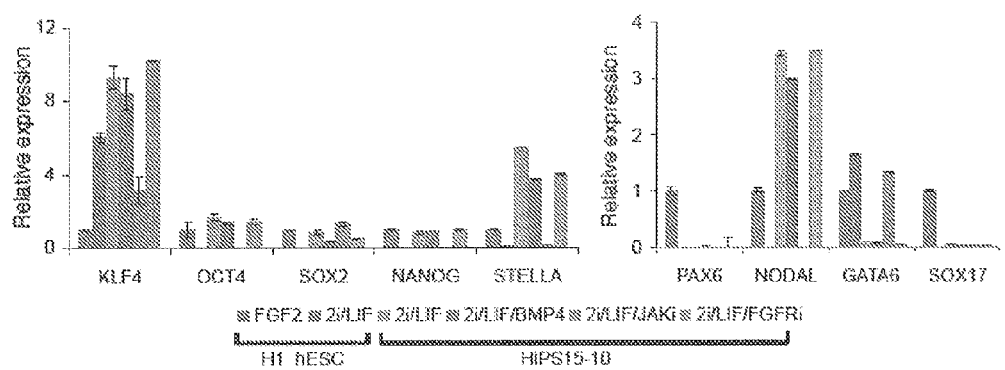
Figure 5:
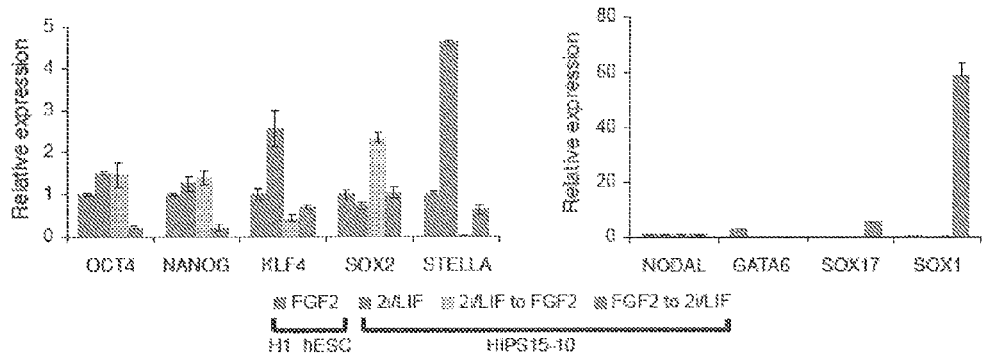

FIG. 5. Production and characterization of Dox-independent unique human iPSCs. A. Conservation of RAREoct sequence in several mammalian species. B. Reprogramming HDFn cells using the Tet-On six-factor platform. C. Typical human iPSC colony morphology and AP staining. D. qRT-PCR analysis of pluripotency genes in parental HDFn, human iPSCs and H1 hESC cells. E. Immunostaining of human iPSCs for ES cell surface markers and pluripotency factors. F. In vitro differentiation of human iPSCs. Antibodies. G. Teratomas differentiated from human iPSCs. H. Signalling dependency of human iPSCs measured by gene expression (qRT-PCR). I. Gene expression changes in human iPSCs growing in different conditions.

Figure 6:
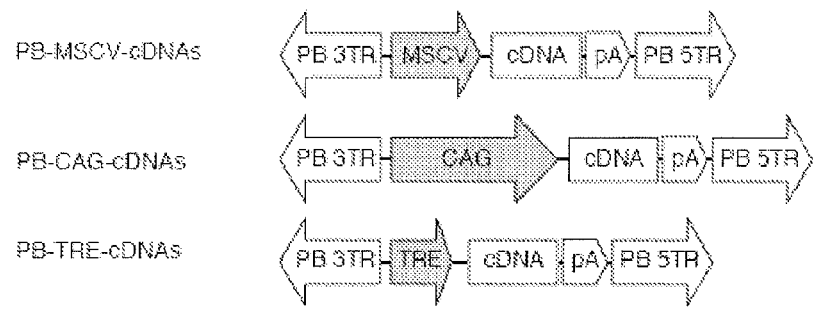
Figure 6:
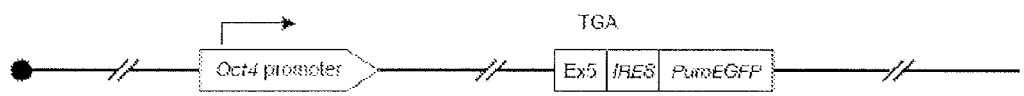
Figure 6:
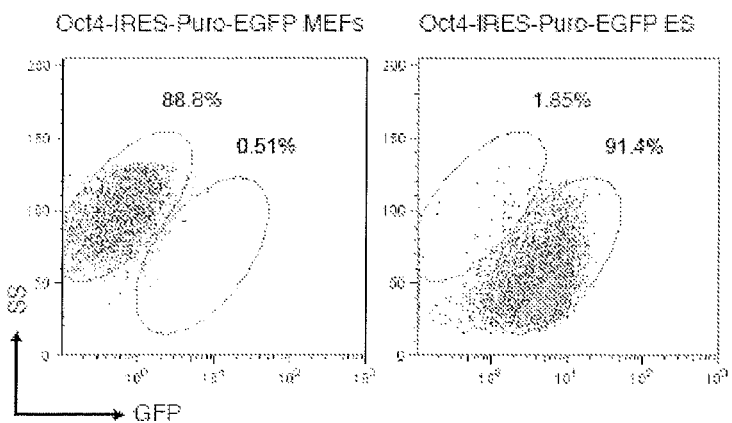
Figure 6:
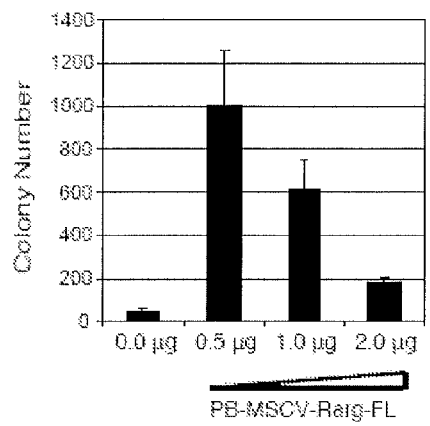
Figure 6:
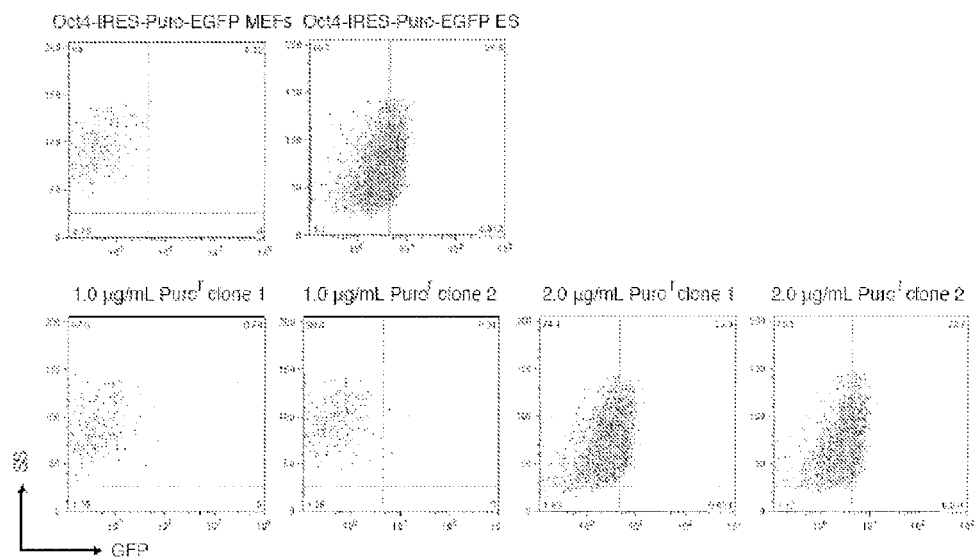

FIG. 6. A. PB transposons carrying transcription factor cDNAs. B. The Oct4-IRES-Puro-Egfp knock-in allele. C. Flow cytometric analysis of Oct4-IRES-Puro-Egfp MEF cells and Oct4-IRES-Puro-Egfp knock-in ES cells. D. Increased amount of Rarg-carrying transposon DNA in transfection reduced reprogramming efficiency of OCKS. E. Flow cytometric analysis of reprogrammed mouse cells survived two Puromycin concentrations.

Figure 7:
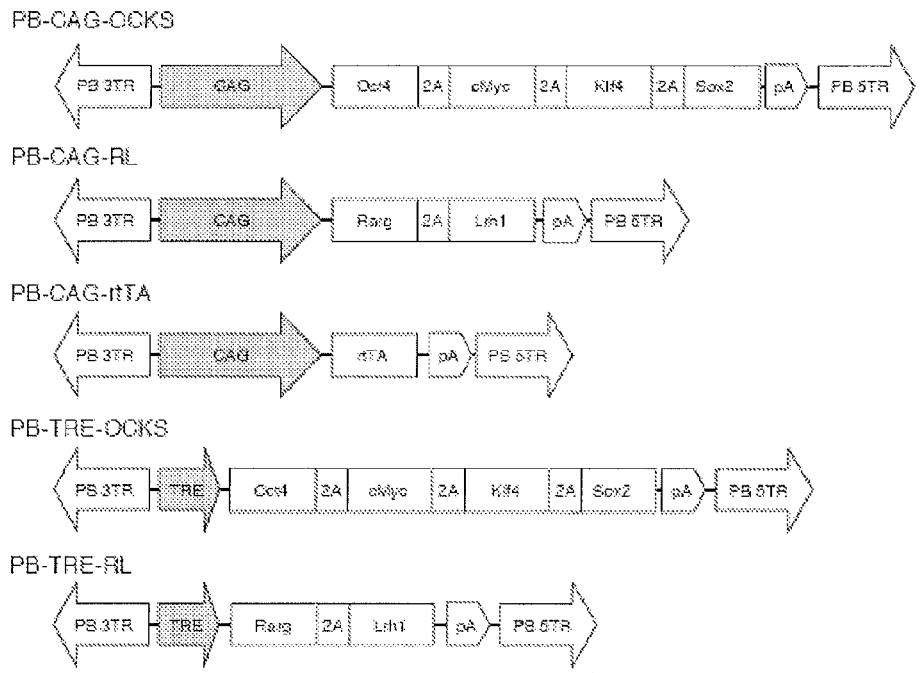
Figure 7:
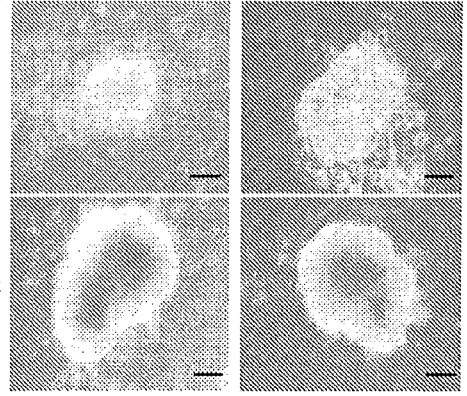
Figure 7:
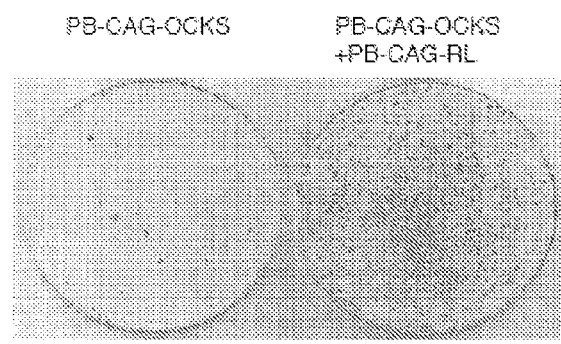
Figure 7:
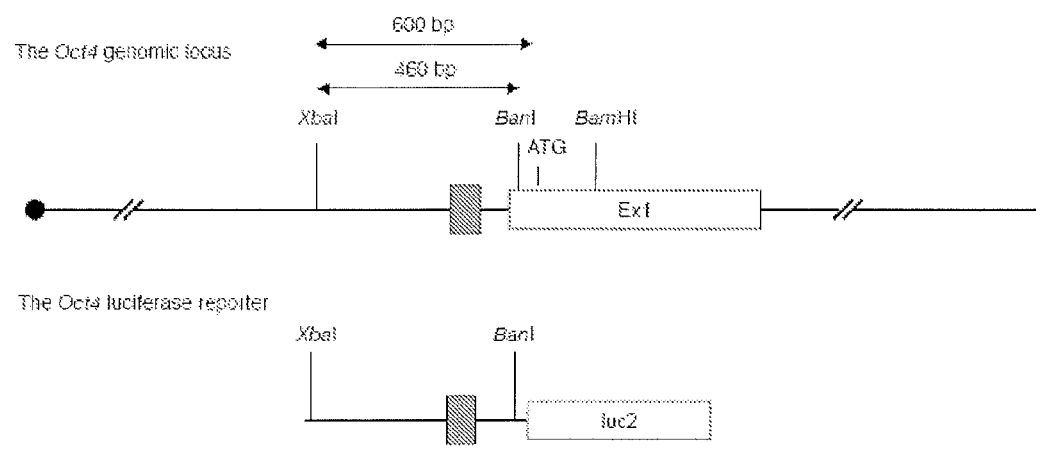

FIG. 7. Rarg and Lrh-1 synergistically promotes reprogramming. A. PB transposons carrying multiple cDNAs linked by the DNA encoding 2A, the foot-and-mouth disease virus 2A self-cleaving peptide. B. Typical iPSC colonies. C. Alkaline phosphatase staining of iPSC colonies 10 days after transfection. D. Diagram of the DNA construct for the luciferase reporter assay.

Figure 8:
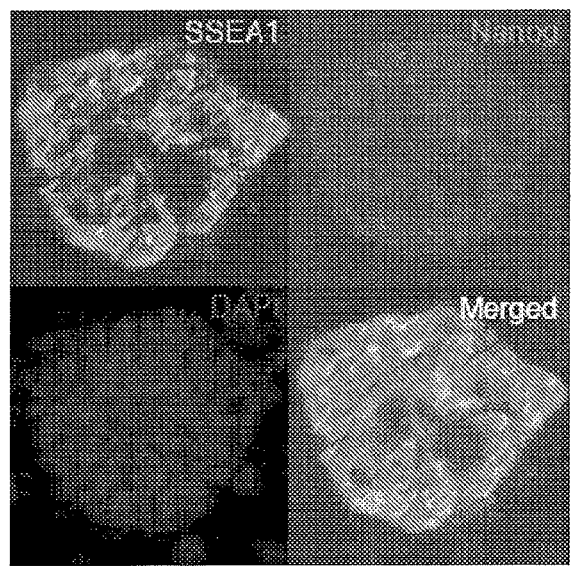
Figure 8:
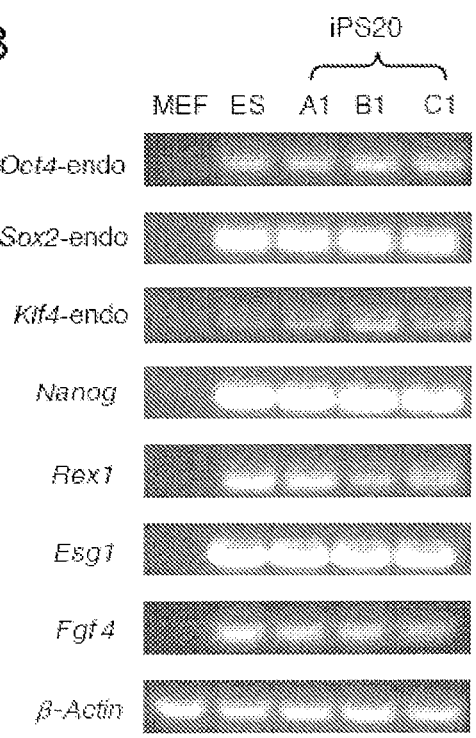
Figure 8:
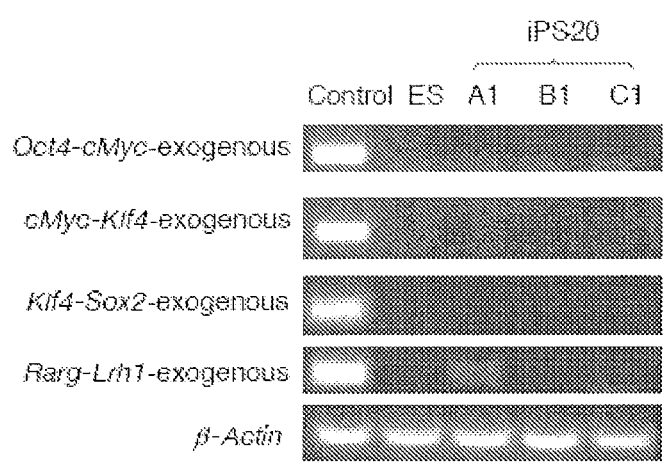

FIG. 8. Characterization of mouse iPSCs for pluripotency. A. Immunostaining of iPS20-A1 cells to detect SSEA1 and Nanog. B. Robust expression of endogenous pluripotency genes in mouse iPSCs. C. RT-PCR analysis of expression of the exogenous reprogramming factors in mouse iPSC lines.

Figure 9:
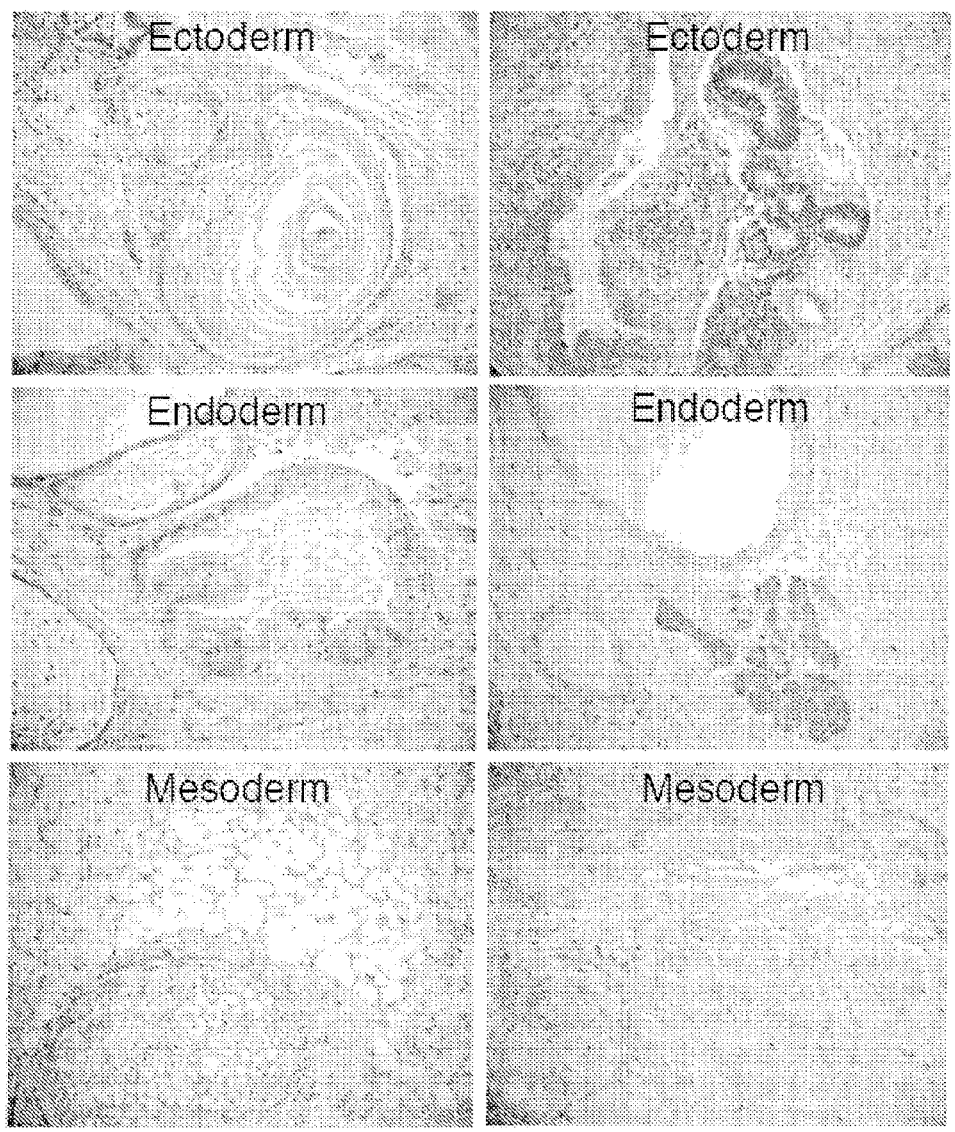

FIG. 9. Reprogramming of MEFs in the feeder-free and serum-free conditions. A. transfected MEFs B. Hematoxilin and eosin stained parafin sections of teratomas.

Figure 10:
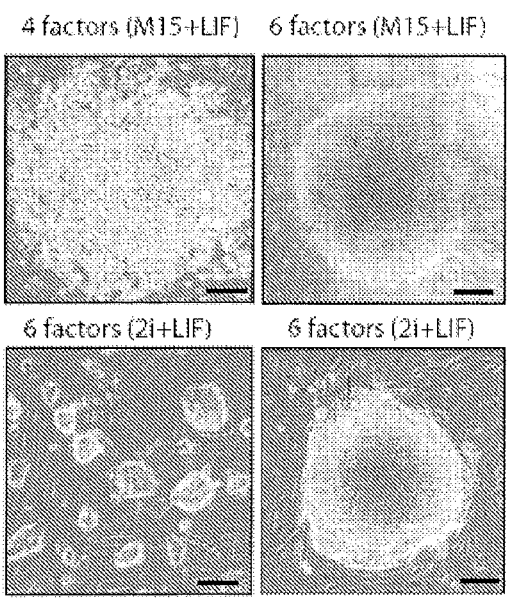
Figure 10:
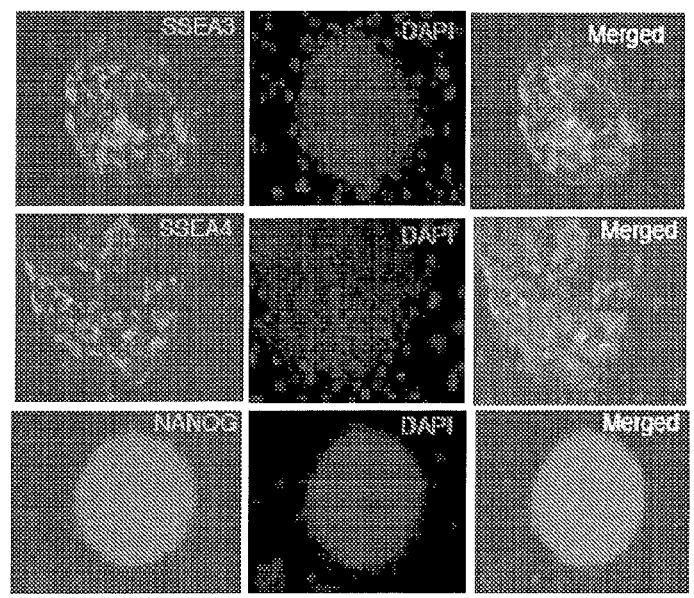
Figure 10:
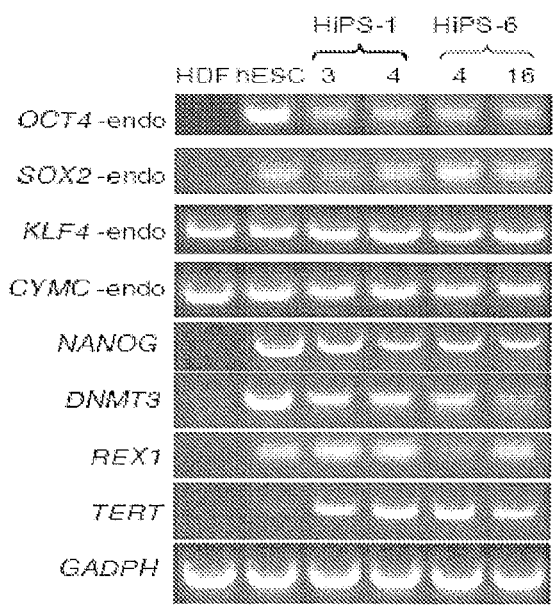
Figure 10:
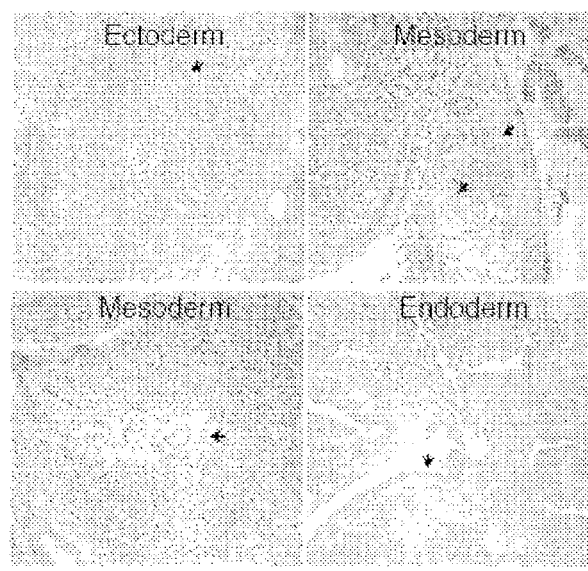
Figure 10:
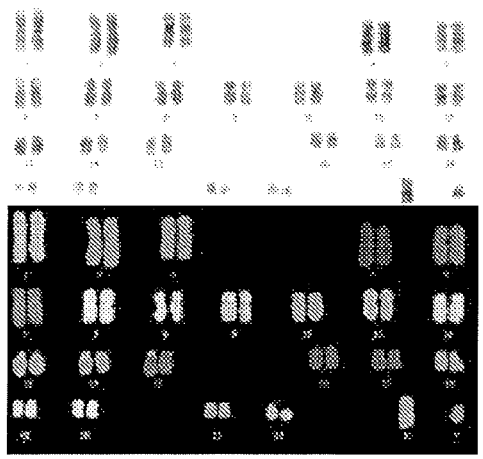
Figure 10:
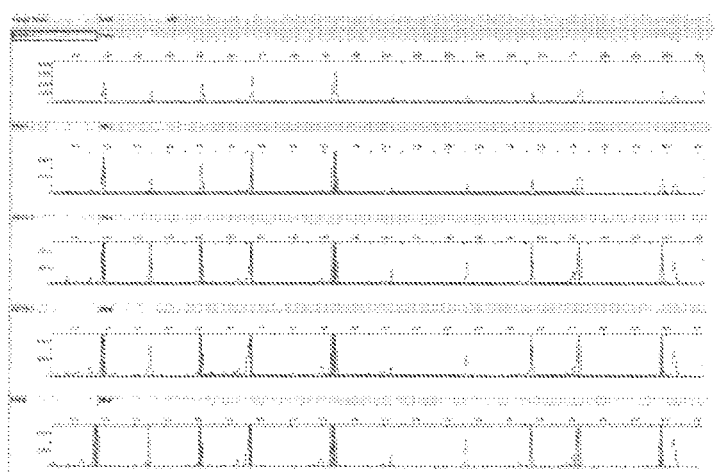

FIG. 10. Production of unique human iPSCs cells with the six-factor platform (CAG promoter version). A. Human iPSCs colonies formed in M15 plus LIF media or in 2i/LIF media, which resembled regular mouse ES cell colonies. B. Expression of endogenous pluripotency protein in human iPSCs detected by immuno-staining. C. Expression of pluripotency genes in human iPSCs detected by RT-PCR. D. Differentiation of human iPSCs to cell types of the three germ layers in teratomas. E. Normal karyotype in human iPSCs after extensive passaging (>20 passages). F. Y chromosome genotyping of human iPSCs confirmed the HDFn origin of human iPSCs.

Figure 11:
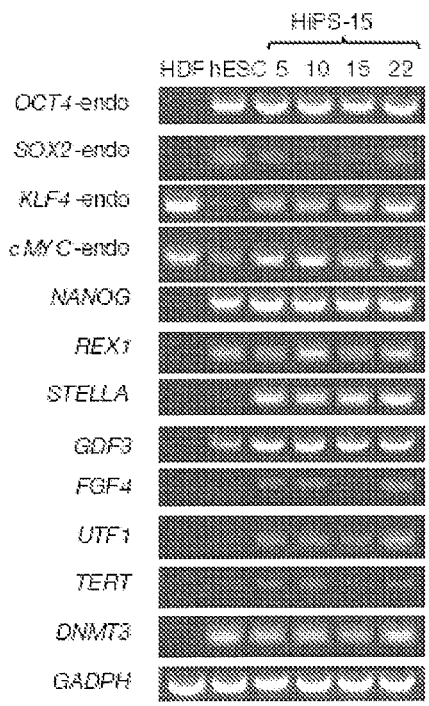
Figure 11:
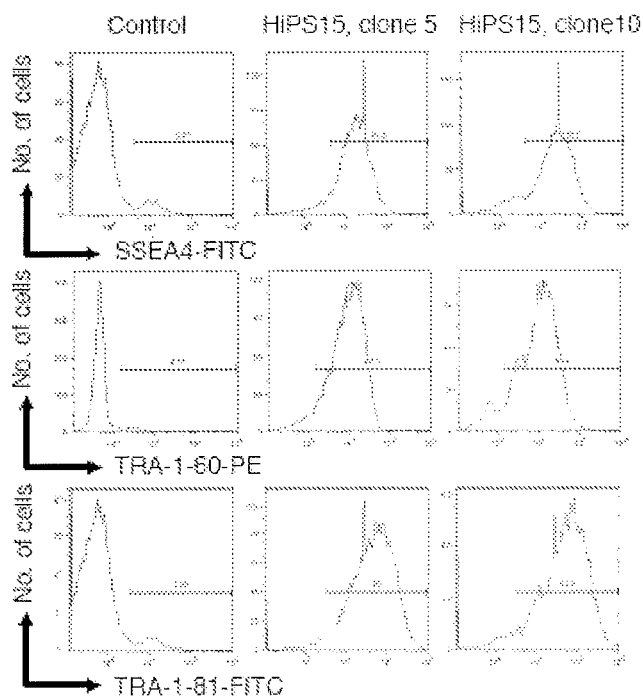
Figure 11:
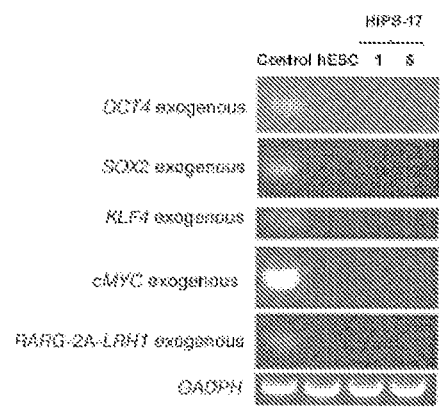
Figure 11:
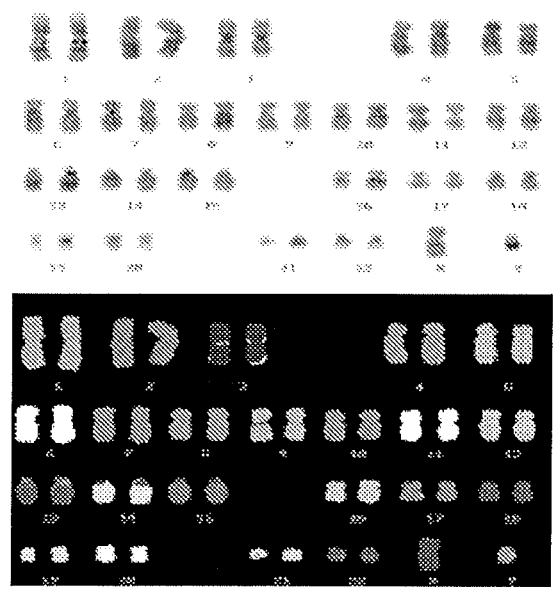
Figure 11:
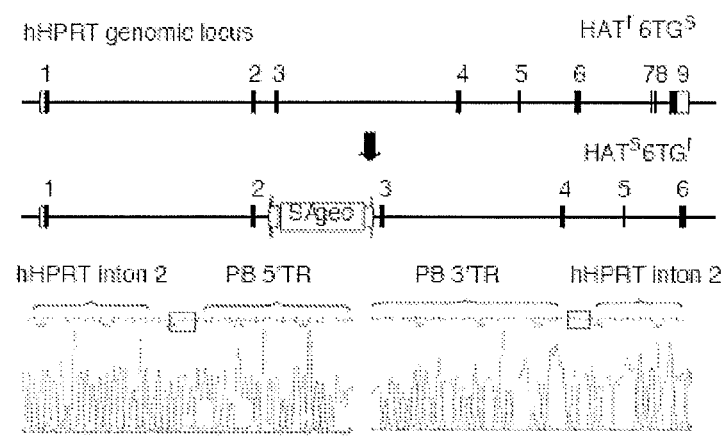

FIG. 11. Characterization of unique human iPSCs produced using the six-factor Tet-On system (Dox-independent). A. RT-PCR analysis of gene expression in human iPSCs. B. FACS analysis of human iPSCs for SSEA-4, Tra-1-60 and Tra-1-81 expression. C. RT-PCR analysis of reprogramming factor expression in human iPSCs showing no exogenous reprogramming factor expression. D. Human iPSCs had the normal karyotype after extensive in vitro culturing. E. Insertion of the gene-trap PB transposon into the HPRT locus.

Figure 12:
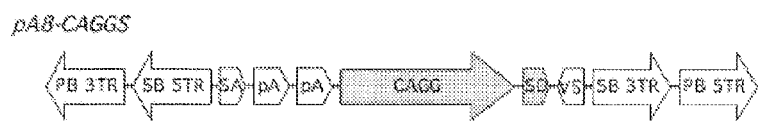
Figure 12:
Figure 12:
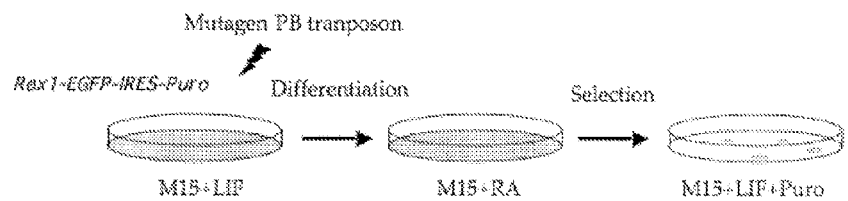
Figure 12:
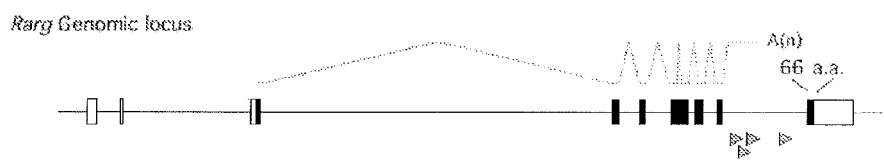
Figure 12:
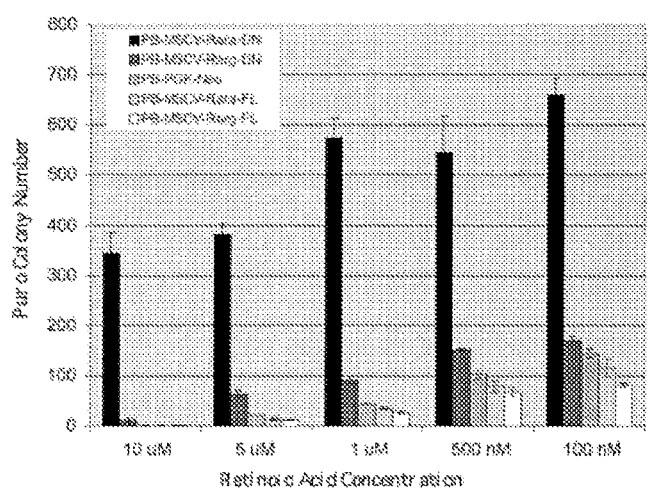
Figure 12:
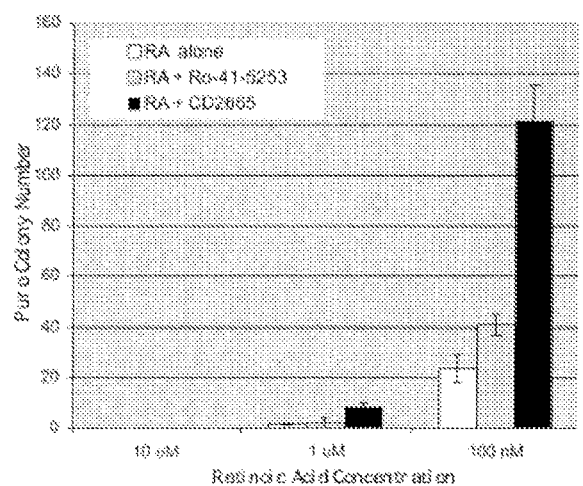

FIG. 12. A Rarg Dominant-negative Allele Blocks ES Cell Differentiation. A. Schematic of the PB transposon that carries both a strong CAG promoter/enhancer and a pair of splicing acceptors. B. Diagram of the Rex1-Puro-IRES-Egfp knock-in mouse ES cell line. C. Strategy of the genetic screen in mouse ES cells to identify mutants that can block ES cell differentiation induced by retinoic acid. D. Four independent mutations at the Rarg locus identified in the genetic screen. E. RA induced ES cell differentiation blocked by over-expression of Rarg or Rara dominant form. F. RA induced ES cell differentiation blocked by Rarg- or Rara-specific antagonists.

Figure 13:
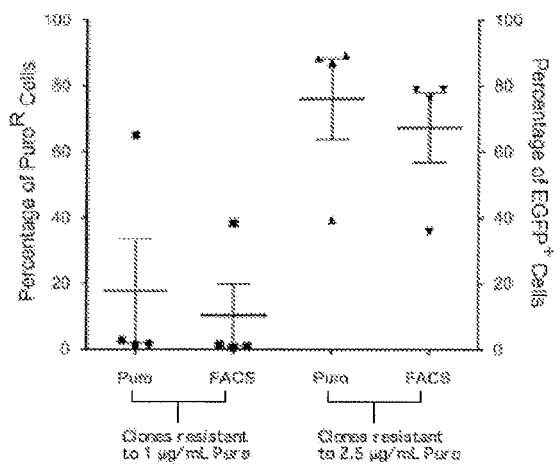
Figure 13:
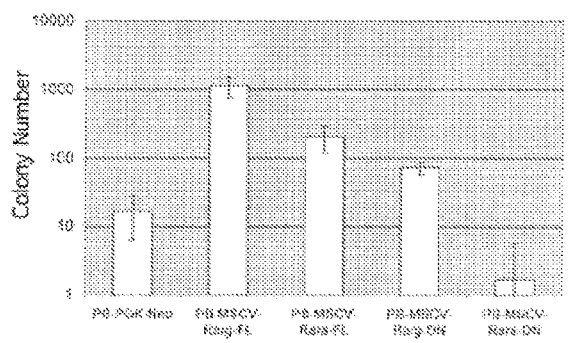
Figure 13:
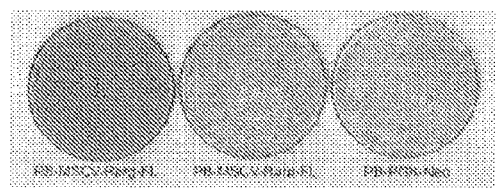
Figure 13:
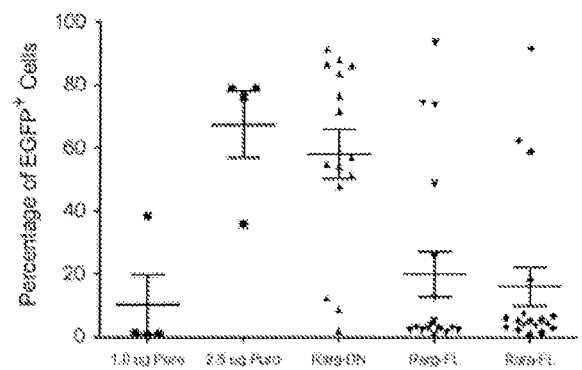
Figure 13:
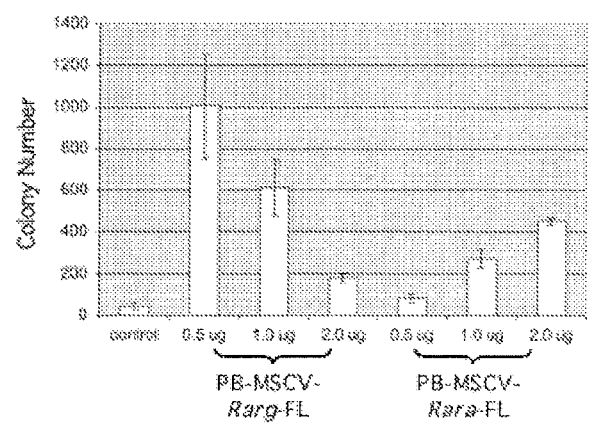
Figure 13:
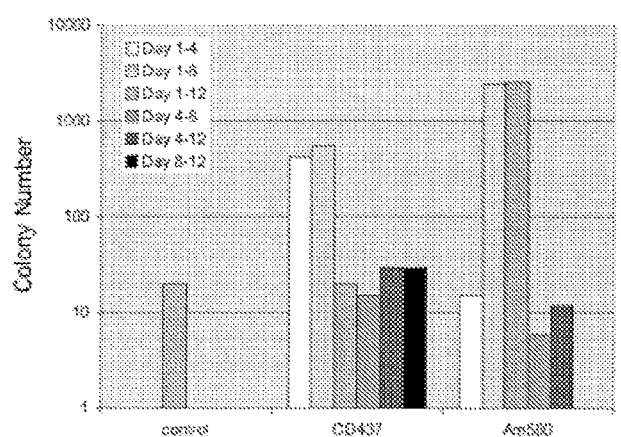
Figure 13:
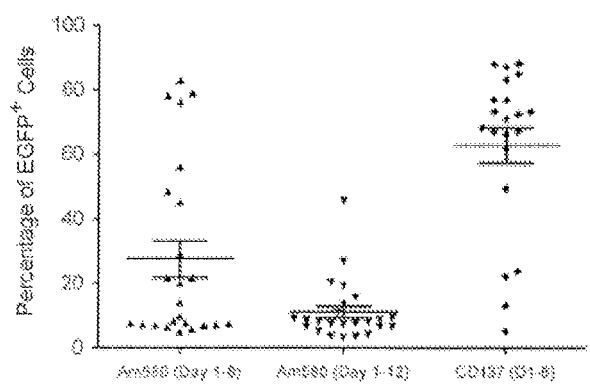

FIG. 13. RA signalling plays critical roles in reprogramming of mouse MEFs to iPS cells. A. Higher quality of iPS cells was co-related to surviving higher concentrations of Puromycin. B. Drastic increase of reprogramming efficiency by over-expression of Rarg-FL. C. iPS cell culture plate showing Rarg increasing reprogramming efficiency. Cells were stained with crystal violet. D. Over-expression of Rarg-DN also improves the quality of iPS clones but reduces reprogramming efficiency. E. Dose of Rarg affects reprogramming efficiency. F. Reprogramming efficiency increased by Rarg- or Rara-specific agonists. G. Rarg-specific agonist improves the quality of iPS cells.

Figure 14:
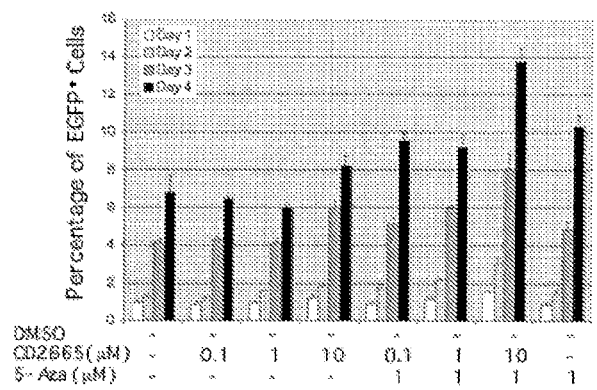
Figure 14:
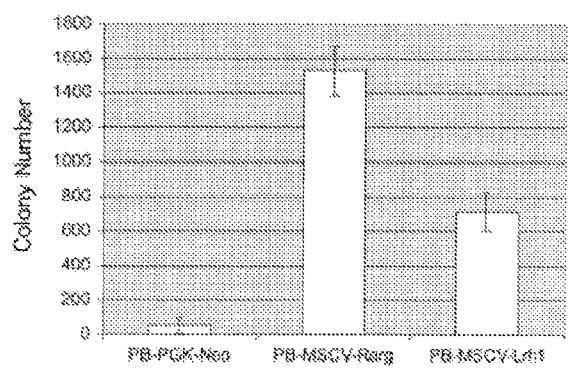
Figure 14:
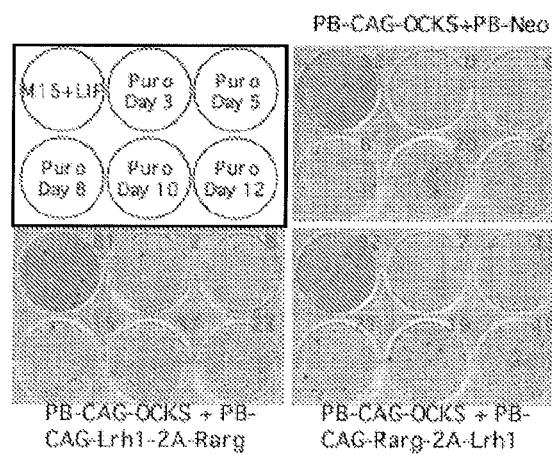
Figure 14:
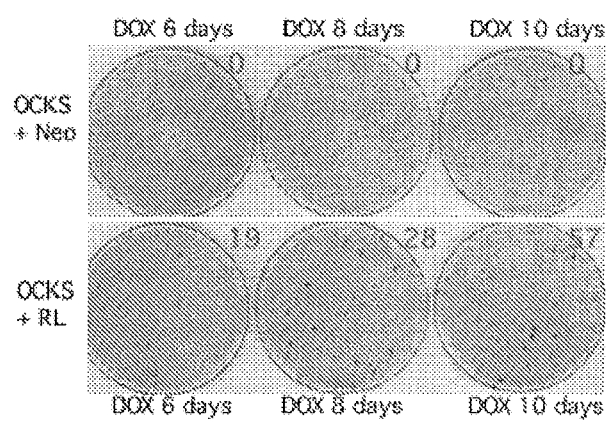
Figure 14:
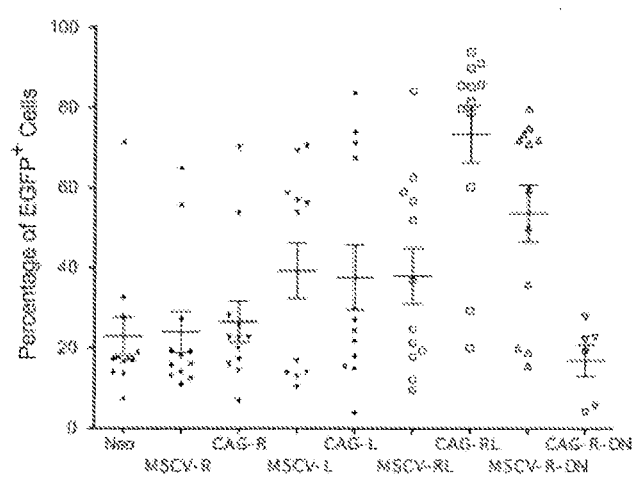

FIG. 14. Rarg and Lrh1 work synergistically to promote reprogramming. A. Rarg-specific antagonist treatment can improve the quality of partially reprogrammed iPS clone. B. Over-expression of Lrh1 promotes reprogramming. C. Rapid reprogramming of MEFs by the six factors as indicated by the much early appearances of Puro resistant iPS cell colonies. D. Expression of Rarg and Lrh1 was required for rapidly achieving fully reprogrammed pluripotency. E. Dose of Rarg and Lrh1 expression is critical for quality of iPS cells.

Figure 15:
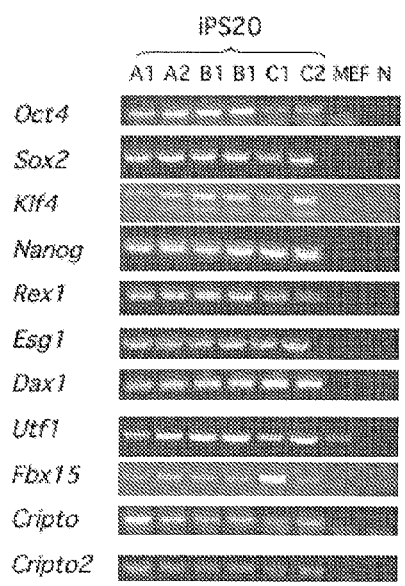
Figure 15:

FIG. 15. High quality of iPS Cells reprogrammed by Six Factors. A. Mouse iPS cells produced using Rarg and Lrh1 had robust expression of ES cell pluripotency markers. B. The six factor-induced mouse iPS cells could contribute to all lineages in teratoma.

Figure 16:
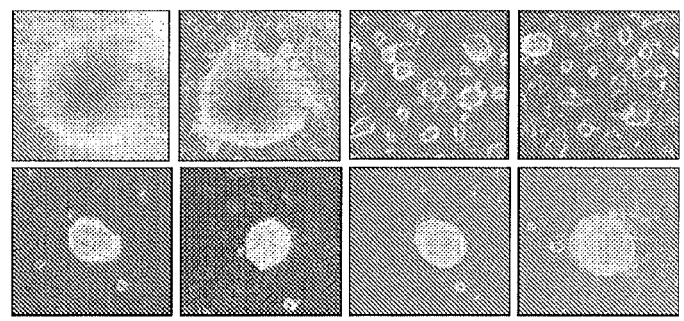
Figure 16:
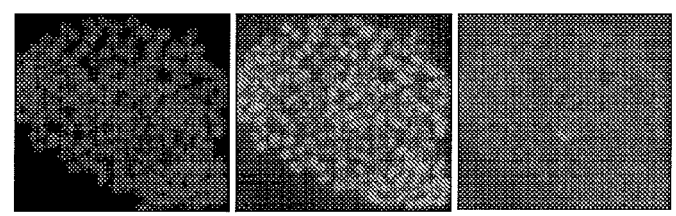
Figure 16:
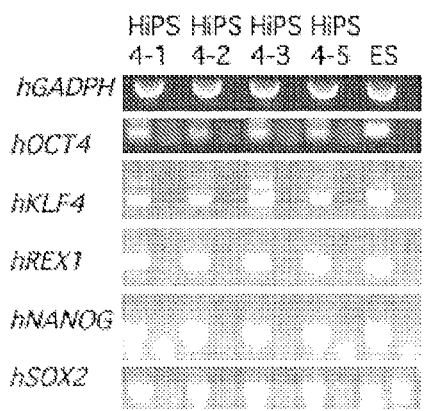

FIG. 16. Production of High Quality Human iPS cells using the Six Factors. A. Human iPS cell colonies produced in M15 plus hLIF media (top panel). HUman iPS cell colonies expanded in 2i plus hLIF culture condition (bottom panel). B. Human iPS cells express high level of OCT4 and NANOG. C. RT-PCR analysis confirms high levels of expression of pluripotency gene in human iPS cells. 4-1, 4-2, 4-3, and 4-5 are human iPS cells. ES: human ES cell control.

TABLES

Table 1. A list of mouse gene promoters that contain the putative RAREoct element.
Table 2. A list of human gene promoters that contain the putative RAREoct element.
Table 3. Primers used in cDNA cloning.
Table 4. Primers used in Splinkerette PCR.
Table 5. Primers used in RT-PCR and DMR analysis.
Table 6. Applied Bioscience pre-designed Taqman probes for real-time RT-PCR of mouse and human genes.
Table 7. Custom designed human QPCR probes.

DETAILED DESCRIPTION

Here we report fast and efficient reprogramming of mouse and human somatic cells. In mice, embryonic fibroblast cells (MEF) were reprogrammed. The iPS clones generated were highly homogenous by morphology and molecular biology criteria. When the same six factors were used to reprogram human neonatal foreskin dermal fibroblast cells (HDFn), we identified human pluripotent stem cell clones. These cells can also be subcloned at single cell density in mouse ES cell culture condition and expanded without any discernible chromosomal abnormality. We have also shown that efficient transposition can be achieved in these human iPS cells, whose efficiency is comparable to mouse ES cells.

In one aspect the invention relates to a nuclear reprogramming factor (NRF) for somatic cells. Suitably the NRF is able to promote the formation of iPS from somatic cells.

In one aspect the nuclear reprogramming factor comprises a gene product from a retinoic acid receptor RAR/RXR family member (e.g. Rarα, Rarγ, Rarβ, RXRα, RXRβ, RXRγ—also referred to herein as Rara, Rarg, Rarb, RXRa, RXRb, RXRg in one aspect having the mouse or human sequence), and/or retinoic acid, and/or a gene product from an Lrh1 family member (e.g. Lrh1, Sf1, or other members of the Ftz-F1 subfamily of nuclear receptors/nR5a steroid hormone receptor family), and/or a gene product that is involved in transporting a retinoic acid family member.

Reference to RAR family includes reference to RXR family, unless otherwise apparent from the context. In one aspect the nuclear reprogramming factor comprises both a retinoic acid receptor RAR family member (e.g. Rarα, Rarγ, Rarβ) and an Lrh1 family member, for example full length Rarg and Lrh1. In one aspect, reference to a RAR family member refers to RAR.

In one aspect the nuclear reprogramming factor comprises retinoic acid, for example all trans RA, or 9-cis RA, suitably at a concentration of between than $10^{-8}$ and $10^{-10}$ M, suitably $10^{-9}$M.

Reference herein to family members and gene products thereof, including polynucleic acid encoding said gene products, such as RAR family members and Lrh1 family members, includes members of the same gene/protein family within one species, family members in different species and variants thereof, such as proteins with substitutions, deletions or additions, suitably that are functionally equivalent in that they are able to promote the formation of iPS from somatic cells as disclosed herein, either alone or in combination with other factors, suitably as assessed by methods described in this application. Such gene products include sequences having at least 70%, preferably at least 80%, 90% or 95% homology or identity to the sequences of the NRFs according to the invention, at the amino acid or nucleotide level, able to promote the formation of iPS from somatic cells as disclosed herein, either alone or in combination with other factors, suitably as assessed by methods described in this application. Preferably, the RAR family member is human full length wild type Rav or Rara sequence. Preferably, the LRH1 family member is human full length wild type LRH1 sequence.

In one aspect, reference to protein or gene product in any aspect of the invention refers to the human full length wild type sequence of that protein or gene product.

In one aspect the promotion of the formation of iPS from somatic cells is assessed by activation of Oct4 gene expression, for example at levels seen in ES cells, or the formation of iPS cells having any of the characteristics disclosed herein.

In one aspect gene products are proteins having a human or mouse sequence, or are variants thereof, as described above.

Reference to gene products herein in the context of NRF components is not limited to proteins or polypeptides made by expression from polynucleic acid, but includes proteins or fragments thereof that may be directly synthesized, for example.

Reference to gene products also includes other, non protein species, that may be produced from a gene, such as polynucleic acid fragments that arise from transcription of DNA into RNA.

Reference to a gene product from a retinoic acid receptor (RAR/RXR) family member includes gene products of a mutant of an RAR/RXR family member having some activity of the gene product from a retinoic acid receptor (RAR/RXR) family member.

In one aspect the invention relates to a nuclear reprogramming factor for a somatic cell, which comprises a protein encoded by a mutant of an RAR/RXR family member, and/or an Lrh1 family member, such as a mutant with reduced or abrogated protein function, or a mutant with enhanced activity. A mutant having some activity of the parent protein that was mutated may be considered a variant of that protein, as discussed above.

In one aspect the invention relates to a nuclear reprogramming factor for a somatic cell, which comprises a protein encoded by a dominant negative mutant of a RAR family member and/or an Lrh1 family member. Suitably a dominant negative mutant protein is able to block ES cell differentiation induced by Retinoic Acid (RA), suitably at a high concentration of RA such as 1.0 µM. In one aspect the nuclear reprogramming factor comprises a protein encoded by a dominant negative mutant of Rarg or Rara. In one aspect the protein is a C terminal deletion of part of the Rarg protein. In one aspect the mutant is a mutant of Rarg from which amino acids corresponding to the last intron (intron 9) of Rarg have been deleted. In one aspect the protein is a dominant negative form of Rara, suitably Rara-DN.

Seq of wild type RARG
(SEQ ID No. 1)
ATGGCCACCAATAAGGAGAGACTCTTTGCGCCCGGTGCCCTGGGGCCTGG

ATCTGGTTACCCAGGAGCAGGCTTCCCATTCGCCTTCCCAGGTGCACTCA

GAGGGTCGCCACCATTTGAGATGCTGAGCCCTAGCTTCCGGGGCCTGGGC

-continued

CAGCCTGACCTCCCCAAGGAGATGGCTTCTCTCTCGGTGGAGACACAGAG

CACCAGCTCGGAGGAGATGGTACCCAGCTCTCCCTCACCCCCACCACCTC

CTCGGGTCTATAAGCCATGCTTTGTATGCAATGACAAGTCTTCTGGCTAC

CACTATGGGGTCAGCTCCTGTGAAGGCTGCAAGGGCTTCTTCAGACGCAG

CATTCAGAAAAACATGGTGTATACATGTCACCGTGACAAAAACTGTATCA

TCAACAAGGTCACCAGAAATCGATGCCAGTACTGCAGGCTACAAAAGTGT

TTCGAAGTGGGCATGTCCAAGGAAGCTGTAAGGAACGATCGAAACAAGAA

GAAAAAGGAGGTAAAAGAGGAGGGCTCGCCCGACAGCTATGAACTGAGTC

CACAGTTAGAGGAACTCATCACCAAGGTCAGCAAAGCCCACCAGGAGACT

TTTCCCTCACTCTGCCAGCTGGGCAAGTACACCACGAACTCCAGTGCAGA

TCACCGGGTGCAGCTGGACCTGGGGCTGTGGGACAAGTTCAGCGAGCTGG

CCACCAAATGCATCATCAAGATTGTGGAGTTTGCGAAGCGGCTGCCTGGT

TTTACAGGGCTCAGCATTGCCGACCAGATCACGCTGCTCAAGGCTGCTTG

TCTGGACATCCTAATGCTGCGGATCTGTACAAGGTATACCCCAGAGCAGG

ACACTATGACATTCTCGGATGGGCTGACCCTGAACCGAACCCAGATGCAC

AATGCTGGCTTTGGGCCCCTTACAGACCTCGTCTTTGCCTTTGCCGGGCA

GCTGCTGCCCCTGGAGATGGATGACACCGAGACTGGGCTACTTAGTGCTA

TCTGCCTCATCTGTGGAGACCGAATGGACCTGGAAGAGCCCGAGAAGGTG

GACAAGCTGCAGGAGCCCCTGCTGGAAGCCCTGAGGCTCTATGCCCGGCG

ACGGAGACCCAGCCAACCCTACATGTTCCCAAGGATGCTGATGAAAATCA

CCGACCTCCGGGGCATCAGCACTAAGGGAGCAGAAAGGGCTATAACCCTG

AAGATGGAGATTCCAGGCCCGATGCCACCCCTGATCCGAGAGATGCTGGA

GAACCCGGAGATGTTTGAGGACGACTCCTCGAAGCCTGGCCCCCACCCCA

AGGCTTCCAGTGAGGACGAAGCTCCAGGGGGCCAGGGCAAAAGGGGCCAA

AGTCCCCAACCTGACCAGGGGCCCTGA

Sequence of Mutant Rarg
(SEQ ID No. 2)
ATGGCCACCAATAAGGAGAGACTCTTTGCGCCCGGTGCCCTGGGGCCTGG

ATCTGGTTACCCAGGAGCAGGCTTCCCATTCGCCTTCCCAGGTGCACTCA

GAGGGTCGCCACCATTTGAGATGCTGAGCCCTAGCTTCCGGGGCCTGGGC

CAGCCTGACCTCCCCAAGGAGATGGCTTCTCTCTCGGTGGAGACACAGAG

CACCAGCTCGGAGGAGATGGTACCCAGCTCTCCCTCACCCCCACCACCTC

CTCGGGTCTATAAGCCATGCTTTGTATGCAATGACAAGTCTTCTGGCTAC

CACTATGGGGTCAGCTCCTGTGAAGGCTGCAAGGGCTTCTTCAGACGCAG

CATTCAGAAAAACATGGTGTATACATGTCACCGTGACAAAAACTGTATCA

TCAACAAGGTCACCAGAAATCGATGCCAGTACTGCAGGCTACAAAAGTGT

TTCGAAGTGGGCATGTCCAAGGAAGCTGTAAGGAACGATCGAAACAAGAA

GAAAAAGGAGGTAAAAGAGGAGGGCTCGCCCGACAGCTATGAACTGAGTC

CACAGTTAGAGGAACTCATCACCAAGGTCAGCAAAGCCCACCAGGAGACT

TTTCCCTCACTCTGCCAGCTGGGCAAGTACACCACGAACTCCAGTGCAGA

TCACCGGGTGCAGCTGGACCTGGGGCTGTGGGACAAGTTCAGCGAGCTGG

```
                          -continued
CCACCAAATGCATCATCAAGATTGTGGAGTTTGCGAAGCGGCTGCCTGGT

TTTACAGGGCTCAGCATTGCCGACCAGATCACGCTGCTCAAGGCTGCTTG

TCTGGACATCCTAATGCTGCGGATCTGTACAAGGTATACCCCAGAGCAGG

ACACTATGACATTCTCGGATGGGCTGACCCTGAACCGAACCCAGATGCAC

AATGCTGGCTTTGGGCCCCTTACAGACCTCGTCTTTGCCTTTGCCGGGCA

GCTGCTGCCCCTGGAGATGGATGACACCGAGACTGGGCTACTTAGTGCTA

TCTGCCTCATCTGTGGAGACCGAATGGACCTGGAAGAGCCCGAGAAGGTG

GACAAGCTGCAGGAGCCCCTGCTGGAAGCCCTGAGGCTCTATGCCCGGCG

ACGGAGACCCAGCCAACCCTACATGTTCCCAAGGATGCTGATGAAAATCA

CCGACCTCCGGGGCATCAGCACTAAGGGATGATGATGA
```

In one aspect the invention relates to an antagonist of RAR/RXR and/or an antagonist of an Lrh1 family member, and use of said antagonist in the generation and or maintenance of IPS cells. A suitable antagonist of Rarg is CD2665. A suitable antagonist of Rara is RO-41-5253. In a further aspect the antagonist is used in combination with an inhibitor of DNA methylation such as 5-Azacytidine and 5-aza-2'-deoxycytidine.

In one aspect the reprogramming factor comprises an agonist of RAR and/or an Lrh1 family member, for example an agonist of Rara such as AM580 or an agonist of Rarg which is CD437.

In one aspect the nuclear reprogramming factor comprises a combination of any one, or more, of the above described RAR family members, Lrh1 family members, retinoic acid, agonists thereof, and mutants and/or variants thereof, for example a combination of both an RAR (full length) and Lrh1 (full length) family member, such as Rarg and Lrh1.

Suitably the effect of Rarg and Lrh1 is synergistic, in that an effect on iPS reprogramming is observed which is more than additive, for example with respect to the number and/or quality of the iPS cells obtained, as described below. Suitably the iPS reprogramming is assessed by monitoring levels of Oct4 expression as described above, and/or the ability to produce iPS having one or more of the characteristics listed herein for iPS cells.

The nuclear reprogramming factor may additionally include other additional components. Suitably the NRF is capable of reprogramming somatic cells to form iPS cells, and suitably at a higher frequency than the Yamanaka factors alone. Yamanaka factors are disclosed in EP1970446, the teaching of which is incorporated herein by reference.

The NRF may comprise one or more of the Yamanaka factors or nucleic acid encoding them. In one aspect the nuclear reprogramming factor comprises a MYC protein, such as C-MYC, or nucleic acid encoding it. In one aspect the nuclear reprogramming factor comprises a KLF protein, such as KLF4, or nucleic acid encoding it. In one aspect the nuclear reprogramming factor comprises a SOX gene such as SOX2 or nucleic acid encoding it. In one aspect the nuclear reprogramming factor comprises Oct4 or nucleic acid encoding it. In one aspect the nuclear reprogramming factor comprises C-MYC, KLF-4, Oct4 and SOX2 or nucleic acid encoding C-MYC, KLF-4, Oct4 and SOX2.

Reference to any gene or protein herein, such as C-MYC, Oct4 KLF-4 and SOX2, includes genes or proteins sharing identity with C-MYC, KLF-4, Oct 4 and SOX2, and family members, as discussed above, suitably encode proteins having reprogramming activity, at least to some degree, in common with the full length wild type sequences.

Reference to proteins for inclusion in the NRF of the invention includes variants such as addition, deletion or substitution mutants, suitably having reprogramming activity, at least to some degree, in common with the full length wild type sequences.

Various factors that can replace components of the Yamanaka factors have been identified. Where the invention is described as using one or more Yamanaka factors, it will be appreciated that the present invention also contemplates the inclusion of the Yamanaka factor replacements for each factor. For example Oct4-independent reprogramming has been reported through over-expression of the orphan nuclear receptor Nr5a2, which is able to replace oct4. Another orphan nuclear receptor, Esrrb, is reportedly capable of replacing Klf4. Thus the invention relates to a NRF comprising, or comprising nucleic acid encoding, a combination of a nuclear reprogramming factor of the invention and Nr5a2 or Esrrb.

In one aspect the nuclear reprogramming factor comprises a combination of:
(i) a gene product, or a polynucleotide encoding, any one, or more, selected from the list of; the above-described RAR/RXR family members, Lrh1 family members, agonists thereof, antagonists thereof, and mutants and variants thereof, preferably both RAR and Lrh1 family members, retinoic acid and factors regulating or regulated by the RA signalling pathway; and
(ii) a gene product of or a polynucleotide encoding factors capable of conferring pluripotency to differentiated cells or transforming adult cells into pluripotent cells, the factors preferably being one or more of: an Oct family gene, a Klf family gene, and a Myc family gene, and a Sox family gene, or functional equivalent thereof.

In one aspect a functional equivalent of Klf-4 is Esrrb. In one aspect a functional equivalent of Oct4 is Nr5a2.

In one aspect the NRF comprising a gene product from an RAR family member, an Lrh1 family member, an Oct family member and a Myc family member, or a polynucleotide or polynucleotides encoding said gene products.

In one aspect the NRF comprises a gene product from an RAR family member, an Lrh1 family member, KLF-4 and SOX2 and does not comprise C-MYC and Oct 4.

Preferably, in a method according to the invention using such NRFs to reprogram human somatic cells to IPS cells, the KLF-4 and SOX2 expression is achieved during reprogramming of the somatic cell but the human IPS cells lines produced do not have KLF-4 and/or SOX2 insertion in the chromosome. In one aspect there is no integration of KLF-4 and/or SOX2 into the chromosome of the cell to be reprogrammed, for example no integration of transposons encoding such factors in human iPSC lines of this invention.

In one aspect the NRF comprises or encodes OCT4, CMYC, LRH1 and RARG, and in a further aspect does not comprise either of the other 2 Yamanaka factors.

In one aspect the NRF includes at least an Oct family gene, a Klf family gene, and a Myc family gene, or gene products thereof. Suitable family members include a gene product of Oct 3/4, Klf4, c-Myc family gene and Sox2 or polynucleotide encoding the same.

In one aspect the NRF of the present invention comprises or encodes all 4 Yamanaka factors, namely an Oct family gene product, a Klf family gene product, a Myc family gene product, and a Sox family gene product, or functional equivalents of these gene products which are capable of promoting reprogramming of somatic cells to iPS cells.

In one aspect the nuclear reprogramming factor additionally comprises or encodes one or more of:

a cytokine together with the gene product of the Myc family gene, or alternatively, instead of the gene product of the Myc family gene. As a more preferred embodiment, there is provided the aforementioned factor, wherein the cytokine is basic fibroblast growth factor (bFGF) and/or stem cell factor (SCF).

a gene product of the TERT gene in addition to a gene product of each of an Oct family gene, a Klf family gene, a Myc family gene, and a Sox family gene;

a gene product or gene products of one or more kinds of genes selected from the group consisting of the following genes: SV40 Large T antigen, HPV16 E6, HPV16 E7, and Bmi1, in addition to a gene product of each of the Oct family gene, the Klf family gene, the Myc family gene, the Sox family gene, and the TERT gene a gene product or gene products of one or more kinds of genes selected from the group consisting of the following: Fbx15, Nanog, ERas, ECAT15-2, Tcl1, and β-catenin.

a gene product or gene products of one or more kinds of genes selected from the group consisting of the following: ECAT1, Esg1, Dnmt3L, ECAT8, Gdf3, Sox15, ECAT15-1, Fth117, Sa114, Rex1, UTF1, Stella, Stat3, and Grb2.

A preferred NRF comprises or encodes full length Oct 3/4, a Klf4, c-Myc family gene and Sox2, Lrh1 and Rarg, suitably deliverable into a somatic cell and which can be expressed within the cell.

In one aspect the NRF described above additionally comprises or encodes RXR, such as RXR alpha, beta or gamma.

In an alternative aspect of the invention the NRF comprises a component of the RA signalling pathwayable to act to promote reprogramming of somatic cells as disclosed herein. Such components may be a downstream effector of RA, upstream or downstream modulators of RARG or LRH1 or molecule affecting the production of RA. Assays disclosed in this application allow the identification of suitable components of the pathway, namely those capable of reprogramming of somatic cells to form iPS cells as described, and the determination of suitable concentrations of those components to effect the reprogramming.

NRFs of the invention may also include modulators of the endogenous gene or endogenous gene products, such as a modulator of the gene or gene product of RAR/RXR family members and Lrh1 family members. For example the endogenous expression of LRH1 and/or RARG may be increased. Manipulation of the host gene expression may be achieved by insertion or manipulation of a promoter driving expression to provide the necessary enhanced reprogramming effects. Such promoters may include LTS from MSCV (retrovirus), CAG and inducible promoter Tet-On. Such NRFs can be used in all the described aspects of the invention. By way of example, a nuclear reprogramming factor comprising or expressing the 4 Yamanaka factors or functional equivalents thereof and Lrh1 may be used in conjunction with a cell in which endogenous Rarg expression is increased, or can be increased by treatment of the cell with an extracellular factor. Such factor may be a chemical or change in environmental condition, for example. Thus the present invention also relates to a cell the genome of which has been modified to allow the expression of an endogenous (RAR/RXR) family member, and/or Lrh1 family member to be increased, or to be adjusted in response to an extracellular factor.

The NRF can be used in combination with other compounds or drugs, which may be compounds or drugs that facilitate reprogramming, or indeed improve delivery of efficacy of the NRF.

The NRF may comprise gene products, such as proteins, as described above, either expressed alone or in the form of fusion proteins.

In one aspect the NRF may comprise or consist of a polynucleic acid encoding the components of the reprogramming factor described above which may be delivered to a somatic cell. Thus it can be understood that the reprogramming factor may comprise a protein composition, or nucleic acid composition designed to allow expression of suitable proteins within a cell, or indeed a combination of polynucleic acid and protein.

Synthesised or purified chemicals may also be part of a NRF of the invention. For example, where agonists or antagonists of proteins are used, then a NRF may comprise a chemical designed to activate or inhibit protein function, as appropriate.

Where a polynucleic acid is used, and where multiple gene products form the NRF, then these may be encoded on the same or different polynucleic acid fragments. For example, in one aspect, Rarg and Lrh1 gene products may be encoded on one DNA construct, and 1, 2, 3, or 4 of the Yamanaka factors may be encoded on a separate polynucleic acid fragment.

Polynucleic acid encoding protein components of the NRF may be naked DNA, or DNA complexed with a delivery agent, or in the form of a vector such as a plasmid or transposon or viral vector, suitable for delivery into a somatic cell.

For completeness, to the extent that the invention also relates to polynucleic acids which encode components of said NRFs, then the invention also relates to polynucleic acids that encode variants of said NRF components, said components having the ability to promote the formation of iPS from somatic cells as disclosed herein, either alone or in combination.

The invention also relates to cells comprising polynucleotides and vectors of the invention, not limited to somatic cells, and including cells such as bacterial cells suitable for the production of nucleic acid for transformation or transfection, for example.

The various components of the NRF may be expressed under the control of a regulatory system, either singly or in combination. In one aspect one or more component, for example any of the 4 Yamanaka factors (or equivalent thereof), Rarg or Lrh1, either alone or in combination, may be expressed under the control of Tet-On® system (Clonetech). Thus in one aspect the promoter controlling the expression of, for example, Lrh1 or Rarg, is controlled by an element within the promoter that responds to he presence or absence of tetracycline.

Reprogramming factors of the present invention may be used in combination with other reprogramming techniques, such as hypoxia.

By way of examples, the NRF of the present invention may comprise the following, as proteins, or DNA or RNA encoding said proteins, or a mixture of polynucleic acid and protein:

Rarg and Lrh1
Rarg, Lrh1, Oct4, and cMyc
Rarg, Lrh1, Sox2 and Klf4.
Rarg, Lrh1, Oct4, cMyc, Sox2 and Klf4.

For the avoidance of doubt, the NRF may comprise a single component protein, or comprise a nucleic acid encoding a single protein, or encode a single agonist or antagonist as disclosed herein.

Expression levels of certain proteins such as Rarg may have an effect on the reprogramming efficiency. Accordingly the invention also relates to a method for identification of a suitable reprogramming level of an NRF, the method comprising varying the concentration of the NRF or a component thereof and monitoring the production of iPS cells, either directly or for example by monitoring the expression of Oct4, and selecting a suitable concentration of an NRF for use in reprogramming. The invention also comprises methods for reprogramming as disclosed herein, where an appropriate amount of the NRF, as assessed above, is used to achieve reprogramming.

Suitable concentrations of various elements disclosed herein include, for example, Ro-41-5253 RARa antagonist 1 µM, CD2665 RARg antagonist 1 µM, AM580 RARa agonist 10 nM, CD437 RARg agonist 100 nM, All-trans RA and 9-cis RA at around $1\times10^{-9}$M.

The NRF of the invention may comprise a vector, such as a plasmid, live viral vector or transposon, the vector having a polynucleic acid encoding a component of the NRF as disclosed herein. In particular the vector may be an expression vector comprising a nucleic acid encoding a component of the nuclear reprogramming factor as described herein.

Vectors of the invention are generally suitable for delivery of nucleic acid encoding a component of the NRF into a somatic cell, and may also contain the necessary sequences to allow or facilitate expression of the proteins encoded by the nucleic acid.

Vectors may express a component of the NRF from an extrachromosomal locus or may be designed to integrate into the chromosome and express from within the chromosome.

Transposons such as PiggyBac may be suitable for use in the delivery of nucleic acid into somatic cells and also in the delivery of exogenous DNA into iPS cells of the invention.

The present invention further relates to a method for preparing an induced pluripotent stem cell by nuclear reprogramming of a somatic cell, which comprises a step of contacting a nuclear reprogramming factor described herein with the somatic cell.

The method may optionally comprise a further step of selecting or screening for iPS cells, for example, by selection of screening for cells having properties as described herein.

Contacting the NRF with the somatic cell may take place in a number of ways. For example, the nuclear reprogramming factor may be added to a culture of the somatic cell or a vector encoding components of a nuclear reprogramming factor introduced into a somatic cell. The vector may be a plasmid, or transposon or viral vector, for example.

Where the NRF comprises a protein then suitably the NRF is exposed to the somatic cell in culture, for example continuously for 3, 4, 5, 6, 7, 8, 9 or 10 days, in one aspect no more than 8, 9, 10, 11, 12, 13, 14 or 15 days.

The somatic cell may be any suitable cell, and types of somatic cells to be reprogrammed are not particularly limited. For example, matured somatic cells or progenitors may be used, as well as somatic cells of an embryonic period. When induced pluripotent stem cells are used for therapeutic treatment of diseases, it is desirable to use somatic cells isolated from the patient to be treated. For example, somatic cells involved in diseases, somatic cells participating in therapeutic treatment of diseases and the like can be used. Somatic cells may be any suitable mammalian cell such as, by way of example, human, mouse, rat, pig, sheep or cow.

In one aspect, the expression of exogenous reprogramming factors (also referred to as exogenous factors or exogenous NRFs) contacted with the somatic cells is switched-off once the somatic cells have been reprogrammed. This may be achieved by using inducible promoters such as Tet-On which allows expression of the exogenous reprogramming factors to be switched off by removing Dox from the culture media. Suitably, the expression of exogenous reprogramming factors is switched off about 4 days after contacting the somatic cell with the NRF at which stage the somatic cells has been reprogrammed sufficiently to enable conversion to iPS cells without need of additional input from exogenous reprogramming factors.

Suitably iPS cells may be identified and selected within 10 days after treatment of the cells with NRF, e.g. as assessed by Oct 4 expression as described herein, such as within 3, 4, 5, 6, 7, 8 or 9 days, and suitably after 2 days treatment.

A method for selecting induced pluripotent stem cells that appear in a medium according to the method of the present invention is not particularly limited, and any well-known means may be suitably employed, for example, a drug resistance gene or the like can be used as a marker gene to isolate induced pluripotent stem cells using drug resistance as an index. Various media that can maintain an undifferentiated state and pluripotency of ES cells, and various media which cannot maintain such properties, are known in this field, and induced pluripotent stem cells can be efficiently isolated by using a combination of appropriate media. Differentiation and proliferation abilities of isolated induced pluripotent stem cells can be easily confirmed by those skilled in the art by using confirmation means widely applied to ES cells.

In one further aspect the invention relates to the use of an RA agonist or antagonist, preferably a RA antagonist, in ES cell media or iPS cell media, for any cell line such as human or mouse, in a suitable amount to maintain pluripotency. The invention also relates to a cell culture media comprising an agonist or antagonist of RA.

In one aspect, the invention provides a method for reprogramming a somatic cell to an induced pluripotent cell by temporally boosting RA signalling. In one aspect boosting RA signalling may comprise contacting somatic cells with one or more of:

i a gene product from a retinoic acid receptor (RAR/RXR) family member, or an agonist of that gene product;
ii a gene product from an Lrh1 family member; or an agonist of that gene product;
iii retinoic acid or a gene product involved in synthesizing or metabolizing a retinoic acid family member; or an agonist of that gene product;
iv a gene product that is involved in transporting a retinoic acid family member:
v a polynucleic acid encoding any of (i) to (iv)

The RA signalling is suitably boosted for 3, 4, 5, 6, 7 or 8 days, in one aspect no more than 8 days.

Suitable doses of gene products may be readily determined by the person skilled in the art, to optimise iPS production. Gene products such as proteins from family members listed above, or fragments or variants thereof, may be either added to cells directly or expression within the cell manipulated, for example by insertion of expression vectors expressing a desired gene product, or manipulation of host gene expression by promoter insertion or manipulation.

Thus the invention also relates to a somatic cell wherein the level of expression of one or more of the following gene products has been modified by transfection or genetic manipulation of the host cell genome, for example by a targeted insertional event.

i a gene product from a retinoic acid receptor (RAR/RXR) family member, or an agonist of that gene product;

ii a gene product from an Lrh1 family member; or an agonist of that gene product;

iii a gene product involved in synthesizing or metabolizing a retinoic acid family member; or an agonist of that gene product;

iv a gene product that is involved in transporting a retinoic acid family member The invention further relates to an induced pluripotent stem cell obtained or obtainable by the methods described herein. The iPS may be from any species, but is suitably obtained from mouse or human somatic cells as a starting material.

Somatic cells may be any suitable cells, such as fibroblast cells.

In particular the invention relates to an induced human pluripotent stem cell obtained or obtainable by the methods described herein.

An iPS cell of the invention suitably has one or more of the following properties:

IPS cells are suitably undifferentiated pluripotent cells. Pluripotency may be assessed by, for example, the detection of expression of one or more pluripotency markers such as Oct4, Nanog, Rex1 or by demethylation of promoter regions for one, or more of, Oct4, Nanog, Rex1.

Expression of Oct 4 in the context of this application means expression comparable to the expression level in the reporter ES cell line where the IRES-Puro-Egfp cassette was targeted to the Oct4 locus as described in the examples below and shown in FIG. 2a and FIG. 7. These reporter ES cells were resistant to 2.0 µg/ml Puromycin.

IPS cells can suitably be dissociated to viable single cells, capable of cell division in appropriate media.

IPS cells can suitably grow in M15+hLIF media. (For 600 ml M15, 500 or 504 ml (82%) GIBCO™ Knockout™ D-MEM (Invitrogen, catalog number: 10829018), 90 ml (15%) Fetal Calf Serum (ES Cell Tested), 6 ml (1%) Penicillin-Streptomycin-Glutamine (100×), liquid (Invitrogen, catalog number: 10378-016), 4.3 ul of β-mercaptoethanol (Sigma, catalog number: M 7522). LIF ($1\times10^6$ units)

IPS cells can suitably grow in 2i+LIF media. (2i+LIF medium is 2i medium supplemented with 1 u/mL human recombinant LIF. 2i medium is N2B27 medium supplemented with 1 uM PD0325901 and 3 µM CHIR99021. N2B27 medium is a 1:1 mixture of DMEM/F12 supplemented with modified N2 (insulin 25 µg/mL, apo-transferrin 100 µg/mL, progesterone 6 ng/mL, putrescine 16 µg/mL, sodium selenite 30 nM, bovine serum albumin fraction V 50 µg/mL) and Neurobasal medium supplemented with B27. DMEM/F12, Neurobasal medium, and B27 are all from Gibco)

IPS cells of the present invention are suitably capable of differentiating into somatic cells in suitable cell culture conditions.

Suitably iPS cells of the present invention can be used to generate chimeras following blastocyst injection, demonstrating germline transmission.

IPS cells are suitably capable of forming teratomas when injected into mice.

In one aspect iPS cell growth is suitably independent of FGF that is usually required for human ES cells.

Primary iPS cell colonies may suitably be dissociated into single cells, which are then capable of forming secondary colonies and stable cell lines in appropriate media, such as M15+LIF.

IPS cells of the present invention are suitably morphologically distinct from those prepared under the same conditions using only the 4 Yamanaka factors oct4, cmyc, sox2 and Klf4.

In one aspect the iPS cells comprise two X chromosomes in a pre-inactivation state. The two X chromosomes in mouse female ground state ES cells are in a pre-inactivation state while mouse EpiSCs have already undergone X inactivation. Female iPSCs produced with 6F) Yamanaka factors, LRH1 and RARG) had two active X chromosomes.

The genome integrity of the iPS cells may be confirmed using spectral karyotyping analysis. Genetic stability/genome integrity is indicated by the fact that even after in vitro culture cells retain a normal karyotype. Suitably the iPS cells have the normal karyotype after passaging (for example, after at least 2, 3, 4, 5, 6, 7, 8, 9 or 10, 15 or 20 passages).

Thus in one aspect the invention relates to an induced human pluripotent cell characterised by at least one of the following:
  expression of one or more pluripotency markers such as Oct4, Nanog, Rex1;
  growth independent of FGF;
  retain a normal karyotype as measured by using spectral karyotyping analysis after passaging;
  capable of forming teratomas when injected into mice;
  demethylation of promoter regions for one, or more of, Oct4, Nanog, Rex1;
  Cells can be dissociated to viable single cells capable of forming secondary colonies;
  proliferation in M15+hLIF media and/or 2i+LIF media
  Absent or insignificant exogenous reprogramming factor expression (for example, any one or more of LRH1, Rarg, Oct4, Sox2, Klf4 and c-Myc, or equivalents thereof), In one aspect the IPS cells of the invention do not express exogenous reprogramming factors. As discussed throughout the description, this may be achieved by using inducible promoters such as Tet-On which allows expression of the exogenous reprogramming factors to be switched off by removing Dox from the culture media. This may also be achieved by preventing integration of exogenous reprogramming factors into the chromosome of the iPS cells or by removing any integrated exogenous reprogramming factors from the genome so that the IPS cells are free of any exogenous reprogramming factors. In some instances, promoters such as Tet-On are used to shut down expression of exogenous reprogramming factors may allow some expression of exogenous factors detectable by RT-PCR but which is biologically insignificant.

In one aspect human iPS cells of the invention do not grow well and do not keep pluripotency in FGF media.

In one aspect iPS production may be assessed by constructing a somatic cell containing an oct4-IRES-puro-egfp knock in as described herein. Cells containing said construct which are considered to be mammalian, eg mouse or human iPS cells, are suitably resistant to puromycin at a concentration of 2 ug/ml or higher and preferably are also GFP positive, suitably as detected by flow cytometry.

In a further aspect the invention relates to a somatic cell derived by differentiation of the induced pluripotent stem cell as described herein, and a tissue, organ or non-human animal comprising a somatic cell or cells derived by differentiation of the induced pluripotent stem cell as described herein. Differentiation may be achieved in vitro by using various factors, compounds or combination of factors and compounds known to the skilled person.

Cells obtainable by differentiating the iPS cell of the invention cell (for example, cardiac muscle cells, insulin producing cells, nerve cells and the like) are potentially extremely useful, because they can be utilized for stem cell transplantation therapies for a variety of diseases such as cardiac insufficiency, insulin dependent diabetes mellitus, Parkinson's disease, cancer and spinal cord injury, thereby the ethical problem concerning the use of human embryo and rejection after transplantation can be avoided.

Cells, tissues and organs generated in vitro/ex vivo from iPS, as disclosed herein, may be valuable in the evaluation of the function or toxicity of compounds, such as medicaments. The invention thus also relates to use of iPS cells, and tissues, organs and non-human animals derived from such iPS cells, in the analysis of the effects of a compound or medical treatment.

Human iPS cells can be used for high throughput screening readouts relevant to infectious agents. In one aspect, genetically modified or genetically mutated, including homozygous mutant (primarily loss of function mutations) human iPS cells or somatic cells differentiated from iPS cells may be infected by a pathogen to identify factors that have inhibition or enhancement of the infection.

The present invention further provides a method for evaluating a physiological function or toxicity of a compound, a medicament, a poison or the like by using various cells obtained by inducing differentiation of an induced pluripotent stem cell obtained by the aforementioned method.

The invention also relates to a pharmaceutical composition comprising a nuclear reprogramming factor, or cell or tissue as described herein, in combination with a pharmaceutically acceptable excipient. Suitable excipients include, inter alia, pharmaceutically acceptable buffers, carriers and water.

In one aspect the tissues or organs or animals of the invention are not derived from a human iPS cell. In an alternative aspect the tissues or organs are derived from a human iPS cell. In one aspect the invention does not extend to a human embryo or adult, but may extend to a human organ or tissue, or population of human cells derived from a single iPS cell before embryonic status is assigned.

In one aspect the iPS cell is a single human cell.

The genome of iPS cells of the invention is suitably tractable to genetic manipulation, for example by transposons. We have demonstrated that human iPS cells can be transfected with transposon which transpose into the chromosome at high efficiency. The invention thus relates to a method for genetic modification of an iPS cell, the method comprising delivery of an exogenous polynucleotide sequence into the host chromosome, suitably delivery of a transposon, or gene trapping or gene targeting construct. However, any suitable construct may be delivered into the iPS cells of the invention.

In one aspect the iPS cells of the present invention are tractable to homologous recombination and/or targeting, suitably allowing the correction of genetic mutations and to potentially introduce new beneficial genetic changes in patient cells.

The invention also relates to an iPS cell the genome of which comprises an exogenous DNA sequence.

The present invention also relates to methods of medical treatment, and uses of the invention in medicine.

iPS cells as disclosed herein, or somatic cells generated therefrom, may be used as medicaments in therapy. Moreover, the ability to generate patient-specific human iPS lines from human somatic cells makes it possible to correct a patient-specific genetic abnormality in iPS cells and generate mutation-free cells for gene therapy. Tissues and organs generated from iPS as described herein may also be used in medicine. NRFs may also be used as medicaments, where they are delivered and exert an effect directly in vivo, as well as their use in the production of iPS.

Thus the invention relates to use of a nuclear reprogramming factor or iPS cell or cell, tissue or organ derived therefrom, suitably as described herein, in medicine.

The invention further relates to a method of treating a patient in need thereof, the method comprising delivery of a pharmaceutically acceptable amount of a reprogramming factor or iPS cell or cell derived therefrom, suitably as described herein, or delivery of a tissue or organ derived from an iPS cell as described herein.

The invention further relates to use of a nuclear reprogramming factor or iPS cell or cell derived therefrom, suitably as described herein, in the preparation of a medicament for the treatment of a patient in need thereof.

Where a somatic cell is isolated from the body and reprogrammed to an iPS cell, then suitably the cell is from the patient intended to be treated.

The invention further relates to a method of promoting differentiation, using cells or a NRF of the present invention, for example, to produce a starting iPS cell or cell population from which to produce differentiated cells. In one aspect, agonists or antagonists of RAR family members, such as Rarg, Rara or of LRH1 may be used to promote cell differentiation in patients.

An alternative aspect of the invention relates to the promotion of differentiation of cells rather than reprogramming. As disclosed herein, over expression of full length Rarg and Rara enhanced differentiation induced by RA. The present invention therefore relates to a method for improving differentiation ability and/or growth ability of a cell, which comprises the step of contacting a somatic cell with full length RAR such as Rarg or Rara at a concentration and duration appropriate to elicit differentiation in combination with RA.

Any suitable target cell may be used in the present invention. Suitable cells for treatment by the NRF of the invention includes hepatocytes, stomach cells, skin cells and monocytes. In one aspect target cells for treatment express either LRH1/RARG, or have low levels of COUP-TFI/II and other negative effectors as described herein, or both.

The invention also relates to miRNAs and siRNAs which improve iPS cell quality and production efficiency, for example of COUP-TFI, COUP-TFII, GCNF and G9a and others that are regulators of pluripotent genes and interact with RA receptors and LRH1 family members. The invention also relates to using the wild type or mutant forms of COUP-TFI, COUP-TFII, GCNF and G9a and other regulators of pluripotent genes to improve iPS cell quality and production efficiency.

The present invention relates in one aspect to certain proteins and combinations of proteins that are able to increase number and/or quality of iPS cells, for example RARα, Rarg and Lrh1. Reference to proteins or polypeptides herein is taken to include functional equivalents of said proteins or polypeptides capable of eliciting the same, or substantially similar biological activities. Similar activities may be the ability to stimulate iPS cell production and/or IPS quality, suitably assessed using the methods as disclosed herein. By way of non limiting example, full length RARα is known to enhance iPS production, and functional equivalents of this protein suitably also enhance iPS production, suitably at least to 20, 30, 40, 50% or more of the level seen by RARα. Functional equivalents may include other members of the protein family, from the same or different species, or variants of proteins such as substitution, addition or deletion mutants.

Likewise, to the extent that the present invention relates to polynucleic acid, for example encoding the proteins or polypeptides disclosed herein, or functional equivalents thereof, the invention relates to any polynucleic acid encoding said sequences, such as naturally occurring sequences, or degenerate equivalents to said naturally occurring sequences. The invention includes polynucleotides one strand of which can hybridise to a polynucleic acid encoding a protein or polypeptide functionally equivalent to a protein or polypeptide of the invention, suitably under stringent hybridisation conditions. Stringent conditions may include e.g. 6×NaCl/sodium citrate (SSC) at about 45° C. is applied for a hybridisation step, followed by a wash of 2×SSC at 50° C. or, e.g., alternatively hybridization at 42° C. in 5×SSC, 20 mM NaPO4, pH 6.8, 50% formamide; and washing at 42° C. in 0.2×SSC. Those skilled in the art understand that it is desirable to vary these conditions empirically based on the length and the GC nucleotide base content of the sequences to be hybridised, and that formulas for determining such variation exist (See, for example, Sambrook et al, "Molecular Cloning: A Laboratory Manual", Second Edition, pages 9.47-9.51, Cold Spring Harbor, N.Y.: Cold Spring Harbor Laboratory Press (1989)).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In one aspect such open ended terms also comprise within their scope a restricted or closed definition, for example such as "consisting essentially of", or "consisting of".

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

All documents referred to herein are incorporated by reference to the fullest extent permissible.

Any element of a disclosure is explicitly contemplated in combination with any other element of a disclosure, unless otherwise apparent from the context of the application.

The present invention is further described by reference to the following examples, not limiting upon the present invention.

EXAMPLE 1

Expressing retinoic acid receptor gamma (RARG) and liver receptor homolog 1 (LRH-1) together with four Yamanaka factors reprograms mouse and human somatic cells to ground state iPSCs.

Abstract

Stem cells have the capacity for self-renewal and the potential to differentiate into different cell types. Somatic cells can be reprogrammed to Induced Pluripotent Stem Cells (iPSCs) by expressing four transcription factors but the mechanism is still not clear. Here we report that modulating retinoic acid (RA) signalling profoundly promoted reprogramming. Furthermore, co-expressing Rarg (retinoic acid receptor gamma) and Lrh-1 (liver receptor homolog 1) with the four factors led to rapid reprogramming of mouse embryonic fibroblast cells (MEFs) to ground state or naïve iPSCs directly in chemically defined 2i media. The critical functions of RA signalling and RARG and LRH-1 in reprogramming are evolutionarily conserved as this combination of factors reprogrammed human fibroblast cells to iPSCs that resembled naïve mouse ES cells in growth properties, gene expression, signalling dependency, and receptiveness to genetic modification. Mouse embryonic fibroblast cells (MEFs) can be reprogrammed to iPSCs by expression of four Yamanaka factors, Oct4, Sox2, c-Myc and Klf4 (1-3). These factors are also able to reprogram cells of a variety of somatic lineages in the mouse (4-6) and human (7-9). Many improvements of the original reprogramming protocol have been described which include replacing Oct4 (10), use of chemical compounds (11-14), modulating signalling transduction pathways such as Wnt signalling (15), perturbing cell cycle regulators such as p53 (16, 17), and enhancing germ-line competence of mouse iPSCs (18). Importantly, mouse iPSCs have passed the most stringent pluripotency test by generating full-term adult mice in the tetraploid complementation assay (19-21). Despite the tremendous progress in iPSC field, many technical challenges remain and still little is known about the reprogramming mechanism. For instance, in the mouse, reprogramming MEFs takes 2-3 weeks, and only a small number of reprogrammed cells are true iPSCs (22, 23). In the human, iPSCs reprogrammed from primary cells are similar to conventional human ES cells, which are thought to be more characteristic of mouse EpiStem cells (24).

Results

RA Signalling is Required in Reprogramming

Retinoic acid signalling has complex and pleiotropic functions during vertebrate development (25). Prolonged exposure to high concentrations of RA induces differentiation of mouse embryonic stem (ES) cells and embryonal carcinoma (EC) cells. However, biochemical studies indicate that RA receptors (RARs) are able to positively regulate Oct4 expression through RAR:RXR heterodimers binding to RAREoct, a composite RA responsive element located in the promoter of the Oct4 locus (26-28), in the presence of low concentrations of RA (28, 29). Moreover, high levels of the heterodimers effectively compete off repressors such as COUP-TFs from binding RAREoct (28).

To investigate the role of RA signalling in reprogramming, we cloned cDNAs of Oct4, Sox2, Klf4, cMyc, Rara and Rarg into a PB-MSCV vector where expression of the cDNAs was controlled by the MSCV LTR (FIG. 6A). Although exogenous c-Myc is not essential for reprogramming, omission of it reduces reprogramming efficiency and delays the process (23, 30). The individual PB-MSCV-cDNA vectors were co-transfected with a PB transposase plasmid into MEFs (FIG. 1A). PB transposition facilitates efficient integration of the PB transposon into the genome, thus ensuring stable expression of the cDNAs (31).

ES cell pluripotency requires proper levels of Oct4 (Pou5f1) expression (32), and activation of Oct4 is known to be a crucial event in reprogramming (3). To monitor activation of the endogenous Oct4 locus in reprogramming and to allow unbiased assessment of iPSC quality, we made an Oct4 reporter mouse line where the IRES-Puro-GFP cassette was targeted to the 3'UTR of the Oct4 locus (FIG. 6B). The targeted ES cells were resistant to 2.0 µg/ml Puromycin (Puro) selection. These ES cells were not visibly green under fluorescent microscope but could be distinguished by flow cytometry (FIG. 6C). Insertion of the Puro-GFP cassette into the Oct4 locus did not appear to affect ES cell pluripotency since germline-competent chimeras were derived from these ES cells. MEFs from the Oct4 reporter mice were thus used in all the MEF reprogramming experiments, and consequently, reprogramming and iPSC quality could be conveniently monitored and assessed by either Puro resistance or GFP expression in iPSCs.

Colonies consisting of ES cell-like cells started to appear 3 weeks after transfection and by day 30, expression of Rara and Rarg increased AP$^+$ ES cell-like colony number by one and two orders of magnitude, respectively (FIG. 1B-C). In contrast, expressing a Rara dominant-negative (DN) form (33) completely blocked reprogramming in most experiments (FIG. 1B), and the few growing colonies could never be expanded into stable lines. These results thus demonstrated the essential role of RA signalling in reprogramming MEFs to iPSCs.

We next examined the specificity and the temporal requirement of RA signalling in reprogramming using a synthetic agonist of RA specific to Rarg, CD437 (34). Addition of CD437 to the culture media at the recommended concentration for 4 or 8 days drastically increased reprogramming of MEFs to iPSCs (FIG. 1D). However, treatment of MEFs with CD437 beyond 8 days after transfection (FIG. 1D), or transfection of increased amounts of PB-MSCV-Rarg plasmid DNA reduced reprogramming efficiency (FIG. 6D), reflecting a temporal- and dose-dependent manner for RA signalling in reprogramming.

Expression of the endogenous Oct4 is unstable in iPSCs reprogrammed by the four Yamanaka factors (11). We also found that most iPSC-like colonies (at day 30 after PB transfection), whether reprogrammed by the four factors alone or by 4-factors plus Rarg, survived only 1.0 µg/ml Puro selection, and GFP expression could not be detected (FIG. 6E), indicating low levels of Oct4 expression in these cells. Further analysis confirmed their partially reprogrammed status: low levels of endogenous pluripotency gene expression (FIG. 1E), and retention of substantial DNA methylation in the differentially methylated regions (DMRs) in the Nanog and Rex1 promoters (FIG. 1F). On the other hand, a small number of colonies were obtained which were resistant to 2.0 µg/ml Puro, and were similar to ES cells regarding pluripotency gene expression, demethylation at the Nanog and Rex1 promoters, and GFP expression (FIG. 1E-F and FIG. 6E). Surprisingly, most colonies obtained from CD437 (day 1-4) treatment expressed GFP (FIG. 1G) and survived 2.0 µg/ml Puro selection. Therefore, modulating RA signalling not only profoundly increased reprogramming efficiency but could improve iPSC quality as well as defined by stable Oct4 expression. In subsequent experiments, we used resistance to 2.0 µg/ml Puro or GFP expression as surrogate criteria for pluripotency quality of mouse primary iPSCs reprogrammed from Oct4-Puro-GFP MEFs.

Rapid Reprogramming by Co-Expressing Rarg and Lrh-1

SF-1 (Nr5a1) and LRH-1 (Nr5a2) are two members of the Nr5a steroid hormone family. By forming hetero-dimers binding to RAREoct, Sf-1 and Rarg synergistically promote and maintain Oct4 expression in EC cells (29). However, Lrh-1 but not Sf-1, is expressed in ES cells and is required at the post-implantation stage of embryonic development (35). We therefore constructed two PB vectors: PB-CAG-OCKS and PB-CAG-RL, in which the four Yamanaka factors (OCKS), Rarg and Lrh-1 (RL), were linked by T2A, respectively (FIG. 7A). Expression of these factors was controlled by the CAG promoter. The two PB vectors were co-transfected or separately into the Oct4 reporter MEFs for reprogramming. As soon as 4 days after co-transfection of OCKS and RL, 2.0 µg/ml Puro$^r$ microscopic ES-like colonies appeared. These Puro$^r$ colonies continued growing into large ES-like colonies and were usually picked from day 7 to day 10 for expansion and further characterization (FIG. 7B). At day 10 after transfection, there were up to 20 times more AP$^r$ colonies reprogrammed by the six factors compared to the control expressing the OCKS alone (FIG. 7C). Transfection of RL alone did not produce any colony in 10 days.

Previous studies using virus-based Doxycycline-inducible vectors suggest that exogenous factor-induced reprogramming is a gradual process with defined intermediate steps where distinct cells populations are poised to become iPSCs (36, 37). It usually takes at least 10-16 days of expressing Yamanaka factors before cells enter a self-sustaining pluripotent state (36, 37). To determine the temporal requirement of the six exogenous factors in reprogramming, we switched the CAG promoter to the tetracycline response element (TRE) so that expression of these factors was inducible by Doxycycline (Dox) (FIG. 7A). The two PB vectors, PB-TRE-OCKS and PB-TRE-RL, as well as PB-CAG-rtTA expressing the reverse tetracycline transactivator (FIG. 7A), were transfected into the Oct4 reporter MEFs. Dox was added to the media and was subsequently removed at several time points (FIG. 2A). Four-day Dox treatment was sufficient to obtain reprogrammed cells that survived 2.0 µg/ml Puromycin which continued to grow to iPSC colonies in the absence of Dox (FIG. 2B-C). In contrast, it took at least 12 days to obtain 2.0 µg/ml Puromycin cells if only the Yamanaka factors were expressed (PB-TRE-OCKS) (FIG. 2B). Co-expressing Rarg/Lrh-1 therefore dramatically accelerated reprogramming. Importantly, the majority of the iPSCs produced with the six factors were of high quality based on their resistance to 2.0 µg/ml Puro and GFP expression (FIG. 2D). In contrast, expressing Rarg or Lrh-1 separately with OCKS did not apparently affect reprogramming kinetics nor iPSC quality (FIG. 2D).

As well as Oct4 reporter lines, we made a Rex1-GFP mouse line where the GFP-IRES-Puro cassette was inserted into the Rex1 locus and used these Rex1-GFP MEFs to perform reprogramming experiments using the Dox inducible factors. Rex-1 is only expressed in ES cells but not in EpiSCs (Brons et al., 2007; Tesar et al., 2007) and thus represents an ideal marker for fully reprogrammed cells. Dox-independent GFP-positive colonies again appeared after four days Dox treatment using the 4 Yamanaka factors, Lrh1 and Rarg.

Complete activation of the pluripotency genes such as Oct4 is a critical event in reprogramming and in somatic cell cloning (38). We thus investigated whether expression of Rarg and Lrh-1 could indeed rapidly activate Oct4 expression in a reporter assay using a luciferase expression cassette linked to the Oct4 promoter (FIG. 7D). PB-CAG transposons carrying various cDNAs were co-transfected with the reporter plasmid into MEFs which were harvested two days later. Expression of Rarg or Lrh-1 alone, or OCKS, did not have a substantial effect on the luciferase reporter expression (FIG. 2E). However, co-expressing Rarg and Lrh-1 in ES cells increased the reporter expression by 4-5 fold (FIG. 2E), similar to the previous biochemical finding that Rarg and Sf-1 synergistically activate Oct4 expression in EC cells (29). Therefore, expression of Rarg and Lrh-1 was primarily responsible for the rapid activation of the Oct4 locus in the six-factor reprogramming system and OCKS was involved in reprogramming likely at relatively late stages.

Dox-independent iPSCs reprogrammed from MEFs with the 6 factors were further characterized. These iPSCs expressed proper levels of pluripotency genes detected by both immunostaining and qRT-PCR analyses, and had DNA demethylation in the promoter regions of Oct4 and Nanog (FIG. 3A-C and FIG. 8A-B). Furthermore, these cells were able to differentiate to somatic cell types representing all three germ layers in teratomas when injected to F1 hybrid mice (FIG. 3D). Finally, these iPSCs efficiently contributed to the germline in chimeras once injected into blastocysts (FIG. 3E). Importantly, most iPSC lines did not express detectable exogenous factors (FIG. 8C), and the chimeras did not develop tumours (12 months, n=7). Therefore, resistance to 2.0 µg/ml Puro and GFP expression were suitable criteria for assessing primary iPSCs from Oct4 reporter MEFs. Because most iPSC colonies reprogrammed using our six-factor system were fully reprogrammed, no reporter MEFs were required for routine reprogramming. We were able to readily produce iPSCs from wild type C57B6J MEFs. Moreover, a single PB transposon carrying cDNAs of all six factors (OCKSRL) also reprogrammed MEFs efficiently.

Reprogramming of MEFs to Ground State iPSCs Directly in 2i Media

Reprogramming MEFs is normally carried out in standard mouse ES cell media containing serum or a serum replacement. The complex nature of these media does not allow precise determination of the function of individual chemical compounds or growth factors in reprogramming. Reprogramming somatic cells directly in a chemically defined media would facilitate therapeutic iPSC production as well. We therefore attempted reprogramming in a chemically defined media, N2B27-LIF, which is able to maintain mouse ES cell pluripotency (39). MEFs were transfected with PB-TRE-OCKS alone or together with PB-TRE-RL, and cultured in gelatinized plates in N2B27-LIF media with Dox for up to 17 days. ES cell-like colonies appeared as early as 5 days after expressing the six factors, and were picked for expansion at day 14-17 in N2B27-LIF plus two inhibitors (2i/LIF media), PD (ERK1/2 inhibitor PD0325901), and CH (GSK3 inhibitor CHIR99021). Addition of 2i in N2B27 media selects and maintains ground state mouse and rat ES cells (40, 41). We obtained on average 50 iPSC colonies by expressing OCKS and RL in each transfection, of which most (83%) could be expanded into lines in 2i/LIF (FIG. 4A). In contrast, AP$^+$ colonies did not appear until at least day 12 after transfecting PB-TRE-OCKS, and only a small number of them (28%) could be expanded into stable lines.

We next attempted reprogramming MEFs to iPSCs directly in 2i/LIF media. Remarkably, ground state iPSCs rapidly appeared in culture by expressing OCKS plus RL, but not OCKS alone (FIG. 9A), indicating that some of the MEFs, soon after expressing the six factors, were already in an intermediate reprogramming stage that were further promoted to ground state pluripotency in 2i/LIF media (11, 36, 37). We next examined quality of the iPSCs reprogrammed in 2i/LIF. These iPSCs expressed pluripotency genes at proper levels (FIG. 4B-C) and differentiated to somatic cell types of all three germ layers in vitro (FIG. 4D) and in teratomas (FIG. 9B). Therefore, modulating retinoic signalling by expressing Rarg and Lrh-1 rapidly reprograms MEFs to ground state or naïve iPSCs.

OCKS and RL Enabled Production of Human iPSCs with Unique Properties

The ability of OCKS plus RL to rapidly reprogram MEFs to high quality iPSCs with efficient induction of endogenous Oct4 expression prompted us to explore whether these factors would also play similar roles in reprogramming human somatic cells. Computational analysis identified that the RAREoct at the Oct4 locus is highly conserved in several mammalian genomes (FIG. 5A). Experimental evidence also supports a possible role for RAREoct in regulating Oct4 expression in human cells (42). Interestingly, in both the mouse and human genomes, RAREoct-like elements were identified in about 30-40 loci (Table S1 and S2), but the Oct4 locus was the only one found in both genomes that contained the RAREoct site, indicating the functional significance of this element at the Oct4 locus.

We thus explored the possibility of producing human iPSCs that were similar to mouse ES cells. We first produced human iPSCs by constitutively expressing the six factors using the CAG promoter. The PB-CAG transposons carrying the human OCKS and RL cDNAs were transposed into human neonatal foreskin dermal fibroblast cells (HDFn) by co-expressing the PB transposase. As early as 10 days after transfection, colonies formed in mouse ES cell media (M15-

LIF), some of which were morphologically similar to mouse ES cell colonies (e.g., compact raised colonies, high nucleus-to-cytoplasm ratios, and prominent nucleoli) (FIG. 10A). These colonies were picked at day 12-14 and were subsequently cultured using standard mouse ES cell protocols (FIG. 10A). Upon dissociation to single cell suspension with trypsin and plating onto STO feeder cells, secondary colonies formed efficiently with up to 70% re-plating efficiency. We were able to establish stable lines from many primary colonies that could be maintained on feeders in M15-LIF media for at least 50 passages. In the control using only OCKS, primary colonies were morphologically distinct from those generated with OCKS plus RL (FIG. 10A). We had never been able to successfully establish stable lines from these OCKS colonies in M15-LIF media, consistent with a previous report (7). Besides their ability to proliferate in regular mouse ES cell media, these human iPSCs expressed key pluripotency genes (FIG. 10B-C), and could also be maintained in 2i/LIF media which confirmed their similarity to ground state mouse ES cells (40) (FIG. 10A). To determine the differentiation potential of these human iPSCs, we injected them subcutaneously to immune-compromised NSG mice (43). Despite continuous expression of exogenous factors from the CAG promoter, these cells formed teratomas with cell types representing all three germ layers (FIG. 10D). Furthermore, even after extensive in vitro culture, these iPSCs retained the normal karyotype (FIG. 10E). Using Y chromosome polymorphism markers, we also confirmed the iPSC's HDFn origin (FIG. 10F).

To obtain human iPSCs that were independent of expression of exogenous factors, we used the Tet-On system where human cDNAs of the six factors were cloned into the PB-TRE plasmids. These PB-TRE-cDNA plasmids were co-transfected with PB transposase and the rtTA plasmids into HDFn cells. Dox was added to induce exogenous factor expression (FIG. 5B). Colonies containing ES cell-like cells appeared 10-15 days after transfection. These colonies were trypsinized and re-plated into feeder plates in M15-LIF media without Dox. The Dox-independent secondary colonies were subsequently expanded into lines on feeders in KSR-LIF media plus the two inhibitors PD and CH (KSR-2i-LIF) (40, 41). From one experiment, we established five Dox-independent iPSC lines which were maintained in KSR-2i-LIF media (FIG. 5C). Similar to mouse ES cells, these human iPSCs were easily expanded, and were usually passaged every 3-4 days with a 1 to 4 split ratio. To determine the pluripotency of these Dox-independent iPSCs, we examined expression of key pluripotency genes. They expressed endogenous Oct4, Sox2, and Nanog at levels comparable to that in human ES cells (FIG. 5D and FIG. 11A), and were stained positively for human ES cell surface markers (FIG. 5E and FIG. 11B). Importantly, expression of exogenous factors was not detectable even in RT-PCR analysis (FIG. 11C). Finally, the Dox-independent human iPSCs could be readily differentiated to cells of three germ layers in vitro and in vivo (FIG. 5F-G).

In contrast to dependence on Lif/Jak/Stat pathway for pluripotency maintenance in mouse ES cells, conventional human ES cells derived from embryos are cultured in media containing FGF2 (basic FGF), and LIF alone is insufficient to maintain pluripotency (44, 45). The Dox-independent human iPSCs did not require FGF in the media. Indeed, they grew well and kept pluripotency gene expression in KSR-2i-LIF media even in the presence of a FGF receptor inhibitor SU54021 (FIG. 5H). Conventional human ES cells are resistant to JAK inhibitor (JAKi) but are differentiated in the presence of BMP4. In contrast, our human iPSCs proliferated well in the presence of BMP4, but if a JAK inhibitor that blocked Stat3 phosphorylation was added to KSR-2i-LIF media, they lost expression of OCT4 and NANOG and were rapidly differentiated (FIG. 5H). Finally, compared to human ES cells, our human iPSCs expressed lower levels of lineage specific genes such as PAX6, GATA6, and SOX17 in KSR-2i-LIF media (FIG. 5H).

To determine whether the Dox-independent human iPSCs had the potential to become FGF dependent, we changed the culture media to KSR-FGF2. After three passages, these cells still grew well and did not show obvious differentiation compared to growing in KSR-2i-LIF media. They were morphologically similar to human ES cells, and expressed proper levels of pluripotency genes such as OCT4 and NANOG (FIG. 5I). However, once the culture media was changed back to KSR-2i-LIF, these iPSCs became differentiated and expressed high levels of SOX17 and SOX1 with concomitant loss of OCT4 and NANOG expression (FIG. 5I), similar to the behaviour of human ES cells (44). These data thus demonstrated that human iPSCs growing in KSR-2i-LIF media had the potential to covert to cells similar to conventional human ES cells, but not vice versa. Therefore, Dox-independent human iPSCs produced using our six-factor platform were more immature than conventional human ES cells, and resembled the ground state mouse ES cells based on their growth properties, signalling dependence and gene expression (40, 41). We thus named these human iPSCs as Sanger Human iPSCs or SH-iPSCs.

The fact that SH-iPSCs were similar to mouse ES cells suggested that they would be useful for genetic studies. Before using these cells for extensive manipulation in vitro, we examined the genome integrity of SH-iPSCs using spectral karyotyping analysis. Even after extensive in vitro culture (20 passages), these cells retained a normal karyotype (FIG. 11D), indicating that they were genetically stable. We thus performed PB transposition to introduce exogenous DNA into these cells by co-transfecting the PB-PGK-Neo transposon and the PBase plasmid into SH-iPSCs. From one electroporation, we obtained about 500,000 G418$^r$ colonies, which accounted for about 10% of the cells surviving electroporation, a transposition efficiency comparable to using mouse ES cells (31).

Efficient PB transposition in SH-iPSCs opens up the opportunity to perform genome-wide mutagenesis screens. To begin exploring this possibility, we transfected the PB-SA-βgeo gene trap transposon and PB transposase plasmid into SH-iPSCs. Integration of the SA-βgeo cassette into expressing loci enabled βgeo expression and the trapping events to be scored as G418 resistance. From one electroporation, we recovered 22,000 G418$^r$ colonies, which represented 0.3% of the electroporation surviving cells. Since our human iPSC lines were derived from foreskin fibroblast cells and were therefore XY, we investigated the mutation efficiency at the HPRT locus on the X chromosome, taking advantage of 6TG resistance in cells that lose HPRT activity. Out of 22,000 G418 resistant colonies, we obtained one 6-TG colony. Molecular analysis of this clone demonstrated that the PB inserted in intron 2 and disrupted HPRT transcription and splicing (FIG. 11E). Therefore, SH-iPSCs were suitable for genetic manipulation and screens.

The unique capability of our six-factor reprogramming system can be attributed to the role of RA signalling and the related factor LRH-1 in pluripotent stem cells. In contrast to the well-characterized differentiation-promoting activities of retinoic acid, RA signalling can positively regulate Oct4 expression through RAREoct. High levels of RAR:RXR heterodimers, which specifically bind RAREoct, overcome repression by COUP-TFs (28). An alternative route for regulating Oct4 expression by RA signalling is through the SF-1 binding site within the RAREoct. RARG/LRH-1 heterodimers bind RAREoct and synergistically activate Oct4 expression by effectively competing off repressors (29). These steroid hormone receptor dimers subsequently recruit coactivators, such as CBP/p300, P/CAF and SRC1/TIF2 (25, 46), to the Oct4 locus to facilitate further chromatin remodelling. Consequently, one of the most critical hurdles in somatic cell reprogramming, namely activation of the endogenous Oct4 locus (47), is readily overcome shortly after exogenous factor expression. It is interesting to note that cells expressing high levels of LRH-1 and low levels of COUP-TFs such as mouse hepatocytes (48) have been demonstrated to have higher reprogramming efficiencies (5).

Our data clearly show that activation of the Oct4 locus is an early reprogramming event and a critical one. It is known that Oct4 locus activation by expressing the four Yamanaka factors is unstable, which leads to many partially reprogrammed colonies in regular ES cell media (11). Reprogramming using the Oct4-reporter MEFs permits the direct visualization of Oct4 locus activation. When only the four factors are expressed, a small number of cells are GFP$^+$ in flow cytometry, indicating Oct4 activation in these cells. However, the GFP$^+$ cell number did not change substantially over the next 8 days, consistent with the long reprogramming process mediated by the four factors. In contrast, in MEFs expressing the six factors, GFP$^+$ cells increased exponentially from day 3 after transfection. Moreover, a small number of MEFs acquired high levels of Oct4 expression almost immediately after expression of the 6 factors (24 hours). This rapid Oct4 activation however can't be maintained and subsequent reprogramming steps could be aborted without the continuous expression of Yamanaka factors for a couple of more days since self-sustainable iPSC colonies were only obtained after 3-4 days of exogenous factor expression in the Dox-induction experiments (FIG. 2).

ES cells that are deficient for Lrh1 do not show severe pluripotency defects thus it is not a major essential component of the pluripotency circuit (35). It is however required for maintenance of Oct4 expression during ES cell differentiation (35). Recent evidence also suggests that Lrh1 acts downstream of canonical Wnt signalling and also regulate other pluripotency factors such as Nanog and Tbx3 besides Oct4 (64). These key functions of Lrh1 likely play important role in its ability to replace Oct4 in reprogramming (10). However, our data demonstrate that this replacement is likely to be context dependent since expression of Lrh1 alone, together with the four Yamanaka factors, does not significantly improve reprogramming in terms of iPSC quality or kinetics. Only the synergistic interaction between Rarg and Lrh1 profoundly impacts reprogramming that produces ground state mouse iPSCs rapidly and enables generation of human iPSCs that closely resemble ground state mouse ES cells. Interesting, although Rarg is expressed in many cell types including MEFs, however, its highest expression is found in ES cells, the endogenous Rarg in MEFs or human fibroblast cells does not appear to be sufficient to cooperate with exogenous introduced Lrh1 to promote rapid and efficient reprogramming.

A recent report shows that human iPSCs obtained from reprogramming secondary fibroblast cells (iPSC-derived) could be kept in 2i/LIF media plus Forskolin (49). These cells appear to be similar to ground state mouse ES cells (40), and thus provide independent evidence that ground or naïve state of pluripotency exists in human. Although their human iPSCs could become Dox-independent, they grow slowly and could not be maintained for longer than 15-20 passages. Another recent study also describes mouse ES cell-like human iPCSs that still depend on exogenous factor expression (50), which to some extent appear to be similar to the PB-CAG human iPSCs obtained using PB-CAG-cDNAs (FIG. 10). In contrast to these reports, SH-iPSCs were directly reprogrammed from human primary fibroblast cells, independent of expressing the exogenous reprogramming factors, and could be maintained for over 50 passages in media containing 2i/LIF. Moreover, they were FGF-independent but relied on LIF-JAK-STAT pathway. SH-iPSCs therefore resemble the envisioned ground state human pluripotent stem cells and should be useful for functional dissection of the human genome.

Materials and Methods

Plasmid Vector Construction

To make PB-TRE, PB-MSCV and PB-CAG vectors, the Tet response element (TRE) was amplified from pTight (Clontech), the MSCV LTR was amplified from pMSCV-Neo (Clontech) and the CAGG promoter was amplified from a pBluescript-CAG vector (unpublished data), and cloned into a PB-bpA vector (unpublished data).

cDNAs of the four mouse and human Yamanaka factors were amplified (primers in Supplementary Table 3) from original retroviral vectors (Addgene) and cloned into the PB-TRE, PB-MSCV and PB-CAG transposon vectors, respectively. Mouse and human Rarg, Lrh1 and Sf1 were amplified from IMAGE clones (Geneservice) and cloned into transposon vectors.

Mouse and Human ES and iPSC Culture

Mouse ES cells and iPSCs were normally cultured in M15 media: knockout DMEM, 15% foetal bovine serum (FBS, Hyclone), 1× Glutamine-Penicillin-Streptomycin (GPS, Invitrogen), 1× non-essential amino acids (NEAA, Invitrogen), 0.1 mM β-mercaptoethanol (β-ME, Sigma) and 10$^6$ U/ml LIF (Millipore).

Human iPSCs reprogrammed by PB-CAG vectors were cultured in M15 media, with 10$^6$ U/ml human recombinant LIF. Human iPSCs reprogrammed by PB-TRE vectors were maintained in DMEM/F12 with 1×GPS (Invitrogen), 20% Knockout Serum Replacement (Invitrogen), 1×NEAA, 0.1 mM β-mercaptoethanol (β-ME, Sigma) and two inhibitors, CHIR99021 (5 µM) and PD0325901 (1 µM).

The human ES cell lines BG01V/hOG (from Invitrogen) and H1 (from WiCell) were cultured in hESC medium: DMEM/F12 with Glutamax (Invitrogen), 20% Knockout Serum Replacement (Invitrogen), 1×NEAA, 0.1 mM β-mercaptoethanol (β-ME, Sigma) and 4.0 ng/ml FGF2 (Invitrogen).

Preparation of MEF Cells and HDFn Cells for Reprogramming

MEFs were prepared from 12.5 d.p.c. Oct4-IRES-Puro-Egfp embryos. To reduce embryo-to-embryo difference, MEFs from several embryos with the same genotype were mixed together for expansion in M10 media. MEFs were passaged once before they were counted, aliquoted and frozen down. Before electroporation, 1×10$^6$ MEFs were plated onto one gelatinized 15-cm tissue culture plate. When MEFs were 70-80% confluent, they were typsinized and collected for electroporation. M10: knockout DMEM, 10% foetal bovine serum (FBS, Hyclone), 1×GPS, 1× non-essential amino acids (NEAA, Invitrogen).

HDFn cells were purchased from Invitrogen and maintained in Media 106 supplemented with low serum growth supplement (Invitrogen). The primary HDFn culture was passaged once before being counted, aliquoted and frozen. Before electroporation, 5×10$^5$ HDFn cells were plated onto three T75 tissue culture flasks. When HDFn cells were 70-80% confluent, they were typsinized and collected for electroporation.

Transfection and Cell Culture

MEFs transfection was performed using an Amaxa machine (Lonza) according to the manufacturer's protocol (program A-023). After electroporation, MEFs were seeded in M15 plus LIF on STO feeders. For Tet-On experiments, M15 containing Doxycycline (1.0 µg/ml) was added 24 hours after transfection and was changed every other day. iPSC colonies were usually picked at day 7 to day 10 to 96 well plates and cells were expanded according to standard mouse ES cell culture conditions.

Transfection of HDFn cells was achieved using an Amaxa machine according to the manufacturer's protocol (program U-020). After electroporation, HDFn cells were seeded in M15 plus hLIF on STO feeders. For Tet-On experiments, M15 containing Doxycycline (2.0 µg/ml) was added 24 hours after transfection and was changed every other day. Human iPSC colonies reprogrammed by PB-CAG vectors were usually picked at day 10, and dissociated with trypsin to single cell suspensions before seeding into in 24 well formats. Human iPSC colonies reprogrammed by PB-TRE vectors were usually picked at day 30 (10 days after replating), and dissociated with trypsin to single cell suspensions before seeding in 24-well plates. Stable lines were established from secondary colonies and maintained according to standard mouse ES cell culture conditions.

Mouse and human iPSC colonies were visualized by alkaline phosphatase staining using the Leukocyte Alkaline Phosphatase kit (Sigma).

Bisulfite Genomic Sequencing

Bisulfite treatment was performed using the EpiTect Bisulfite Kit (Qiagen) according to the manufacturer's recommendations. PCR primers are listed in Supplementary Table 5. Amplified products were cloned into pGEM-T-easy (Promega). Randomly selected clones were sequenced with the M13 forward and M13 reverse primers for each promoters.

RT-PCR

RNA was isolated using the RNeasy Mini Kit (Qiagen). The samples were subsequently quantified and treated with gDNA WipeOut. First-strand cDNA was prepared using the QuantiTect Reverse Transcription Kit (Qiagen). For each RT-PCR reaction, we used 50-100 ng of cDNA and primers listed in Supplementary Table 5. Standard PCR conditions were: 94° C. for 30 s, 60° C. for 30 s, 68° C. for 30 s; X 30 cycles. For real-time PCR, we used Taqman Gene Expression Assays. Taqman probes were either purchased from Applied Biosciences (Supplementary Table 6). All quantitative PCR was performed in a 9700HT Fast Real-Time PCR System (Applied Biosciences). Mouse gene expression was determined relative to mouse Gadph using the $\Delta$Ct method. Human gene expression was determined relative to human GADPH gene using the $\Delta$Ct method.

Immunostaining and Flow Cytometry iPSCs growing in 12 well feeder plates were washed with PBS, fixed in 4% PFA/PBS for 10 min at room temperature, permeabilized with 0.3% Triton X-100 in PBS for 10 min, blocked in 5% donkey serum for 1 h, and primary antibody was added overnight at 4° C. Nanog (1:150, Abcam); SSEA-3, SSEA-4, TRA-1-60, TRA-1-81 (1:10, kindly gifts from Dr. Peter W. Andrews). Cells were washed in PBS and secondary antibody (Alexa488 IgG or IgM, 1:1000; Alexa594 IgG, 1:1000) was added and incubated for an hour at room temperature.

Mouse iPSCs growing in 96 well feeder plates were trypsinized and resuspended in M15. iPSCs were spun down at 1,000 rpm for 3 minutes, and the medium was removed by putting the plate upside down on tissue. iPSCs were resuspended in PBS and analyzed by Cytomics FC-500 (Beckman Coulter).

Human iPSCs growing in 6 well plates were typsinized and resuspended in M15. iPSCs were washed once with PBS, spun down and incubated with SSEA-4-FITC, TRA-1-60-PE or TRA-1-81-FITC antibodies (BD Bioscience) for 1 hour. iPSCs were then washed and resuspended in PBS and analyzed by Cytomics FC-500 (Beckman Coulter).

Teratoma Formation

Mouse iPSCs were suspended in M10, and $1\times10^6$ cells were injected subcutaneously into both dorsal flanks of F1 (12955/C57B6) hybrid mice. Teratomas were dissected, fixed overnight in 10% buffered formalin phosphate and embedded in paraffin before sectioning. Human iPSCs ($1\times10^6$) were injected subcutaneously into both dorsal flanks of NSG mice (NOD.Cg-Prkdcscid Il2rgtm1Wjl/SzJ. The Jackson Laboratory). Teratomas were harvested 8 weeks post injection for fixation and sectioning. Sections were stained with haematoxylin and eosin. All animal experiments were performed in accordance with the UK's 1986 Animals Scientific Procedure Act and local institute ethics committee regulations.

Splinkerette PCR

Splinkerette PCR was performed as previously described to determine PB genomic integration sites. TA-cloned PCR products were sequenced at both ends with M13 forward and reverse primers. PB insertion sites were determined using BLAST. Genomic DNA PCR for exogenous factor-removed iPS lines was performed using primers described in Supplementary Table 4.

Statistical Analyses

Data are shown as mean and standard deviation. All statistical analyses were done with Excel 2008 (Microsoft) or Prism (Graphpad).

EXAMPLE 2

Here we report that expressing two new key transcription factors, Rarg and Lrh1, together with four Yamanaka factors, rapidly activates the endogenous Oct4 locus in as few as 3 days and allowed very fast and efficient reprogramming of mouse embryonic fibroblast cells (MEF). The iPS clones produced were of high quality based on morphology and molecular analysis, and were able to differentiate to various cell types in vivo including the germline. When the same strategy was applied to reprogram human neonatal foreskin dermal fibroblast cells (HDFn), we readily obtained human iPS cells that were LIF-dependent, but FGF-independent. Moreover, the human iPS cells proliferated well and could be subcloned at single cell density in regular mouse ES cell culture condition and expanded extensively without any discernible chromosomal abnormality. Our new iPS cell platform thus provides a novel and highly efficient approach to achieve full pluripotency in two mammalian species. The human iPS cells produced are of great resources for exploration of the human genome functions.

A Rarg Dominant-Negative Allele Blocks ES Cell Differentiation

In an effort to identify genes that can block ES cell differentiation upon genetic mutation, we performed a genetic screen in mouse ES cells using the piggyBac DNA transposon (PB) that carries both a strong CAG promoter/enhancer and a pair of splicing acceptors (FIG. 12a). Insertion of this transposon into the mouse genome can either up-regulate genes near the insertion sites or disrupt them, depending on the structure of the insertion allele. To efficiently eliminate differentiated ES cells in the culture, we targeted the Puro-IRES-Egfp cassette to the Rex1 locus (FIG. 12b). Consequently, undifferentiated ES cells would be resistant to Puromycin (Puro) selection and GFP+ in flow cytometry, while differentiated cells would be killed by Puro selection and become GFP− due to rapid lose of Rex1 expression upon differentiation.

A library of mutant ES cells were differentiated with 1.0 µM all-trans retinoic acid (RA) for 4 days and subsequently selected with Puromycin (FIG. 12c). Several Pura$^r$ ES cell clones were identified from independent mutant ES cell pools. Splinkrette PCR analysis identified PB integration sites in genes encoding Rarg, Pparg and Gclc. For Pparg, PB insertion caused over-expression of the entire protein coding sequences. In contrast, Rarg locus had four independent PB insertions, all found in intron 9 (the last intron) (FIG. 12d). These PB insertions caused truncation of Rarg which misses amino acids encoded by exon 10. Over-expressing this truncated Rarg confirmed its ability to block ES cell differentiation induced by RA (FIG. 12e). This truncated Rarg likely functioned as a dominant negative form of wild type Rarg (Rarg-DN). Over-expression of the full length forms of both Rarg and Rara (Rarg-FL and Rara-FL) enhanced differentiation induced by RA, while a reported dominant-negative form of Rara (Rara-DN) (20) could block ES cell differentiation even with high concentration of RA. Rarg and Rara specific antagonists, CD2665 and Ro-41-5253, could also block ES cell differentiation (FIG. 12f). These data thus demonstrated the critical roles of Rarg and Rara in ES cell differentiation.

Signalling Through Rarg Increases Reprogramming Efficiency

We next tested whether the genes identified in our screen might play a role in iPS cell production. In order to directly evaluate the quality of the iPS cells, we targeted a IRES-Puro-Egfp cassette to the 3'UTR of the Oct4 locus in ES cells for MEF cell preparation (FIG. 6a) (57). These cells were green in flow cytometry and proliferate well in 2 µg/mL Puro (FIG. 6b and data not shown).

We cloned the four Yamanaka factors into the PB transposons separately where expression of each cDNA was controlled by the LTR of MSCV (PB-MSCV-cDNAs, FIG. 6c). These four transposons and the PB transposase (PBase) plasmid were subsequently transfected into Oct4-IRES-Puro-Egfp MEFs. iPS cell colonies resembling those of regular ES cells appeared in three weeks. Most iPS colonies survived 1.0 or 1.5 µg/ml Puro but very few were able to grow in 2.0 µg/ml Puro. Moreover, most iPS colonies were GFP-negative, indicating that the endogenous Oct4 locus in these cells was not expressed to the levels in ES cells. Nevertheless, cells of these few iPS colonies that grew in 2.0 µg/mL Puro were largely GFP-positive, with fluorescence intensity comparable to that of the parental Oct4-IRES-Puro-Egfp knock-in ES cells (FIG. 13A). RT-PCR and DMR sequencing confirmed that these iPS clones growing in 2.0 µg/mL Puro were more similar to regular ES cells than those clones selected by 1.0 or 1.5 µg/mL Puro in terms of pluripotent gene expression and DNA methylation at promoters of these genes (data not shown). These results demonstrated and were consistent with many previous studies that most iPS cells induced by the four Yamanaka factors are only partially reprogrammed and the endogenous Oct4 locus was not fully activated. We thus used 2.0 µg/mL or higher concentration of Puro in combination of flow cytometry to quantitatively evaluate iPS cell quality in the subsequent experiments.

We next cloned the full-length forms of Rarg, Rara, Pparg and Gclc, as well as dominant-negative of Rarg and Rara, into the PB-MSCV transposon, in order to investigate their effects on reprogramming mediated by Yamanaka factors. Over-expressing Pparg and Gclc did not appear to affect Yamanaka factors mediated reprogramming of the MEFs (data not shown). Delivery of the Rarg-DN together with the four Yamanaka factors produced slightly more iPS colonies than control (FIG. 13B). Strikingly, however, expression of the Rarg full-length cDNA increased iPS colony number by about 100 folds (FIGS. 13B and 13C). Expressing Rara-FL also significantly increased reprogramming efficiency, although to a less extent than Rarg-FL. In contrast, Rara-DN completely blocks reprogramming induced by Yamanaka factors (FIG. 13B). These data clearly implicated retinoic signalling in reprogramming process.

Similar to low quality iPS cells induced by four Yamanaka factors alone, adding Rarg-FL or Rara-FL over-expression did not obviously improve the iPS cell quality since most colonies were GFP-negative and only few colonies survived 2.0 µg/mL Puro selection. The iPS clone from over-expressing Rarg-DN, on the other hand, had a similar percentage of GFP-positive cells comparable to iPS clones selected with 2.0 µg/mL Puro, even without any selection during the whole reprogramming process (FIG. 13D).

The fact that expressing Rarg-DN improved iPS cell quality whereas Rara-DN over-expression complete blocked iPS process suggests that RA signalling levels are important. We therefore tested whether the expression levels of Rarg will have effects on reprogramming efficiency. A significant decrease of reprogramming efficiency was correlated with the increase of PB-MSCV-Rarg-FL DNA amount (FIG. 13E). Moreover, expressing Rarg-FL using the stronger CAG promoter decreased the reprogramming efficiency to the level of the control where only Yamanaka factors were expressed (data not shown). These results confirmed that the effect of Rarg over-expression on reprogramming is dosage sensitive.

To further investigate the role of Rarg in iPS cells, we tested a synthesized Rarg-specific agonist, CD437, in combination with the four Yamanaka factors, in reprogramming MEFs. Adding CD437 at 100 nM for up to eight day greatly increased the iPS cell colony number. Moreover, the quality of iPS cells, as measured by FACS, was significantly improved (FIG. 13E). However, treatment of the cells using CD437 beyond 8 days (day 1-12) substantially reduced iPS colony number. A Rara-specific agonist Am580 can also improved reprogramming efficiency when administrated for 8 days, but has little effect on the quality of iPS clones (FIG. 13E). These results indicate that Rarg signalling promotes reprogramming at the initial or early stages but excessive Rarg signalling has negative impacts on iPS cells at later stages. Although expressing Rarg-FL or Rara-FL or using their agonists improved reprogramming efficiency, they did not appear to shorten the reprogramming time, because it still took approximately three weeks for the iPS colonies to form.

Rarg and Lrh1 Synergistically Promote Reprogramming

To explore whether the down-regulation of Rarg signalling is the main reason for better quality of Rarg-DN iPS clones. We treated two independent partially reprogrammed clones with an Rarg-specific antagonist, CD2665, with or without 5-Aza. We noticed that 10 µM CD2665 significantly improved the quality of the partially reprogrammed clones, but its effect was more obvious when used together with 5-Aza (FIG. 14A). Nevertheless, the clones were still largely GFP negative after treatment for 4 days. This brought us to propose that down-regulation of Rarg signalling might only be part of the reason why Rarg-DN iPS cells were of much better quality.

In mouse embryonal carcinoma cells (EC), Rarg forms a complex with orphan receptor Sf1 (Nr5a1), which specifically binds a critical RA response element, RAREoct, in the Oct4 promoter and synergistically up-regulates Oct4 expression (59). Since expressing Rarg greatly promoted iPS cell production, we decided to examine whether Sf1 also plays a similar role. Because Sf1 is not normally expressed in mouse ES cells or early mouse embryos, we also included its subfamily member Lrh1 (Nr5a2) in the experiments, which is expressed in both ES cells and early embryos (62).

We therefore cloned both Sf1 and Lrh1 cDNAs into the PB-MSCV transposon respectively and co-transfected with Yamanaka factors into MEFs. As shown in FIG. 14B, expressing Lrh1 improved reprogramming efficiency significantly, but to a less extent as Rarg did. Expressing Sf1 also increased iPS colony numbers, many colonies however appeared to be differentiated (data not shown). Co-expressing Lrh1 and Rarg did not further increase iPS colony number. Surprisingly, many iPS colonies appeared as early as day 10 post transfection instead of the usual three weeks, with morphology almost indistinguishable from wild-type mouse ES cells (data not shown).

To facilitate future excision of exogenous factors carried by the PB transposon, we made a PB-CAG-Oct4-2A-cMyc-2A-Klf4-2A-Sox2 (PB-CAG-OCKS) transposon, where four Yamanaka factors were linked with T2A peptide sequence and expressed from a single CAG promoter. Some iPS colonies induced by PB-CAG-OCKS were visible under microscope within 4-5 days post transfection. However cells in these colonies later became heterogeneous in morphology (FIG. 7B), and were apparently still not fully reprogrammed because most of the colonies (90%) picked at day 10 were sensitive to 2 μg/mL and contained low percentage of GFP positive cells (FIG. 2D). This is consistent with previous publications that it takes a number of passages for the iPS cells to become fully reprogrammed if only Yamanaka factors are used.

We next made a PB-CAG-Rarg-2A-Lrh1 (PB-CAG-RL) transposon to co-express Rarg and Lrh1 from a single promoter. Four days after PB-CAG-OCKS and PB-CAG-RL were co-transfected into MEFs, tiny ES-like colonies became visible under microscope within 4-5 days post transfection. These colonies appeared to be homogenous in morphology and were very similar to regular mouse ES cells in growth (FIG. 7B). Moreover, there were roughly 7 times more iPS cell colonies compared to the control where only PB-CAG-OCKS were transfected. Interestingly, we frequently saw two, four or even eight tiny colonies of same size forming side by side with each other between day 4-6, which merged into one or two big colonies at day 8, reflecting the likely simultaneous reprogramming of daughter cells from one parental MEF cell. Strikingly, almost all these colonies were resistant to 2 μg/mL Puro selection, and consisted of high percentage of GFP positive cells (FIG. 2D), indicating robust Oct4 expression from the endogenous Oct4 locus.

To find out how fast the endogenous Oct4 locus could be activated, we subjected the MEFs under Puro selection at several post-transfection time points. Puro resistant iPS cell colony can be selected out as early as three days after transfection with both PB-CAG-OCKS and PB-CAG-RL (FIG. 14C), thus confirming the rapid activation of the Oct4 locus under this condition. In the control MEFs transfected with PB-CAG-OCKS only, Puro resistant colonies only appeared if Puro selection was started at day 8 or afterwards. Even for these Puro resistant colonies, we usually observed killing of a large portion of cells in the primary colonies and during subcloning, suggesting heterogeneity among these partially reprogrammed clones.

To determine whether continuous expression of exogenous factors was required for establishment of fully reprogrammed iPS clones, we made the PB-TRE-Oct4-2A-cMyc-2A-Klf4-2A-Sox2 (PB-TRE-OCKS) and PB-TRE-Rarg-2A-Lrh1 (PB-TRE-RL) constructs, where expression of the reprogramming factors was induced by Doxycycline (DOX). The two PB transposon constructs, together with PB-CAG-rtTA vector and the PBase plasmid, were co-transfected into MEFs. DOX induction was applied immediately post transfection for 6, 8 or 10 days, we applied 2 μg/mL Puro selection at day 10. Puro-resistant colonies were obtained in MEFs induced with DOX for only 6 days (FIG. 14D), suggesting six days of expression of these six factors was sufficient to activate the endogenous Oct4 locus to a high level. In contrast, in MEFs transfected with PB-TRE-OCKS and PB-CAG-rtTA only, non Puro resistant colonies were recovered under the same DOX induction scheme. Therefore, expression of four Yamanaka factors alone for up to 10 days was not sufficient to fully activate the endogenous Oct4 locus. To further demonstrate the rapid activation of the endogenous Oct4 locus, we repeated the six-factor Tet/On experiment, but treated the MEFs with DOX for only four days post transfection. Immediately after the DOX withdrawal, Puro selection was applied to select cells that had endogenous Oct4 activation. Several Puro resistant colonies appeared which when expanded showed excellent ES cell morphology. These results clearly demonstrated that expressing the six transcription factors led to rapid activation of the endogenous Oct4 locus and to production of high-quality iPS cells.

To find out how much Rarg and Lrh1 was required for iPS cells, we transfected PB-CAG-OCKS into MEFs together with PB transposons carrying Rarg-FL, Rarg-DN, Lrh1 or Rarg-2A-Lrh1 driven by either MSCV or CAG promoters. It became clear that the iPS quality was directly correlated with the promoters used since PB-MSCV-RL did not significantly improve iPS quality (FIG. 14E). Rarg or Lrh1 alone, no matter which promoter was used, did not have any effect on iPS quality. However, Rarg-DN, when driven by MSCV promoter, can significantly improve iPS quality.

We next made PB-CAG-Oct4-2A-cMyc-2A-Rarg-2A-Lrh1-Klf4-2A-Sox2 (PB-TRE-OCRLKS) to express all six transcription factors from a single promoter. This construct gave rise to similar numbers of high quality iPS cells from MEFs within the similar time window. We therefore cloned a MC1-tk cassette into PB-CAG-OCRLKS to form PB-CAG-OCRLKS-MC1-tk transposon. Similar to using PB-CAG-OCRLKS, many iPS cell colonies were visible 4-5 days post transfection into MEFs which were normally picked at day 8. The expanded iPS cells were sensitive to ganciclovir (Ganc) indicating that the MC1-tk cassette was functional. The PB transposon excises from integration sites precisely by PBase and leaves no foot print behind. We thus transiently expressed PBase by transfecting iPS cells with pL623, and subjected the cells to Ganc selection. In general, several hundreds of Ganc resistant colonies were usually obtained from a single transfection. Characterization of these Ganc resistant cells confirmed that these cells were cured of the PB transposon and thus were free of the exogenous transcriptional factors.

iPS Cells Induced by Six Factors are Pluripotent

To further characterize the iPS cells originally produced by expressing the six factors but were free of exogenous factor expression, we performed RT-PCR to detect expression of pluripotent genes in these cells. The iPS cells had robust expression of mouse ES cell pluripotency markers at levels comparable to those in the parental Oct4-IRES-Puro-Egfp ES cells (FIG. 15A). We also examined DNA methylation patterns at promoters of key pluripotency genes, Oct4, Nanog and Rex1. As shown in FIG. 3C, promoters were completely de-methylated in these cells.

The six factor-induced iPS cells were injected subcutaneously into 129/C57B6 hybrid F1 mice to examine their in vivo differentiation potential. All mice developed teratomas in two week's time, and the mice were sacrificed after one month for tumour samples. Under microscope, cell types representing all three germ layers were found in the teratomas (FIG. 15B).

Furthermore, high quality chimeras were readily obtained from blastocyst injection. When chimera mice were backcrossed to albino C57B6 wild-type mice, germline transmission pups which carry agouti coat colour were identified, demonstrating efficient germline contribution of injected iPS cells (FIG. 3E).

Production of High Quality Human iPS Cells Using the Six Factors

Rapid reprogramming of mouse fibroblast cells via efficient induction of the endogenous Oct4 expression prompted us to explore whether RARG and LRH1 could also improve reprogramming efficiency and quality in human. By comparing human, mouse and rat genomic sequences, we identified that the RAR-SF1 binding site, RAREoct, is highly conserved in all three species (FIG. 5A), suggesting that RARG-LRH1 might regulate Oct4 activation in human cells. We constructed PB-CAG transposons carrying the six human factor cDNAs. These PB transposons were able to produce high quality mouse iPS cells rapidly from MEFs, comparable to using mouse cDNAs (data not shown).

We next co-transfected the PB-CAG transposons containing the six human cDNAs, with a PBase plasmid, into human neonatal foreskin dermal fibroblast cells (HDFn). These human fibroblast cells were then cultured in either regular human ES culture media supplemented with bFGF, or in regular mouse ES cell media (M15) supplemented with human leukemia inhibition factor (hLIF). We identified human ES cell like colonies in human ES culture media supplemented with bFGF. Surprisingly, mouse ES-like colonies appeared in M15 plus hLIF media (FIG. 16A). We thus processed these colonies using standard mouse ES cell protocols. The human iPS colonies were dissociated into single cell suspension by trypsin treatment and re-plated onto STO feeder cells. Secondary colonies were able to form and stable lines were readily established in M15+hLIF from half of the primary colonies picked at day 10. In the control group, which only four Yamanaka factors were used, the primary colonies were morphologically different from those generated with six factors (FIG. 16A), we could never establish stable lines from colonies picked at day 10.

Inhibitors of the ERK kinase and GSK3 signalling cascades (2i) support naive pluripotent stem cell growth in vitro (40), but not primed pluripotent stem cells like EpiSCs (57). 2i media has been successfully used to derive ES cells from difficult mouse strains (40), and from rat blastocysts (14, 58). We thus tested whether our human iPS cells were able to survive and proliferate in 2i+hLIF media. As shown in FIG. 16A, human iPS cells proliferated well in 2i+hLIF media and were able to form ES-like colonies from single cells on STO feeders.

To determine the subcloning efficiency of human iPS cells, cells from one clone were dissociated using trypsin and counted. One hundred or one thousand cells were plated to M15+hLIF, 20% KSR (knockout serum replacement)+hLIF or 2i+hLIF culture conditions. Up to 60% could form colonies again in these conditions (cloning efficiency). No obvious difference was found in colony numbers between these three different culture conditions, although the colonies formed in 2i+hLIF were generally smaller (FIG. 16A). We picked secondary colonies, and expanded them either in M15+hLIF or 2i+hLIF. The expanded clones grew normally and kept undifferentiated in both culture conditions. They were able to form tertiary colonies when dissociated and diluted to single cell density, indicating their robustness for extensive manipulation in vitro. The fact that our human iPS cells growing robustly in regular mouse ES cell media indicated that human iPS cells were regulated by the same core molecular regulatory mechanism as in mouse ES cells. Even after extensive culture, the genome of the iPS cells remained intact, as determined by FISH analysis (FIG. 10E).

We further evaluated the human iPS cells by examining expression of key ES cell specific genes. As shown in FIGS. 16B and 16C, these genes were expressed at high levels, and DNA methylation analysis confirmed that the promoters of the key human pluripotency genes were unmethylated. The human iPS cells behave similarly as mouse ES cells and thus hold great promises for genetically manipulating the human genome. To explore this possibility, we first tested PB transposition to introduce exogenous DNA into these cells. We co-transfected a PB-SB-PGK-Neo transposon into human iPS cells together with a PBase plasmid (31). From one electroporation, we can get about 520,000 G418 resistant colonies, which consist of 5% of the surviving cells. This transposition efficiency is comparable to the efficiency observed in mouse ES cells (31).

We subsequently transfected a PB-SB-SA-βgeo trapping transposon and PBase plasmids into human iPS cells. SA-βgeo cassette allows gene trapping in human iPS cells, and thus has the potential to disrupt gene expression at the insertion sites in the genome. From one electroporation, we recovered 9,000 G418 resistant colonies, which represents 0.09% of cells surviving the electroporation. Our human iPS cell lines were derived from foreskin fibroblast cells and therefore were all male. We thus investigated the mutation efficiency of the PB-SB-SA-βgeo transposition at the HPRT locus because loss of HPRT activity could be scored by 6TG resistance. Out of 9,000 G418 resistant colonies, one 6-TG colonies were recovered.

Discussion

Efficient activation of endogenous Oct4 is one of the most important known criteria for somatic cell reprogramming (3) and for successful nuclear transfer (38). During embryonic development, Oct4 locus was gradually silenced by several layers of repression, which include binding of transcription repressors, histone methylation and deacetylation, and de novo DNA methylation (47). Therefore, reprogramming somatic cells to pluripotent state demands peeling off each of these repression layers of Oct4 expression. Two of the Yamanaka factors, Klf4 and cMyc, are known to be involved in chromatin remodelling among other functions (59). Attempts that target histone deacetylation, histone methylation or DNA methylation by small molecule inhibitors have also improved reprogramming efficiency to an extent (51, 35, 13). However, it has not been explored how to promote both detachment of transcriptional repressor complexes such as COUP-TFs and GCNF from Oct4 promoter, and binding of transcriptional activators to Oct4 promoter at the same time. As a result, Oct4 expression in iPS cells using the current platform might not always be restored properly (60).

Biochemical evidence has shown that retinoic acid signalling positively regulate Oct4 expression through RAREoct, a RA-responsive element (RARE) in Oct4 promoter (26). RAR:RXR heterodimers, which specifically binding to RAREoct, are partly responsible for activation of Oct4 transcription in the presence of low concentration of RA (28). During differentiation, orphan receptors ARP-1/COUP-TFII and EAR-3/COUP-TFI induced by high concentration of RA, which has much higher affinity to RAREoct, displace RAR:RXR from RAREoct and actively silence the Oct4 promoter by recruiting co-repressors (28). Overexpression of RAR:RXR heterodimers can overcome repression of Oct4 by COUP-TFs (28).

RAREoct contains a SF1 binding site which is overlapping with RAR recognition site, which provides a second mechanism for RARs to activate Oct4. SF1 and RAR can form a complex that specifically binds to RAREoct and synergistically activate Oct4 (29). Interestingly, neither RAR-SF1 complex formation nor its activation of Oct4 requires RA (29). Moreover, it has been shown that SF1 competes with COUP-TFI for the same cis-acting elements in several other genes (61, 62). Therefore, RAR and SF1/LRH1 complex functions as a positive regulator of Oct4 expression likely through antagonizing COUP-TFs in binding RAREoct.

Taken these published biochemical data and our observation together, we propose a working model of Rarg and Lrh1 in somatic cell reprogramming. When Rarg is expressed alone, it mainly recruits RXR to bind to RAREoct and activates endogenous Oct4 transcription since Lrh1 and Sf1 are not normally expressed in MEFs. However, the relatively low binding affinity of RAR:RXR heterodimers to RAREoct makes it difficult to compete with repressors such as COUP-TFs and GCNF. Consequently, Oct4 is either not fully activated or the activation is not stable. This explains that Rarg over-expression increases reprogramming efficiency, but does not improve iPS cell quality. Co-expressing Rarg and Lrh1 allows Rarg-Lrh1 complex to displace repressors from binding RAREoct and to efficiently activate Oct4 transcription. Subsequently, some coactivators that are known to interact with RAR, such as CBP/p300, P/CAF and SRC1/TIF2 (36), are recruited to Oct4 locus to facilitate further chromatin remodelling. Therefore, the stable occupation of a critical element in Oct4 promoter by Rarg-Lrh1 complex not only up-regulate the transcription level of endogenous Oct4, but also facilitate the remodelling of chromatin structure of Oct4 promoter. Consequently, the most critical hurdle in the somatic cell reprogramming, endogenous Oct4 activation (47), is overcome at a early stage of reprogramming, which dramatically speeds up the reprogramming process and improves iPS cell quality.

Mouse ES cell lines are established from inner cell mass (ICM) of pre-implantation blastocysts and are able to contribute to all lineages of adult mouse tissues. On the other hand, mouse EpiSCs are isolated from post-implantation embryos and can't colonize ICM of a blastocyst, even though they can produce teratomas when injected into immune-deficient mice. EpiSCs possibly represent a different pluripotent cell type which exists at different stages of mouse embryogenesis, and resides in different micro-environments, and is therefore responding to different extrinsic signals from ES cells (63). Since mouse EpiSCs were derived using human ES cell culture media, the existing human ES and iPS cell lines might represent another primed pluripotent state further down the stem cell hierarchy (63). Remarkably, human iPS cell lines reported here grow robustly in mouse ES culture condition and behave similarly to mouse ES cells, indicating a common regulatory for naive pluripotent stem cells in the mouse and human.

In summary, we report here that synergetic interaction of Rarg and Lrh1 in activating the Oct4 locus results in rapid and efficient reprogramming of mouse and human somatic cells. Mouse and human iPS cells produced are of excellent quality with human iPS cells being highly similar to regular mouse ES cells but distinct from existing human ES cells and iPS cells. The robustness of these human iPS cells in growth, expanding and genetically manipulating these cells will make them attractive for exploring genome functions and for generating patient-specific, mutation-free and exogenous factor-free human iPS cells.

Materials and Methods

Plasmid Vector Construction.

To make PB-TRE, PB-MSCV and PB-CAG vectors, the Tet response element (TRE) was amplified from pTight (Clontech), the MSCV LTR was amplified from pMSCV-Neo (Clontech) and the CAGG promoter was amplified from a pBluescript-CAG vector (unpublished data), and cloned into a PB-bpA vector (unpublished data).

The four mouse and human Yamanaka factors were amplified from original retroviral vectors (Addgene) and cloned into the PB-TRE, PB-MSCV and PB-CAG transposon vectors, respectively. Mouse and human Rarg, Lrh1 and Sf1 were amplified from IMAGE clones (Geneservice) and cloned into transposon vectors.

MEF Preparation 12.5 d.p.c. Oct4-IRES-Puro-Egfp embryos were decapitated, eviscerated, dissociated with 0.25% trypsin and plated in M10 (knockout DMEM, 10% foetal bovine serum (FBS), penicillin-streptomycin and glutamax and non-essential amino acids (NEAA)). HEFn was purchased from Invitrogen and maintained in Media 106 supplemented with low serum growth supplement (Invitrogen).

Transfection and Cell Culture

After electroporation, MEFs were seeded in M15 (knockout DMEM, 15% FBS, penicillin-streptomycin, glutamax, β-mercaptoethanol ((βME), NEAA) plus mouse LIF on STO feeder plates. M15 containing doxycycline (1 µg/mL) was added 24 h after transfection and changed daily. iPS Colonies were picked at day 10 in 96 well formats and maintained according to standard mouse ES cell culture conditions.

Transfection of HDFn was performed similarly, except fibroblasts were seeded in M15 plus human LIF. M15 containing doxycycline (2 µg/mL) was added 24 h after transfection and changed daily. Colonies was picked at day 10 in 24 well formats. Clones that generated secondary colonies were expanded and maintained according to standard mouse ES cell culture conditions.

Splinkerette PCR

Splinkerette PCR to determine PB genomic integration sites was performed as described. TA-cloned PCR products were sequenced bidirectionally with M13 forward and reverse primers. PB insertion loci were determined using BLAST. Genomic PCR on factor-removed PBiPS lines was performed using primers described.

RT-PCR

RNA was isolated using the RNeasy Mini Kit (Qiagen), quantified and treated with gDNA WipeOut and cDNA prepared with the QuantiTect Reverse Transcription Kit (Qiagen). For each RT-PCR reaction, we used 50-100 ng of cDNA and primers listed. Standard PCR conditions were: 94° C. for 30 s, 58-62° C. for 30 s, 72° C. for 15-30 s; X 30-35 cycles.

Immunostaining and Flow Cytometry

Cells were grown on 12 well feeder plate. Cells were washed with PBS, fixed in 4% PFA/PBS for 10 min at 25° C., permeabilized with 0.3% Triton X-100 in PBS for 10 min at 25° C., blocked in 5% donkey serum for 1 h, and primary antibody was added overnight at 4° C. Samples were washed in PBS and secondary antibody (cy3 IgG, 1:1,000; Alexa488 IgG or IgM, 1:400; Alexa594 IgG, 1:200) was added for 1 h at 25° C.

In Vitro Differentiation Assays

Human PB-iPS lines were dissociated and used to generate embryoid bodies by aggregation in AggreWell 400 plates (StemCell Technologies) in M15 without hLIF. After 14 days growth, embryoid bodies were plated on Matrigel-coated coverslips or 4 chamber slides. Immunohistochemistry was performed after an additional 10 days culture.

Teratoma Formation

Cell lines were suspended in DMEM containing 10% FBS, and 100 ml ($1\times10^6$ cells) injected subcutaneously into both dorsal flanks of nude mice (CByJ.Cg-Foxn1nu/J) anaesthetized with isoflurane. Six weeks after injection, teratomas were dissected, fixed overnight in 10% buffered formalin phosphate and embedded in paraffin. Sections were stained with haematoxylin and eosin.

FIGURE LEGENDS

FIG. 1. RA signalling in reprogramming. A. Schematic of the reprogramming strategy by piggyBac (PB) transposition. Oct4 reporter MEFs were transfected with the PB-MSCV-cDNA transposon and transposase plasmids, and were plated directly onto STO feeders. ES-like colonies usually appeared in three weeks. M10 and M15 are media for MEFs and ES cells, respectively. B-C. Expressing Rara or Rarg, together with the four Yamanaka factors, drastically promoted reprogramming while inhibiting RA signalling by expressing Rara-DN blocked reprogramming. iPSC colonies were visualized by alkaline phosphatase staining. The reprogramming control was PB-PGK-Neo plus Yamanaka factors. : P<0.005; *: P<0.0005. FL: full-length cDNA; DN: dominant-negative form. D. Temporal requirement of RA signalling in reprogramming. Agonist of Rarg (CD437) was added at various stages of reprogramming. Day 1-4: Agonist added from day-1 to day-4 after transfection. DMSO, solvent for CD437, was added in the control plate. E-F. Expression of pluripotency genes (E) and DNA methylation at Nanog and Rex1 loci (F) in reprogrammed cells. Only cells resistant to 2.0 μg/ml Puro selection were fully reprogrammed iPSCs, whereas those resistant only to 1.0 μg/ml Puro were partially reprogrammed. ES: Oct4-IRES-Puro-Egfp knock-in ES cells; MEF: Oct4-IRES-Puro-Egfp reporter MEF cells. G. Improvement of iPSC quality by Rarg agonist CD437. Quality of iPSCs (CD437 from day 1-4) was analyzed by GFP expression from the Oct4 locus by flow cytometry.

In the histogram of FIG. 1 (D), the first bar represents Day 1-4, the second bar represents Day 1-8, the third bar represents Day 1-12, the fourth bar represents day 4-8 and the fifth bar represents day 4-12.

FIG. 2. Rarg (R) and Lrh-1 (L) synergistically promote reprogramming. A. Schematic of the Tet-On reprogramming strategy. Once MEFs were transfected with the PB-TRE-cDNA transposon, PB-CAG-rtTA, and PB transposase plasmids, they were plated onto STO feeders. Dox (1.0 μg/ml) was added 24 hours post transfection. At 4, 6, 8 and 10 days after transfecton, Dox was removed from the media with Puromycin selection (2.0 μg/ml) being applied immediately to select for cells with fully activated Oct4 locus. Puromycin kills MEFs and ES cells within 24 hours. B. Four-day expression of the six factors (TRE-OCKS and TRE-RL) was sufficient to fully activate endogenous Oct4 expression for obtaining Dox-independent iPSCs. In contrast, Puro$^r$ iPSC colonies did not appear until at least 12 days of expressing the four Yamanaka factors (TRE-OCKS). C. Images of colonies 6 days post transfection. Scale bars, 10.0 μm. D. Co-expressing Rarg and Lrh-1 (RL), but not Rarg or Lrh-1 individually, improved iPSC quality. Individual iPSC colonies were picked at day-10 post transfection and grew in 96-well plates for GFP expression in flow cytometry. ***: p<0.0005. E. Synergistic interaction of Rarg and Lrh-1 to activate the Oct4 promoter in the luciferase reporter assay. The luciferase reporter linked to the Oct4 promoter was transfected into MEFs. Luciferase activity was measured 48 hours later. Expression of luciferase was normalized to the negative control in which the PB-Neo plasmid was used in transfection. Bars are mean±SD.

FIG. 3. Characterization of Dox-independent mouse iPSCs. A-B. Robust expression of pluripotency genes in mouse iPSCs. A. Immunostaining of iPS20-A1 cells to detect Oct4 and Nanog. B. qRT-PCR of Oct4, Nanog and Rex1 in mouse iPSCs, parental MEFs and wild type ES cells. Expression was relative to Gapdh and normalized against gene expression in parental Oct4 reporter mouse ES cells. The three iPSC lines shown were produced by 4 days (A1), 6 days (B1) or 8 days (C1) of Dox induction of the six factors (OCKS+RL). MEF: Oct4-IRES-Puro-Egfp reporter MEF cells; ES cells: Oct4-IRES-Puro-Egfp knock-in ES cells. C. Nearly complete de-methylation in the promoters of Oct4 and Nanog in the iPSCs (iPS20-A1). D. Teratomas derived from the iPSCs contained cells types of all three germ layers. Panels show chondrocytes (top left), keratinocytes (top right), gut-like epithelial cells (bottom left) and neuronal cells (bottom right). All photographs were taken at the same magnification (×200). E. Contribution of iPSCs to the germline in chimeras. The chimeras were crossed to wild type C57BL6 females (albino). Germline transmission pups were the agouti ones.

In each histogram in FIG. 3 (B), the first bar represents mESC, the second bar represents MiPS20-A1, the third bar represents MiPS20-B2 and the fourth bar represents MiPS20-C1.

FIG. 4. Reprogramming MEFs to ground state iPSCs in serum-free, feeder-free conditions. A. Number of AP$^+$ colonies reprogrammed with either PB-TRE-OCKS (4F), or PB-TRE-OCKS plus PB-TRE-RL (6F). Post transfection MEFs were seeded into gelatinized 6-well plates ($2\times10^5$/well) in M15/LIF/Dox for one day, switched to N2B27/LIF/Dox for up to 17 days. B. Gene expression analysis of iPSCs by qRT-PCR. Expression was relative to Gapdh and normalized to wild type ES cells. Bars are mean±SD. C. Immunostaining of iPSCs (6F) for Nanog and SSEA-1 expression. D. In vitro differentiation of iPSCs (6F) to cell type representing the three germ layers detected by immunostaining. Antibodies: Tuj, neuron-specific class III 6-tublin; SMA, smooth muscle α-actin; AFP, α-fetoprotein.

In each histogram in FIG. 4 (B), the first bar represents ES, the second bar represents 4FiPS, the third bar represents 6F-iPS and the fourth bar represents MEF.

FIG. 5. Production and characterization of Dox-independent unique human iPSCs. A. Conservation of RAREoct sequence in several mammalian species. B. Reprogramming HDFn cells using the Tet-On six-factor platform. PB-TRE-cDNA transposon, PB-CAG-rtTA and transposase plasmids were transfected into HDFs which were plated onto STO feeders. Dox (2.0 µg/ml) was added 24 hours post transfection. Dox induction usually lasted for 15-20 days. Colonies were picked for expansion at up to 30 days after transfection. Alternatively, immediately once Dox was removed, colonies were trypsinized and re-plated to a new feeder plate for secondary colony formation. C. Typical human iPSC colony morphology and AP staining. Scale bars: 10.0 µm. D. qRT-PCR analysis of pluripotency genes in parental HDFn, human iPSCs and H1 hESC cells. HiPS15-5 and -10 were two Dox-independent iPSC lines generated from one transfection. E. Immunostaining of human iPSCs for ES cell surface markers and pluripotency factors. F. In vitro differentiation of human iPSCs. Antibodies: Tuj, neuron-specific class III β-tublin; SMA, smooth muscle α-actin; AFP, α-fetoprotein. G. Teratomas differentiated from human iPSCs. Left panel, cartilage (mesoderm); middle panel, neural tissues (ectoderm); ciliated glandular epithelia (endoderm). All photographs were taken at the same magnification (×200). H. Signalling dependency of human iPSCs measured by gene expression (qRT-PCR). Robust expression of pluripotency genes in the presence of FGF receptor inhibitor (FGFRi), but not if a JAK inhibitor (JAKi) was added. H1 hESC cells growing in KSR-FGF2 (bFGF) or in KSR-2i-LIF media (2i/LIF) were used as the controls. I. Gene expression changes in human iPSCs growing in different conditions. The FGF-adapted iPSCs were rapidly differentiated if cultured in 2i/LIF media again. Expression of OCT4 and NANOG was lost in these cells with concomitant expression of SOX17 and SOX1. Quantitative analysis of gene expression was performed relative to GADPH. Expression in H1 hESC cells growing in FGF2 media was used as the control. Bars are mean±SD.

In the first three histograms in FIG. 5 (D), the first bar represents HihESC, the second bar represents HiPS15-5 and the third bar represents HiPS15-10. In the fourth histogram in FIG. 5 (D), the first bar represents HDFn, the second bar represents HihESC, the third bar represents HiPS15-5 and the fourth bar represents HiPS15-10.

In each histogram in FIG. 5 (H), where present, the first bar represents FGF2 in H1 hESC cells, the second bar represents 2i/LIF in HiPS15-10, the third bar represents 2i/LIF to FGF2 in HiPS15-10 cells, and the fourth bar represents FGF2 to 2i/LIF in HiPS15-10 cells.

In each histogram in FIG. 5 (I), where present, the first bar represents FGF2 in H1 hESC cells, the second bar represents 2i/LIF in H1 hESC cells, the third bar represents 2i/LIF in HiPS15-10, the fourth bar represents 2i/LIF/BMP4 in HiPS15-10 cells, the fifth bar represents 2i/LIF/JAKi in HiPS15-10 cells and the sixth bar represents 2i/LIF/FGFRi in HiPS15-10 cells.

FIG. 6. A. PB transposons carrying transcription factor cDNAs. PB: piggyBac transposon; TR: terminal repeats of the PB; MSCV: LTR of Murine Stem Cell Virus; CAG: CAG promoter; TRE: Tetracycline response element; pA: polyadenylation signalling sequence. B. The Oct4-IRES-Puro-Egfp knock-in allele. The IRES-Puro-Egfp cassette was targeted to the 3'UTR of the Oct4 locus to monitor and select for activation of the locus. C. Flow cytometric analysis of Oct4-IRES-Puro-Egfp MEF cells and Oct4-IRES-Puro-Egfp knock-in ES cells. Only the targeted ES cells were green in the analysis. D. Increased amount of Rarg-carrying transposon DNA in transfection reduced reprogramming efficiency of OCKS. Control: OCKS alone without any PB-MSCV-Rarg. E. Flow cytometric analysis of reprogrammed mouse cells survived two Puromycin concentrations. Most 1.0 µg/ml Puro$^r$ colonies did not express GFP. On the other hand, reprogrammed cells survived 2.0 µg/ml Puromycin selection were all GFP$^+$. Flow cytometric analysis was directly performed using cells growing in 96-well plates.

FIG. 7. Rarg and Lrh-1 synergistically promotes reprogramming. A. PB transposons carrying multiple cDNAs linked by the DNA encoding 2A, the foot-and-mouth disease virus 2A self-cleaving peptide. CAG: the CAG promoter; pA: polyadenylation signalling sequence; rtTA, the reverse tetracycline response transcriptional activator (rtTA); TRE: Tetracycline response element. B. Typical iPSC colonies reprogrammed using PB-CAG-OCKS alone (top 2 panels) or together with PB-CAG-RL (bottom 2 panels). Images were taken ten days after transfection. C. Alkaline phosphatase staining of iPSC colonies 10 days after transfection. The six factors (CAG-OCKS and CAG-RL) produced up to 20 times more colonies (right plate) than if only the four Yamanaka factors (CAG-OCKS) were used. D. Diagram of the DNA construct for the luciferase reporter assay. A 460-bp Oct4 promoter DNA fragment flanking the RAREoct site was cloned in front of the luc2 coding sequence.

FIG. 8. Characterization of mouse iPSCs for pluripotency. A. Immunostaining of iPS20-A1 cells to detect SSEA1 and Nanog. B. Robust expression of endogenous pluripotency genes in mouse iPSCs. Expression was detected by RT-PCR with α-actin as the PCR control. iPS20-A1, B1 and C1 were three iPS cell lines generated by 4 days (A1), 6 days (B1) or 8 days (C1) of Dox induction of the six factors (OCKS+RL). MEF: Oct4-IRES-Puro-Egfp knock-in MEFs; ES: Oct4-IRES-Puro-Egfp knock-in ES cells. C. RT-PCR analysis of expression of the exogenous reprogramming factors in mouse iPSC lines. Control, mouse iPSCs growing in the presence of Dox to induce exogenous factor expression; ES, parental Oct4-IRES-Puro-Egfp knock-in ES cells. Oct4-cMyc-exogenous, cMyc-Klf4-exogenous, Klf4-Sox2-exogenous were three primer pairs detecting junction fragments between cDNAs in PB-TRE-OCKS construct. Rarg-Lrh-1-exogenous was a pair of primers detecting flanking sequence in PB-TRE-RL construct. Expression of exogenous factors was undetectable in most iPSC lines.

FIG. 9. Reprogramming of MEFs in the feeder-free and serum-free conditions. A. MEFs were transfected with either PB-TRE-OCKS (4-factor) or PB-TRE-OCKS plus PB-CAG-RL (6-factor), and were plated in N2B27 plus LIF media with Dox for the indicated days. Once primary colonies were picked, they were cultured in 2i/LIF media. No colonies were obtained from expressing the 4 factors with 8 days Dox treatment. In another experiment, 2i/LIF media was directly used to culture freshly transfected MEFs. Dox was added for up to 17 days in order for any colony from expressing OCKS to appear. However, colonies were obtained only when six exogenous factors were used. B. Hematoxylin and eosin stained parafin sections of teratomas contained derivatives of all three germ layers. Epidermal differentiation (with the formation of keratin perls) and neural differentiation (with formation of rosettes and neural tubes) are shown on the two top row figures. Endodermal derivatives (indicated with arrows) are represented by glandular structures lined by goblet cells, enterocyte-like cells and Paneth cells. Mesodermal derivatives consist of cartilage, immature adipose tissue and muscle. All photographs were taken at the same magnification (200×).

FIG. 10. Production of unique human iPSCs cells with the six-factor platform (CAG promoter version). A. Human iPSCs colonies formed in M15 plus LIF media or in 2i/LIF media, which resembled regular mouse ES cell colonies. Top left panel, typical colony reprogrammed with the four Yamanaka factors; top right panel, typical human iPSC colony reprogrammed using the six factors. Images were taken ten days post transfection. Bottom left panel, secondary colonies after primary iPSC colonies were dissociated and re-plated onto feeder cells; bottom right panel, a typical human iPSC colony after sub-cloning at single cell density.
B. Expression of endogenous pluripotency protein in human iPSCs detected by immuno-staining. C. Expression of pluripotency genes in human iPSCs detected by RT-PCR. HiPS1-3 and 4, HiPS6-4 and 16 were four independent iPSC lines. HDF: human dermal fibroblast cells; hESC: human ES cells. D. Differentiation of human iPSCs to cell types of the three germ layers in teratomas. Top left panel, neural tissue with occasional rosettes (arrow); top right, fibromuscular fibers (arrows); bottom left, loose mesenchyme (arrow); bottom right panel, ciliated glandular epithelia (arrow). All photographs were taken at the same magnification (×200). E. Normal karyotype in human iPSCs after extensive passaging (>20 passages). Top panel, DAPI; bottom panel, MFISH. F. Y chromosome genotyping of human iPSCs confirmed the HDFn origin of human iPSCs. Sixteen human Y chromosome markers were used for the genotyping.

FIG. 11. Characterization of unique human iPSCs produced using the six-factor Tet-On system (Dox-independent). A. RT-PCR analysis of gene expression in human iPSCs with human GADPH as the control. HDF: human dermal fibroblast cells; hESC: H1 human ES cells. B. FACS analysis of human iPSCs for SSEA-4, Tra-1-60 and Tra-1-81 expression. Left panel, HDF control which did not express SSEA-4, TRA-1-60 or TRA-1-81. C. RT-PCR analysis of exogenous factor expression in human iPSCs. Control, iPSCs growing in Dox to induce exogenous factor expression; hESC, H1 human ES cells. The two lines did not have obvious expression of exogenous OCT4, SOX2 and MYC, KLF4 after PCR amplification. D. Human iPSCs had the normal karyotype after extensive in vitro culturing (>20 passages). Top panel, DAPI; bottom panel, MFISH. E. Insertion of the gene-trap PB transposon into the HPRT locus that disrupted HPRT activity in human iPSCs. A gene-trap PB transposon integration was found in intron 2 of the HPRT locus. Bottom panel, sequences of the PB transposon and HPRT genomic DNA junctions.

FIG. 12. A Rarg Dominant-negative Allele Blocks ES Cell Differentiation
A. Schematic of the PB transposon that carries both a strong CAG promoter/enhancer and a pair of splicing acceptors.
B. Diagram of the Rex1-Puro-IRES-Egfp knock-in mouse ES cell line.
C. Strategy of the genetic screen in mouse ES cells to identify mutants that can block ES cell differentiation induced by retinoic acid.
D. Four independent mutations at the Rarg locus identified in the genetic screen.
E. RA induced ES cell differentiation blocked by over-expression of Rarg or Rara dominant form.
F. RA induced ES cell differentiation blocked by Rarg- or Rara-specific antagonists.

In each histogram in FIG. 12 (E), where present, the first bar represents PB-MSCV-Rara-DN, the second bar represents PB-MSCV-Rarg-DN, the third bar represents PB-PGK-Neo, the fourth bar represents PB-MSCV-Rara-FL and the fifth bar represents PB-MSCV-Rarg-FL.

In each histogram in FIG. 12 (F), where present, the first bar represents RA alone, the second bar represents RA+Ro-41-5253 and the third bar represents RA+CD2665.

FIG. 13. RA signalling plays critical roles in reprogramming of mouse MEFs to iPS cells.
A. Higher quality of iPS cells was co-related to surviving higher concentrations of Puromycin.
B. Drastic increase of reprogramming efficiency by over-expression of Rarg-FL.
C. iPS cell culture plate showing Rarg increasing reprogramming efficiency. Cells were stained with crystal violet.
D. Over-expression of Rarg-DN also improves the quality of iPS clones but reduces reprogramming efficiency.
E. Dose of Rarg affects reprogramming efficiency.
F. Reprogramming efficiency increased by Rarg- or Rara-specific agonists.
G. Rarg-specific agonist improves the quality of iPS cells.

In the histogram of FIG. 13 (F), the first bar represents Day 1-4, the second bar represents Day 1-8, the third bar represents Day 1-12, the fourth bar represents day 4-8, the fifth bar represents day 4-12 and the sixth bar represents day 8-12.

FIG. 14. Rarg and Lrh1 work synergistically to promote reprogramming
A. Rarg-specific antagonist treatment can improve the quality of partially reprogrammed iPS clone.
B. Over-expression of Lrh1 promotes reprogramming.
C. Rapid reprogramming of MEFs by the six factors as indicated by the much early appearances of Puro resistant iPS cell colonies.
D. Expression of Rarg and Lrh1 was required for rapidly achieving fully reprogrammed pluripotency.
E. Dose of Rarg and Lrh1 expression is critical for quality of iPS cells.

In the histogram of FIG. 14 (A), In the histogram of FIG. 13 (F), the first bar represents Day 1, the second bar represents Day 2, the third bar represents Day 3 and the fourth bar represents Day 4.

FIG. 15. High quality of iPS Cells reprogrammed by Six Factors
A. Mouse iPS cells produced using Rarg and Lrh1 had robust expression of ES cell pluripotency markers.
B. The six factor-induced mouse iPS cells could contribute to all lineages in teratoma.

FIG. 16. Production of High Quality Human iPS cells using the Six Factors
A. Human iPS cell colonies produced in M15 plus hLIF media (top panel). HUman iPS cell colonies expanded in 2i plus hLIF culture condition (bottom panel).
B. Human iPS cells express high level of OCT4 and NANOG.
C. RT-PCR analysis confirms high levels of expression of pluripotency gene in human iPS cells. 4-1, 4-2, 4-3, and 4-5 are human iPS cells. ES: human ES cell control.

REFERENCES

1. K. Takahashi, S. Yamanaka, *Cell* 126, 663 (Aug. 25, 2006).
2. K. Okita, T. Ichisaka, S. Yamanaka, *Nature* 448, 313 (Jul. 19, 2007).
3. M. Wernig et al., *Nature* 448, 318 (Jul. 19, 2007).
4. J. Hanna et al., *Cell* 133, 250 (Apr. 18, 2008).
5. T. Aoi et al., *Science* 321, 699 (Aug. 1, 2008).
6. M. Wernig et al., *Nat Biotechnol* 26, 916 (August, 2008).
7. K. Takahashi et al., *Cell* 131, 861 (Nov. 30, 2007).

8. I. H. Park et al., *Nature* 451, 141 (Jan. 10, 2008).
9. J. Yu et al., *Science* 318, 1917 (Dec. 21, 2007).
10. J. C. Heng et al., *Cell stem cell* 6, 167 (February 5).
11. J. Silva et al., *PLoS biology* 6, e253 (Oct. 21, 2008).
12. D. Huangfu et al., *Nat Biotechnol* 26, 795 (July, 2008).
13. Y. Shi et al., *Cell Stem Cell* 2, 525 (Jun. 5, 2008).
14. J. K. Ichida et al., *Cell stem cell* 5, 491 (Nov. 6, 2009).
15. A. Marson et al., *Cell stem cell* 3, 132 (Aug. 7, 2008).
16. H. Hong et al., *Nature* 460, 1132 (Aug. 27, 2009).
17. J. Hanna et al., *Nature* 462, 595 (Dec. 3, 2009).
18. J. Han et al., *Nature* 463, 1096 (Feb. 25, 2010).
19. M. J. Boland et al., *Nature* 461, 91 (Sep. 3, 2009).
20. L. Kang, J. Wang, Y. Zhang, Z. Kou, S. Gao, *Cell stem cell* 5, 135 (Aug. 7, 2009).
21. M. Stadtfeld et al., *Nature* 465, 175 (May 13).
22. A. Meissner, M. Wernig, R. Jaenisch, *Nat Biotechnol* 25, 1177 (October, 2007).
23. M. Nakagawa et al., *Nature biotechnology* 26, 101 (January, 2008).
24. J. Yu, J. A. Thomson, *Genes & development* 22, 1987 (Aug. 1, 2008).
25. K. Niederreither, P. Dolle, *Nature reviews* 9, 541 (July, 2008).
26. E. Pikarsky, H. Sharir, E. Ben-Shushan, Y. Bergman, *Mol Cell Biol* 14, 1026 (February, 1994).
27. I. Sylvester, H. R. Scholer, *Nucleic Acids Res* 22, 901 (Mar. 25, 1994).
28. E. Ben-Shushan, H. Sharir, E. Pikarsky, Y. Bergman, *Mol Cell Biol* 15, 1034 (February, 1995).
29. E. Barnea, Y. Bergman, *J Biol Chem* 275, 6608 (Mar. 3, 2000).
30. M. Wernig, A. Meissner, J. P. Cassady, R. Jaenisch, *Cell stem cell* 2, 10 (Jan. 10, 2008).
31. W. Wang et al., *Proc Natl Acad Sci USA* 105, 9290 (Jul. 8, 2008).
32. H. Niwa, J. Miyazaki, A. G. Smith, *Nat Genet* 24, 372 (April, 2000).
33. S. Tsai et al., *Genes & development* 6, 2258 (December, 1992).
34. M. Gianni, S. Zanotta, M. Terao, S. Garattini, E. Garattini, *Biochemical and biophysical research communications* 196, 252 (Oct. 15, 1993).
35. P. Gu et al., *Mol Cell Biol* 25, 3492 (May, 2005).
36. M. Stadtfeld, N. Maherali, D. T. Breault, K. Hochedlinger, *Cell stem cell* 2, 230 (Mar. 6, 2008).
37. T. Brambrink et al., *Cell stem cell* 2, 151 (Feb. 7, 2008).
38. M. Boiani, S. Eckardt, H. R. Scholer, K. J. McLaughlin, *Genes & development* 16, 1209 (May 15, 2002).
39. Q. L. Ying, J. Nichols, I. Chambers, A. Smith, *Cell* 115, 281 (Oct. 31, 2003).
40. Q. L. Ying et al., *Nature* 453, 519 (May 22, 2008).
41. M. Buehr et al., *Cell* 135, 1287 (Dec. 26, 2008).
42. H. M. Yang et al., *J Cell Biochem* 101, 1198 (Aug. 1, 2007).
43. F. Ishikawa et al., *Blood* 106, 1565 (Sep. 1, 2005).
44. J. A. Thomson et al., *Science* (New York, N.Y. 282, 1145 (Nov. 6, 1998).
45. M. Amit et al., *Dev Biol* 227, 271 (Nov. 15, 2000).
46. T. Perlmann, R. M. Evans, *Cell* 90, 391 (Aug. 8, 1997).
47. K. Hochedlinger, K. Plath, *Development* 136, 509 (February, 2009).
48. http://biogps.gnf.org/.
49. J. Hanna et al., *Proceedings of the National Academy of Sciences of the United States of America*, (May 4, 2010).
50. C. Buecker et al., *Cell stem cell* 6, 535 (Jun. 4, 2010, 2010).
51. T. S. Mikkelsen et al., *Nature* 454, 49 (Jul. 3, 2008).
52. A. Meissner, M. Wernig, R. Jaenisch, *Nat Biotechnol* 25, 1177 (October, 2007).
53. M. J. Evans, M. H. Kaufman, *Nature* 292, 154 (Jul. 9, 1981).
54. A. G. Smith et al., *Nature* 336, 688 (Dec. 15, 1988).
55. I. G. Brons et al., *Nature* 448, 191 (Jul. 12, 2007).
56. P. J. Tesar et al., *Nature* 448, 196 (Jul. 12, 2007).
57. G. Guo et al., *Development* 136, 1063 (April, 2009).
58. P. Li et al., *Cell* 135, 1299 (Dec. 26, 2008).
59. S. Yamanaka, *Cell Stem Cell* 1, 39 (Jun. 7, 2007).
60. N. Feldman et al., *Nat Cell Biol* 8, 188 (February, 2006).
61. R. N. Yu, M. Ito, J. L. Jameson, *Mol Endocrinol* 12, 1010 (July, 1998).
62. K. Zeitoun, K. Takayama, M. D. Michael, S. E. Bulun, *Mol Endocrinol* 13, 239 (February, 1999).
63. J. Nichols, A. Smith, *Cell Stem Cell* 4, 487 (Jun. 5, 2009).
64. Wagner R T, Xu X, Yi F, Merrill B J, Cooney A J. 2010. Canonical Wnt/beta-Catenin Regulation of Liver Receptor Homolog-1 (Lrh-1) Mediates Pluripotency Gene Expression. Stem Cells.

TABLE 1

| Sequence | Model Name | Position | Strand |
| --- | --- | --- | --- |
| GXP_1805437 [GXP_1805437] (1-601) Slco2a1, GXL_555, GeneID: 24059, *Mus musculus* chr. 9 solute carrier organic anion transporter family, member 2a1 | RXRF_SF1F_02 | 328-355 | (+) |
| GXP_2043001 [GXP_2043001] (1-601) Gpr156, GXL_13708, GeneID: 239845, *Mus musculus* chr. 16 G protein-coupled receptor 156 | RXRF_SF1F_02 | 51-78 | (+) |
| GXP_48251 [GXP_48251] (1-601) Pgm1, GXL_39900, GeneID: 66681, *Mus musculus* chr. 5 phosphoglucomutase 1 | RXRF_SF1F_02 | 273-246 | (−) |
| GXP_54608 [GXP_54608] (1-896) Dna2, GXL_45025, GeneID: 327762, *Mus musculus* chr. 10 DNA replication helicase 2 homolog (yeast) | RXRF_SF1F_02 | 863-890 | (+) |
| GXP_70835 [GXP_70835] (1-689) Cox6a2, GXL_58865, GeneID: 12862, *Mus musculus* chr. 7 cytochrome c oxidase, subunit VI a, polypeptide 2 | RXRF_SF1F_02 | 94-67 | (−) |

TABLE 1-continued

| Sequence | Model Name | Position | Strand |
|---|---|---|---|
| GXP_76405 [GXP_76405] (1-1461) Pfn4, GXL_63527, GeneID: 382562, *Mus musculus* chr. 12 profilin family, member 4 | RXRF_SF1F_02 | 1042-1015 | (−) |
| GXP_76829 [GXP_76829] (1-1168) Slc43a1, GXL_63856, GeneID: 72401, *Mus musculus* chr. 2 solute carrier family 43, member 1 | RXRF_SF1F_02 | 38-11 | (−) |
| GXP_84648 [GXP_84648] (1-674) Cd209f, GXL_70439, GeneID: 69142, *Mus musculus* chr. 8 CD209f antigen | RXRF_SF1F_02 | 173-146 | (−) |
| GXP_92569 [GXP_92569] (1-781) Trpv2, GXL_77017, GeneID: 22368, *Mus musculus* chr. 11 transient receptor potential cation channel, subfamily V, member 2 | RXRF_SF1F_02 | 124-97 | (−) |
| GXP_1248142 [GXP_1248142] (1-876) Hrh1, GXL_88265, GeneID: 15465, *Mus musculus* chr. 6 histamine receptor H1 | RXRF_SF1F_02 | 759-732 | (−) |
| GXP_105499 [GXP_105499] (1-601) Ube4b, GXL_88402, GeneID: 63958, *Mus musculus* chr. 4 ubiquitination factor E4B, UFD2 homolog (*S. cerevisiae*) | RXRF_SF1F_02 | 520-547 | (+) |
| GXP_407485 [GXP_407485] (1-601) Chst3, GXL_96707, GeneID: 53374, *Mus musculus* chr. 10 carbohydrate (chondroitin 6/keratan) sulfotransferase 3 | RXRF_SF1F_02 | 94-121 | (+) |
| GXP_158497 [GXP_158497] (1-1378) Mesp1, GXL_132109, GeneID: 17292, *Mus musculus* chr. 7 mesoderm posterior 1 | RXRF_SF1F_02 | 46-19 | (−) |
| GXP_1803377 [GXP_1803377] (1-603) Anpep, GXL_132245, GeneID: 16790, *Mus musculus* chr. 7 alanyl (membrane) aminopeptidase | RXRF_SF1F_02 | 240-213 | (−) |
| GXP_1799422 [GXP_1799422] (1-603) Nup210l, GXL_133945, GeneID: 77595, *Mus musculus* chr. 3 nucleoporin 210-like | RXRF_SF1F_02 | 325-298 | (−) |
| GXP_2045579 [GXP_2045579] (1-601) Muc1, GXL_134083, GeneID: 17829, *Mus musculus* chr. 3 mucin 1, transmembrane | RXRF_SF1F_02 | 87-114 | (+) |
| GXP_1806208 [GXP_1806208] (1-601) Rs1, GXL_145407, GeneID: 20147, *Mus musculus* chr. X retinoschisis (X-linked, juvenile) 1 (human) | RXRF_SF1F_02 | 300-330 | (+) |
| GXP_2047904 [GXP_2047904] (1-601) Pde8a, GXL_153622, GeneID: 18584, *Mus musculus* chr. 7 phosphodiesterase 8A | RXRF_SF1F_02 | 126-153 | (+) |
| GXP_816489 [GXP_816489] (1-601) Arfgef2, GXL_169927, GeneID: 99371, *Mus musculus* chr. 2 ADP-ribosylation factor guanine nucleotide-exchange factor 2 (brefeldin A-inhibited) | RXRF_SF1F_02 | 166-139 | (−) |
| GXP_1460689 [GXP_1460689] (1-601) Gtpbp5, GXL_169951, GeneID: 52856, *Mus musculus* chr. 2 GTP binding protein 5 | RXRF_SF1F_02 | 582-555 | (−) |
| GXP_433031 [GXP_433031] (1-601) Ccdc21, GXL_181575, GeneID: 70012, *Mus musculus* chr. 4 coiled-coil domain containing 21 | RXRF_SF1F_02 | 15-42 | (+) |
| GXP_446388 [GXP_446388] (1-601) Prtg, GXL_183874, GeneID: 235472, *Mus musculus* chr. 9 protogenin homolog (*Gallus gallus*) | RXRF_SF1F_02 | 127-154 | (+) |
| GXP_1801525 [GXP_1801525] (1-601) Trpv4, GXL_210485, GeneID: 63873, *Mus musculus* chr. 5 transient receptor potential cation channel, subfamily V, member 4 | RXRF_SF1F_02 | 137-164 | (+) |

TABLE 1-continued

| Sequence | Model Name | Position | Strand |
|---|---|---|---|
| GXP_1798493 [GXP_1798493] (1-668) Gpr176, GXL_240571, GeneID: 381413, *Mus musculus* chr. 2 G protein-coupled receptor 176 | RXRF_SF1F_02 | 205-232 | (+) |
| GXP_2046947 [GXP_2046947] (1-604) Tbl2, GXL_240884, GeneID: 27368, *Mus musculus* chr. 5 transducin (beta)-like 2 | RXRF_SF1F_02 | 210-183 | (−) |
| GXP_2044366 [GXP_2044366] (1-614) Stk25, GXL_242978, GeneID: 59041, *Mus musculus* chr. 1 serine/threonine kinase 25 (yeast) | RXRF_SF1F_02 | 298-271 | (−) |
| GXP_1795374 [GXP_1795374] (1-1306) H2-DMa, GXL_251594, GeneID: 14998, *Mus musculus* chr. 17 histocompatibility 2, class II, locus DMa | RXRF_SF1F_02 | 1046-1073 | (+) |
| GXP_299578 [GXP_299578] (1-977) Pou5f1, GXL_251685, GeneID: 18999, *Mus musculus* chr. 17 POU domain, class 5, transcription factor 1 | RXRF_SF1F_02 | 760-787 | (+) |
| GXP_1793956 [GXP_1793956] (1-624) C7, GXL_258854, GeneID: 109828, *Mus musculus* chr. 15 complement component 7 | RXRF_SF1F_02 | 382-355 | (−) |
| GXP_2044577 [GXP_2044577] (1-606) Pbx1, GXL_271528, GeneID: 18514, *Mus musculus* chr. 1 pre B-cell leukemia transcription factor 1 | RXRF_SF1F_02 | 152-125 | (−) |
| GXP_411169 [GXP_411169] (1-601) Tanc2, GXL_273504, GeneID: 77097, *Mus musculus* chr. 11 tetratricopeptide repeat, ankyrin repeat and coiled-coil containing 2 | RXRF_SF1F_02 | 135-162 | (+) |
| GXP_2043287 [GXP_2043287] (1-601) H2-DMb1, GXL_278291, GeneID: 14999, *Mus musculus* chr. 17 histocompatibility 2, class II, locus Mb1 | RXRF_SF1F_02 | 342-369 | (+) |
| GXP_816740 [GXP_816740] (1-619) Impa1, GXL_281247, GeneID: 55980, *Mus musculus* chr. 3 inositol (myo)-1(or 4)-monophosphatase 1 | RXRF_SF1F_02 | 195-222 | (+) |
| GXP_2047788 [GXP_2047788] (1-601) Hsd17b14, GXL_286930, GeneID: 66065, *Mus musculus* chr. 7 hydroxysteroid (17-beta) dehydrogenase 14 | RXRF_SF1F_02 | 549-576 | (+) |
| GXP_2042863 [GXP_2042863] (1-601) Snx29, GXL_461294, GeneID: 74478, *Mus musculus* chr. 16 sorting nexin 29 | RXRF_SF1F_02 | 213-186 | (−) |
| GXP_412534 [GXP_412534] (1-601) 100040879, GXL_659082, GeneID: 100040879, *Mus musculus* chr. 12 predicted gene, 100040879 | RXRF_SF1F_02 | 597-570 | (−) |
| GXP_431619 [GXP_431619] (1-601) Tmod1, GXL_661320, GeneID: 21916, *Mus musculus* chr. 4 tropomodulin 1 | RXRF_SF1F_02 | 259-232 | (−) |
| GXP_2046709 [GXP_2046709] (1-610) Slc4a4, GXL_661656, GeneID: 54403, *Mus musculus* chr. 5 solute carrier family 4 (anion exchanger), member 4 | RXRF_SF1F_02 | 42-69 | (+) |

A total of 38 matches was found in 38 sequences. Sequences searched: 65829 (43681672 bp).

TABLE 2

| Sequence | Model Name | Position | Strand |
|---|---|---|---|
| GXP_38642 [GXP_38642] (1-601) PRPF31, GXL_32057, GeneID: 26121, *Homo sapiens* chr. 19 PRP31 pre-mRNA processing factor 31 homolog (*S. cerevisiae*) | RXRF_SF1F_02 | 32-62 | (+) |

TABLE 2-continued

| Sequence | Model Name | Position | Strand |
|---|---|---|---|
| GXP_1255917 [GXP_1255917] (1-629) PITPNM1, GXL_41522, GeneID: 9600, *Homo sapiens* chr. 11 phosphatidylinositol transfer protein, membrane-associated 1 | RXRF_SF1F_02 | 196-169 | (−) |
| GXP_52656 [GXP_52656] (1-916) POU5F1, GXL_43374, GeneID: 5460, *Homo sapiens* chr. 6 POU class 5 homeobox 1 | RXRF_SF1F_02 | 695-722 | (+) |
| GXP_1814152 [GXP_1814152] (1-1138) TMEM102, GXL_45908, GeneID: 284114, *Homo sapiens* chr. 17 transmembrane protein 102 | RXRF_SF1F_02 | 208-181 | (−) |
| GXP_1815496 [GXP_1815496] (1-613) TNFRSF11A, GXL_47222, GeneID: 8792, *Homo sapiens* chr. 18 tumor necrosis factor receptor superfamily, member 11a, NFKB activator | RXRF_SF1F_02 | 3-58 | (+) |
| GXP_1260208 [GXP_1260208] (1-602) CDH5, GXL_89968, GeneID: 1003, *Homo sapiens* chr. 16 cadherin 5, type 2 (vascular endothelium) | RXRF_SF1F_02 | 184-155 | (−) |
| GXP_116394 [GXP_116394] (1-685) NSUN5, GXL_97642, GeneID: 55695, *Homo sapiens* chr. 7 NOL1/NOP2/Sun domain family, member 5 | RXRF_SF1F_02 | 41-68 | (+) |
| GXP_1818489 [GXP_1818489] (1-602) BAT2D1, GXL_120915, GeneID: 23215, *Homo sapiens* chr. 1 BAT2 domain containing 1 | RXRF_SF1F_02 | 534-561 | (+) |
| GXP_160425 [GXP_160425] (1-956) DPEP3, GXL_133499, GeneID: 64180, *Homo sapiens* chr. 16 dipeptidase 3 | RXRF_SF1F_02 | 187-214 | (+) |
| GXP_160480 [GXP_160480] (1-886) PYDC1, GXL_133531, GeneID: 260434, *Homo sapiens* chr. 16 PYD (pyrin domain) containing 1 | RXRF_SF1F_02 | 6-33 | (+) |
| GXP_1810489 [GXP_1810489] (1-602) CCT2, GXL_141723, GeneID: 10576, *Homo sapiens* chr. 12 chaperonin containing TCP1, subunit 2 (beta) | RXRF_SF1F_02 | 228-255 | (+) |
| GXP_1273930 [GXP_1273930] (1-1366) ATXN7L1, GXL_182315, GeneID: 222255, *Homo sapiens* chr. 7 ataxin 7-like 1 | RXRF_SF1F_02 | 364-391 | (+) |
| GXP_221757 [GXP_221757] (1-601) C9orf86, GXL_184953, GeneID: 55684, *Homo sapiens* chr. 9 chromosome 9 open reading frame 86 | RXRF_SF1F_02 | 419-392 | (−) |
| GXP_1259198 [GXP_1259198] (1-733) SNX1, GXL_230316, GeneID: 6642, *Homo sapiens* chr. 15 sorting nexin 1 | RXRF_SF1F_02 | 61-88 | (+) |
| GXP_1479250 [GXP_1479250] (1-635) GALNTL1, GXL_247708, GeneID: 57452, *Homo sapiens* chr. 14 UDP-N-acetyl-alpha-D-galactosamine: polypeptide N-acetylgalactosaminyltransferase-like 1 | RXRF_SF1F_02 | 84-111 | (+) |
| GXP_2051860 [GXP_2051860] (1-601) C14orf166, GXL_247796, GeneID: 51637, *Homo sapiens* chr. 14 chromosome 14 open reading frame 166 | RXRF_SF1F_02 | 67-40 | (−) |
| GXP_297369 [GXP_297369] (1-639) MB, GXL_249810, GeneID: 4151, *Homo sapiens* chr. 22 myoglobin | RXRF_SF1F_02 | 60-33 | (−) |
| GXP_2054048 [GXP_2054048] (1-601) MAG, GXL_262148, GeneID: 4099, *Homo sapiens* chr. 19 myelin associated glycoprotein | RXRF_SF1F_02 | 17-44 | (+) |
| GXP_210437 [GXP_210437] (1-602) RNF213, GXL_316752, GeneID: 57674, *Homo sapiens* chr. 17 ring finger protein 213 | RXRF_SF1F_02 | 207-234 | (+) |
| GXP_488164 [GXP_488164] (1-655) YDJC, GXL_316849, GeneID: 150223, *Homo sapiens* chr. 22 | RXRF_SF1F_02 | 228-201 | (−) |

TABLE 2-continued

| Sequence | Model Name | Position | Strand |
|---|---|---|---|
| YdjC homolog (bacterial) GXP__1499697 [GXP__1499697] (1-605) CCDC125, GXL__383423, GeneID: 202243, *Homo sapiens* chr. 5 coiled-coil domain containing 125 | RXRF__SF1F__02 | 302-275 | (−) |
| GXP__1497474 [GXP__1497474] (1-663) RPL22L1, GXL__694179, GeneID: 200916, *Homo sapiens* chr. 3 ribosomal protein L22-like 1 | RXRF__SF1F__02 | 50-23 | (−) |
| GXP__14398 [GXP__14398] (1-753) ALG13, GXL__695854, GeneID: 79868, *Homo sapiens* chr. X asparagine-linked glycosylation 13 homolog (*S. cerevisiae*) | RXRF__SF1F__02 | 164-137 | (−) |
| GXP__91298 [GXP__91298] (1-707) CORO7, GXL__744275, GeneID: 79585, *Homo sapiens* chr. 16 coronin 7 | RXRF__SF1F__02 | 626-599 | (−) |
| GXP__122795 [GXP__122795] (1-901) CRHR1, GXL__744353, GeneID: 1394, *Homo sapiens* chr. 17 corticotropin releasing hormone receptor 1 | RXRF__SF1F__02 | 307-280 | (−) |
| GXP__1821114 [GXP__1821114] (1-602) ANKRD39, GXL__744677, GeneID: 51239, *Homo sapiens* chr. 2 ankyrin repeat domain 39 | RXRF__SF1F__02 | 80-107 | (+) |
| GXP__1821115 [GXP__1821115] (1-601) ANKRD39, GXL__744677, GeneID: 51239, *Homo sapiens* chr. 2 ankyrin repeat domain 39 | RXRF__SF1F__02 | 249-276 | (+) |

A total of 27 matches was found in 27 sequences. Sequences searched: 78566 (52385643 bp).

TABLE 3

| Primer Name | Primer Sequence | Purpose |
|---|---|---|
| HMSpAs | CGAAGAGTAACCGTTGCTAGGAGAGACCGTGGCTGAATGAGACTGGTGTCGACACTAGTGG | Splinkerette adaptor |
| HMSpBb-Sau3AI | gatcCCACTAGTGTCGACACCAGTCTCTAATTTTTTTTTCAAAAAAA | Splinkerette adaptor |
| HMSp1 | CGAAGAGTAACCGTTGCTAGGAGAGACC | 1st round PCR primers |
| HMSp2 | GTGGCTGAATGAGACTGGTGTCGAC | 2nd round PCR primers |
| HMSp3 | GGTGTCGACACTAGTGG | Sequencing primers |
| PB-L-Sp1 | CAGTGACACTTACCGCATTGACAAGCACGC | 1st round PCR primers, used together with HMSp1 |
| PB-L-Sp2 | GAGAGAGCAATATTTCAAGAATGCATGCGT | 2nd round PCR primers, used together with HMSp2 |
| PB-L-Sp3 | GCGCTTTACTCGACCTAAACTTTAA | Sequencing primers |
| PB-R-Sp1 | CCTCGATATACAGACCGATAAAACAGATGC | 1st round PCR primers, used together with HMSp1 |
| PB-R-Sp2 | ACGCATGATTATCTTTAACGTACGTCACAA | 2nd round PCR primers, used together with HMSp2 |
| PB-R-Sp3 | CGTCACAATATGATTATCTTTCTAGG | Sequencing primers |

TABLE 4

| Primer Name | Primer Sequence | Purpose |
|---|---|---|
| mOct4-F-BgIII | GAAGATCTCTCCACCTTCCCCATGGCTGGACACC | mOct4 ORF cloning |
| mOct4-R-EcoRI | CGGAATTCTTGATCAACAGCATCACTGAGCTTC | |

TABLE 4-continued

| Primer Name | Primer Sequence | Purpose |
| --- | --- | --- |
| mSox2-F-BgIII | GAAGATCTCTTGTATAACATGATGGAGACGG | mSox2 ORF cloning |
| mSox2-R-EcoRI | CGGAATTCTTTCACATGTGCGACAGGGGCAGT | |
| mKlf4-F-BgIII | GAAGATCTCACCATGGCTGTCAGCGACGCTCTGCTC | mKlf4 ORF cloning |
| mKlf4-R-EcoRI | CGGAATTCACATCCACTACGTGGGATTTAAAA | |
| mcMyc-F-BgIII | GAAGATCTCACCATGCCCCTCAACGTGAACTTCACC | mcMyc ORF cloning |
| mcMyc-R-EcoRI | CGGAATTCTTATGCACCAGAGTTTCGAAGCTGTTCG | |
| mRarg-FL/DN-F-EcoRI | GGGAATTCCCGCAGCTACCATGGCCACC | mRarg-FL/DN cloning |
| m Rarg-DN-R-XbaI | GCTCTAGATCATCATCATCCCTTAGTGCTGATGC | mRarg-DN cloning |
| mRarg-FL-R-XbaI | GCTCTAGAGCCCAACCCCACAACGGGG | mRarg-FL cloning |
| mRara-FL/DN-F-EcoRI | GGGAATTCGCTGCTTGGCATGGCCAGCA | mRara-FL/DN cloning |
| mRara-DN-R-XbaI | GCTCTAGATCATCATCATGGGATCTCCATCTTCAA | mRara-DN cloning |
| mRara-FL-R-XbaI | GCTCTAGAGTGTCGAGGTGGTCATGGGGAT | mRara-FL cloning |
| mSf1-F-EcoRI | GGGAATTCCCGCGGGCATGGACTATTCGTACG | mSf1 ORF cloning |
| mSf1-R-XbaI | GCTCTAGAGGCACCCAGGCTCAAGTCTGCTTG | |
| mLrh1-F-EcoRI | GGGAATTCTTTCGCTAAGAATGTCTGCTAGTTTGG | mLrh 1 ORF cloning |
| mLrh1-R-XbaI | GCTCTAGAGGGGACTTAGGCTCTTTTGGCATGC | |
| hOCT4-F-EcoRI | GGGAATTCCACCATGGCGGGACACCTGGCTTCAG | hOCT4 ORF cloning |
| hOCT4-R-XbaI | GCTCTAGAACCTCAGTTTGAATGCATGGGAGAGC | |
| hSOX2-F-EcoRI | GGGAATTCCACCATGTACAACATGATGGAGACGGAGCTG | hSOX2 ORF cloning |
| hSOX2-R-XbaI | GCTCTAGATCACATGTGTGAGAGGGGCAGTGTGC | |
| hKLF4-F-EcoRI | GGGAATTCCACCATGGCTGTCAGTGACGCGCTGCTCCC | hKLF4 ORF cloning |
| hKLF4-R-XbaI | GCTCTAGATTAAAAATGTCTCTTCATGTGTAAGGCGAG | |
| hCMYC-F-EcoRI | GGGAATTCCACCATGCCCCTCAACGTTAGCTTCACCAA | hCMYC ORF cloning |
| hCMYC-R-XbaI | GCTCTAGATCACGCACAAGAGTTCCGTAGCTGTTCAAG | |
| hLRH1-F-EcoRI | GGGAATTCATGTCTTCTAATTCAGATACTGGGG | hLRH1 ORF cloning |
| hLRH1-R-XbaI | GCTCTAGATTATGCTCTTTTGGCATGCAAC | |
| hRARG-F-EcoRI | GGGAATTCATGGCCACCAATAAGGAGCG | hRARG ORF cloning |
| hRARG-R-XbaI | GCTCTAGATCAGGCTGGGACTTCAGGCC | |

TABLE 5

| Primer Name | Primer Sequence | Target |
| --- | --- | --- |
| mOct4-RT-En-F | TCTTTCCACCAGGCCCCCGGCTC | RT-PCR for endogenous mOct3/4 |
| mOct4-RT-En-R | GCGGGCGGACATGGGAGATCC | |
| mSox2-RT-En-F | TTGCCTTAAACAAGACCACGAAA | RT-PCR for endogenous mSox2 |
| mSox2-RT-En-R | TAGAGCTAGACTCCGGGCGATGA | |
| mKlf4-RT-En-F | GCGAACTCACACAGGCGAGAAACC | RT-PCR for endogenous mKlf4 |
| mKlf4-RT-En-R | TCGCTTCCTCTTCCTCCGACACA | |
| mNanog-RT-En-F | CAGGTGTTTGAGGGTAGCTC | RT-PCR for mNanog |
| mNanog-RT-En-R | CGGTTCATCATGGTACAGTC | |
| mRex1-RT-F | ACGAGTGGCAGTTTCTTCTTGGGA | RT-PCR for mRex1 |
| mRex1-RT-R | TATGACTCACTTCCAGGGGCACT | |
| mEsg1-RT-F | GAAGTCTGGTTCCTTGGCAGGATG | RT-PCR for mEsg1 |
| mEsg1-RT-R | ACTCGATACACTGGCCTAGC | |

TABLE 5-continued

| Primer Name | Primer Sequence | Target |
|---|---|---|
| mFgf4-RT-F | CGTGGTGAGCATCTTCGGAGTGG | RT-PCR for mFgf4 |
| mFgf4-RT-R | CCTTCTTGGTCCGCCCGTTCTTA | |
| mDax1-RT-F | TGCTGCGGTCCAGGCCATCAAGAG | RT-PCR for mDax1 |
| mDax1-RT-R | GGGCACTGTTCAGTTCAGCGGATC | |
| mGdf3-RT-F | GTTCCAACCTGTGCCTCGCGTCTT | RT-PCR for mGdf3 |
| mGdf3-RT-R | AGCGAGGCATGGAGAGAGCGGAGCAG | |
| mUtf1-RT-F | GGATGTCCCGGTGACTACGTCTG | RT-PCR for mUtf1 |
| mUtf1-RT-R | GGCGGATCTGGTTATCGAAGGGT | |
| mOct4-DMR-F2 | TGGGTTGAAATATTGGGTTTATTT | DMR primers for mOct4 promoter |
| mOct4-DMR-R2 | CTAAAACCAAATATCCAACCATA | |
| mNanog-DMR-F | GATTTTGTAGGTGGGATTAATTGTGAATTT | DMR primers for mNanog promoter |
| mNanog-DMR-R | ACCAAAAAAACCCACACTCATATCAATATA | |
| mRex1-DMR-F2 | TATATTAATGTTGGAAAAAGTTTAGGTAAT | DMR primers for mRex1 promoter |
| mRex1-DMR-R2 | AACTCCTTAAACCCCTCCCTTTTTAAATAA | |
| hOCT4-RT-endo-F | GACAGGGGGAGGGGAGGAGCTAGG | RT-PCR for endogenous hOCT3/4 |
| hOCT4-RT-endo-R | CTTCCCTCCAACCAGTTGCCCCAAAC | |
| hSOX2-RT-endo-F | GGGAAATGGGAGGGGTGCAAAAGAGG | RT-PCR for endogenous hSOX2 |
| hSOX2-RT-endo-R | TTGCGTGAGTGTGGATGGGATTGGTG | |
| hKLF4-RT-endo-F | ACGATCGTGGCCCCGGAAAAGGACC | RT-PCR for endogenous hKLF4 |
| hKLF4-RT-endo-R | GCGTCCTGGGAAGGGAGATCCGGAGC | |
| hCMYC-RT-endo-F | GCGTCCTGGGAAGGGAGATCCGGAGC | RT-PCR for endogenous hCMYC |
| hCMYC-RT-endo-R | TTGAGGGGCATCGTCGCGGGAGGCTG | |
| hNANOG-RT-F | CAGCCCCGATTCTTCCACCAGTCCC | RT-PCR for hNANOG |
| hNANOG-RT-R | CGGAAGATTCCCAGTCGGGTTCACC | |
| hREX1-RT-F | CAGATCCTAAACAGCTCGCAGAAT | RT-PCR for hREX1 |
| hREX1-RT-R | GCGTACGCAAATTAAAGTCCAGA | |
| hTERT-RT-F | CCTGCTCAAGCTGACTCGACACCGTG | RT-PCR for hTERT |
| hTERT-RT-R | GGAAAAGCTGGCCCTGGGGTGGAGC | |
| hDNMT3B-RT-F | TGCTGCTCACAGGGCCCGATACTTC | RT-PCR for hDNMT3 |
| hDNMT3B-RT-R | TCCTTTCGAGCTCAGTGCACCACAAAAC | |

REFERENCES FOR TABLE 5

Takahashi, K. & Yamanaka, S. Induction of pluripotent stem cells from mouse embryonic and adult fibroblast cultures by defined factors. Cell 126, 663-76 (2006).

Takahashi, K. et al. Induction of pluripotent stem cells from adult human fibroblasts by defined factors. Cell 131, 861-72 (2007).

TABLE 6

| Assay ID | Gene Symbol | Gene Name |
|---|---|---|
| Mm00658129_gH | Pou5f1, mCG19893 | POU domain, class 5, transcription factor 1, Gene mCG19893 Celera Annotation |
| Mm00516104_m1 | Klf4, mCG20055 | Kruppel-like factor 4 (gut), Gene mCG20055 Celera Annotation |
| Mm02384862_g1 | Nanog, Nanogpd, mCG132219, mCG56641 | Nanog homeobox, similar to Nanog homeobox, Gene mCG132219 Celera Annotation, Gene mCG56641 Celera Annotation |
| Mm03053975_g1 | Zfp42, mCG10211 | zinc finger protein 42, Gene mCG10211 Celera Annotation |
| 4352341E | β-actin (Actb) | Mouse ACTB (actin, beta) Endogenous Control (VIC ®/ MGB Probe, Primer Limited) |
| Hs01053049_s1 | SOX2, hCG2021648 | SRY (sex determining region Y)-box 2, Gene hCG2021649 Celera Annotation |
| Hs02387400_g1 | NANOG, hCG1745097, hCG1730824 | Nanog homeobox, Gene hCG1745097 Celera AnnotationGene hCG1730824 Celera Annotation |
| Hs00999632_g1 | POU5F1, hCG25999 | POU class 5 homeobox 1, Gene hCG25999 Celera Annotation |
| Hs00358836_m1 | KLF4, hCG1738095 | Kruppel-like factor 4 (gut), Gene hCG1738095 Celera Annotation |

TABLE 6-continued

| Assay ID | Gene Symbol | Gene Name |
|---|---|---|
| Hs01931905_g1 | DPPA3 | developmental pluripotency associated 3 |
| Hs00415443_m1 | NODAL, hCG23654 | nodal homolog (mouse), Gene hCG23654 Celera Annotation |
| Hs00232018_m1 | GATA6, hCG37191 | GATA binding protein 6Gene hCG37191 Celera Annotation |
| Hs00751752_s1 | SOX17, hCG40422 | SRY (sex determining region Y)-box 17, Gene hCG40422 Celera Annotation |
| Hs01057642_s1 | SOX1, hCG1640458 | SRY (sex determining region Y)-box 1 Gene hCG1640458 Celera Annotation |
| Hs01088114_m1 | PAX6, hCG26499 | paired box 6, Gene hCG26499 Celera Annotation |
| 4326317E | GAPDH | TaqMan ® Endogenous Control, GAPDH |

TABLE 7

| Name | Sequence |
|---|---|
| hCMYC-taq-endo-F | CCTGAGCAATCACCTATGAACTTG |
| hCMYC-taq-endo-R | TTATGCCCAAAGTCCAATTTGA |
| hCMYC-taq-endo-probe | CAAATGCAACCTCACAACCTTGGCTG |
| hKLF4-taq-endo-F | TTTCACACTGTCTTCCCGATGA |
| hKLF4-taq-endo-R | TCCTGATTATCCACTCACAAGATGA |
| hKLF4-taq-endo-probe | CCAGCCAGAAAGCACTACAATCATGGTCAA |
| hOCT4-taq-endo-F | CACTGTACTCCTCGGTCCCTTTC |
| hOCT4-taq-endo-R | CAACCAGTTGCCCCAAACTC |
| hOCT4-taq-endo-probe | CTTTCCCCCTGTCTCCGTCACCACTC |
| hSOX2-taq-endo-F | ACAGCAAATGACAGCTGCAAA |
| hSOX2-taq-endo-R | AAGTCCAGGATCTCTCTCATAAAAGTTT |
| hSOX2-taq-endo-probe | ATCCACACTCACGCAAAAACCGCG |
| hLRH1-taq-endo-F | AAAGCTGAACTGAAACAATTCTCAAG |
| hLRH1-taq-endo-R | GCTCGGGCCTTCAAAGGA |
| hLRH1-taq-endo-probe | TGCATCAGCTGTACCTACAATAGCCCCTCC |
| hRARG-taq-endo-F | GAGCCTGGGTTTGGACTCTAAA |
| hRARG-taq-endo-R | CCTCTTGCCCTGGGAAGTCT |
| hRARG-taq-endo-probe | CTCAGCACTGCCCCATGGGTCC |

The invention claimed is:

1. A method for preparing an induced pluripotent stem (iPS) cell comprising: i) transfecting an isolated somatic cell with: a nucleic acid sequence encoding Oct4, a nucleic acid sequence encoding Sox2, a nucleic acid sequence encoding Klf4, a nucleic acid sequence encoding retinoic acid receptor gamma (Rarg), and a nucleic acid sequence encoding liver receptor homologue 1 (LHR1), each of which is operably linked to a promoter; and ii) culturing the cells such that iPS cells are obtained.

2. A vector encoding:
Oct4, Sox2, Klf4, retinoic acid receptor gamma (Rarg), and liver receptor homologue 1 (LHR1) each of which is operably linked to a promoter.

3. The vector according to claim 2, wherein the vector is a transposon.

4. The method of claim 1, wherein the vector further comprises a nucleic acid sequence encoding c-Myc operably linked to a promoter.

5. The vector according to claim 2, wherein the vector further comprises a nucleic acid sequence encoding cMyc operably linked to a promoter.

6. The method of claim 1, wherein each nucleic acid sequence is operably linked to one promoter.

7. The method of claim 1, wherein each nucleic acid sequence is operably linked to a different promoter.

8. The method of claim 1, wherein one or more of the nucleic acid sequences is operably linked to one promoter.

9. The method of claim 2, wherein each nucleic acid sequence is operably linked to one promoter.

10. The method of claim 2, wherein each nucleic acid sequence is operably linked to a different promoter.

11. The method of claim 2, wherein one or more of the nucleic acid sequences is operably linked to one promoter.

* * * * *

UNITED STATES PATENT AND TRADEMARK OFFICE
CERTIFICATE OF CORRECTION

PATENT NO. : 9,512,407 B2
APPLICATION NO. : 13/394481
DATED : December 6, 2016
INVENTOR(S) : Liu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 711 days.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*